US012612461B2

(12) United States Patent (10) Patent No.: US 12,612,461 B2
Lobb et al. (45) Date of Patent: Apr. 28, 2026

(54) SINGLE DOMAIN ANTIBODIES AGAINST CLL-1

(71) Applicant: Aleta Biotherapeutics Inc., Natick, MA (US)

(72) Inventors: Roy Lobb, Wellesley, MA (US); Paul Rennert, Holliston, MA (US)

(73) Assignee: Aleta Biotherapeutics, Inc., Natick, MA (US)

( * ) Notice: Subject to any disclaimer, the term of this patent is extended or adjusted under 35 U.S.C. 154(b) by 1154 days.

(21) Appl. No.: 17/298,246

(22) PCT Filed: Nov. 27, 2019

(86) PCT No.: PCT/US2019/063691
§ 371 (c)(1),
(2) Date: May 28, 2021

(87) PCT Pub. No.: WO2020/113063
PCT Pub. Date: Jun. 4, 2020

(65) Prior Publication Data
US 2022/0112292 A1    Apr. 14, 2022

Related U.S. Application Data

(60) Provisional application No. 62/780,092, filed on Dec. 14, 2018, provisional application No. 62/774,025, filed on Nov. 30, 2018.

(51) Int. Cl.
*C07K 16/28*        (2006.01)
*A61K 39/00*        (2006.01)

(52) U.S. Cl.
CPC .... *C07K 16/2851* (2013.01); *A61K 2039/505* (2013.01); *C07K 2317/569* (2013.01); *C07K 2319/21* (2013.01); *C07K 2319/41* (2013.01)

(58) Field of Classification Search
None
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | DeCant, Jr. et al. | |
| 4,447,233 A | 5/1984 | Mayfield | |
| 4,475,196 A | 10/1984 | La Zor | |
| 4,486,194 A | 12/1984 | Ferrara | |
| 4,487,603 A | 12/1984 | Harris | |
| 4,596,556 A | 6/1986 | Morrow et al. | |
| 4,790,824 A | 12/1988 | Morrow et al. | |
| 4,941,880 A | 7/1990 | Burns | |
| 5,064,413 A | 11/1991 | McKinnon et al. | |
| 5,312,335 A | 5/1994 | McKinnon et al. | |

| | | | |
|---|---|---|---|
| 5,383,851 A | 1/1995 | McKinnon, Jr. et al. | |
| 5,399,163 A | 3/1995 | Peterson et al. | |
| 5,641,640 A | 6/1997 | Hanning | |
| 5,994,136 A | 11/1999 | Naldini et al. | |
| 6,165,782 A | 12/2000 | Naldini et al. | |
| 6,180,370 B1 | 1/2001 | Queen et al. | |
| 6,326,193 B1 | 12/2001 | Liu et al. | |
| 6,428,953 B1 | 8/2002 | Naldini et al. | |
| 7,741,443 B2 | 6/2010 | van den Oudenrijn et al. | |
| 8,394,411 B2 | 3/2013 | Roberts et al. | |
| 2010/0285037 A1 | 11/2010 | Abo et al. | |
| 2013/0295118 A1 | 11/2013 | Jiang et al. | |
| 2016/0368994 A1 | 12/2016 | Kelley et al. | |
| 2018/0273633 A1 | 9/2018 | Jiang et al. | |

FOREIGN PATENT DOCUMENTS

| | | | | |
|---|---|---|---|---|
| JP | 2015/519336 A | 7/2015 | | |
| JP | 2018/508229 A | 3/2018 | | |
| WO | WO-92/22324 A1 | 12/1992 | | |
| WO | WO-94/04678 A1 | 3/1994 | | |
| WO | WO-98/46645 A2 | 10/1998 | | |
| WO | WO-01/29058 A1 | 4/2001 | | |
| WO | WO-01/96584 A2 | 12/2001 | | |
| WO | WO-2013/169625 A1 | 11/2013 | | |
| WO | WO-2015/150815 A1 | 10/2015 | | |
| WO | WO-2016/040868 A1 | 3/2016 | | |
| WO | WO-2016/122320 A1 | 8/2016 | | |
| WO | WO-2017/075533 | 5/2017 | | |
| WO | WO-2017/075537 | 5/2017 | | |
| WO | WO-2017/091615 A1 | 6/2017 | | |
| WO | WO-2018156791 A1 | 8/2018 | | |
| WO | WO-2018156802 A1 | 8/2018 | | |
| WO | WO 2019/118918 * | 6/2019 | ............ | A61K 38/17 |
| WO | WO-2020/113063 A1 | 6/2020 | | |

OTHER PUBLICATIONS

Allen, T. M., Ligand-targeted therapeutics in anticancer therapy, Nat. Rev. Cancer 2:750-763 (2002).
Bakker, A. et al., C-type lectin-like molecule-1: a novel myeloid cell surface marker associated with acute myeloid leukemia, Cancer Res., 64:8443-8450 (2004).
Bannas, P. et al., Nanobodies and Nanobody-based Human Heavy Chain Antibodies as Antitumor Therapeutics, Frontiers in Immunology, 8(22):5-6 (2017).
Bich, C. et al., Reactivity and applications of new amine reactive cross-linkers for mass spectrometric detection of protein-protein complexes, Anal. Chem., 82 (1):172-179 (2010).
Brinkman, U. et al., Phage display of disulfide-stabilized Fv fragments, T. Immunol. Methodsm 182:41-50 (1995).

(Continued)

*Primary Examiner* — Nora M Rooney
(74) *Attorney, Agent, or Firm* — Choate, Hall & Stewart LLP; Brenda Herschbach Jarrell; Rolando Medina

(57) ABSTRACT

Antibodies that specifically bind to CLL-1 are described, as well as methods of making and using such antibodies.

13 Claims, 34 Drawing Sheets
Specification includes a Sequence Listing.

(56) References Cited

OTHER PUBLICATIONS

Dufort, F. et al., Abstract 11102, Hijacking CAR19 T Cells to target diverse hematologic and solid tumors, XP055568505, Retrieved from the internet http:/www.aletabio.com/wp-content/uploads/2018/11/SITC18-267_RED.pdf (2018).

Herrmann, H. et al., CD34(+)/CD38(-) stem cells in chronic myeloid leukemia express Siglec-3 (CD33) and are responsive to the CD33-targeting drug gemtuzumab/ozogamicin, Haematologica, 97(2):219-26 (2012).

Hung, C. et al., Ovarian cancer gene therapy using HPV-16 pseudovirion carrying the HSV-tk gene, PLoS One, 7(7):e40983 (2012).

International Search Report for PCT/US2019/063691 (Single Domain Antibodies Against CLL-1, filed Nov. 27, 2019) received from ISA/US, 5 pages (Mar. 11, 2020).

Morrison, S. L., Transfectomas provide novel chimeric antibodies, Science, 229(4719):1202-7 (1985).

Morsink, L. M. et al., Prognostic and therapeutic role of CLEC12A in acute myeloid leukemia, Blood Rev., 34:26-33 (2018).

Muyldermans, S. et al., Nanobodies: Natural Single-Domain Antibodies, Annual Review of Biochemistry, 82(1):784-786 (2013).

Pastan, I., Immunotoxins in cancer therapy, Curr. Opin. Investig. Drugs, 3:1089-1091 (2002).

Payne, G., Progress in immunoconjugate cancer therapeutics, Cancer Cell, 3:207-212 (2003).

Riechmann, L. et al., Single domain antibodies: comparison of camel VH and camelised human VH domains, J. Immunol. Methods, 231:25-38 (1999).

Saito, G. et al., Drug delivery strategy utilizing conjugation via reversible disulfide linkages: role and site of cellular reducing activities, Adv. Drug Deliv. Rev. 55:199-215 (2003).

Segal, D. M. et al., Introduction: bispecific antibodies, J. Immunol. Methods, 248:1-6 (2001).

Senter, P. D., Selective activation of anticancer prodrugs by monoclonal antibody-enzyme conjugates, Adv. Drug Deliv. Rev., 53:247-264 (2001).

Sjolander, S. et al., Integrated fluid handling system for biomolecular interaction analysis, Anal. Chem. 63:2338-2345 (1991).

Szabo, A. et al., Surface plasmon resonance and its use in biomolecular interaction analysis (BIA), Curr. Opin. Struct. Biol. 5:699-705 (1995).

Trail, P. A. et al., Monoclonal antibody drug immunoconjugates for targeted treatment of cancer, Cancer Immunol. Immunother. 52:328-337 (2003).

Tutt, A. et al., Trispecific F(ab')3 derivatives that use cooperative signaling via the TCR/CD3 complex and CD2 to activate and redirect resting cytotoxic T cells, J. Immunol., 147:60 (1991).

Van Rhenen, A et al., Aberrant marker expression patterns on the CD34+CD38-stem cell compartment in acute myeloid leukemia allows to distinguish the malignant from the normal stem cell compartment both at diagnosis and in remission, Leukemia, 21:1700-7 (2007).

Van Rhenen, A. et al., The novel AML stem cell associated antigen CLL-1 aids in discrimination between normal and leukemic stem cells, Blood, 110:2659-66 (2007).

Written Opinion for PCT/US2019/063691 (Single Domain Antibodies Against CLL-1, filed Nov. 27, 2019) received from ISA/US, 6 pages (Mar. 11, 2020).

Zhao, X. et al., Targeting C-type lectin-like molecule-1 for antibody-mediated immunotherapy in acute myeloid leukemia, Haematologica, 95:71-78 (2010).

* cited by examiner

| CLL1 clone | EC50 |
|------------|-----------|
| 1G6 | 480 pM |
| 2H3 | 610 pM |
| 1H1 | 900 pM |
| 2F5 | 650 pM |
| 2F3 | 1,500 pM |
| 1B5 | 19,500 pM |

| | Plot 9 (FL2-A/SSC-A) | | |
|---|---|---|---|
| | R3 (PE+) | | |
| | Count | % of This Plot | Mean FL2-A |
| A01 U937 unstained | 43 | 0.6% | 5,793.5 |
| A02 U937 + msIgG2a-PE | 36 | 0.5% | 5,284.6 |
| A03 U937 + a-CLL1-PE | 8,177 | 99.7% | 35,116.3 |
| A04 U937 + a-His-PE | 89 | 1.1% | 5,576.5 |
| A05 U937 + 1B5 + a-His-PE | 197 | 2.3% | 4,131.9 |
| A06 U937 + 1H1 + a-His-PE | 7,536 | 88.6% | 6,731.6 |
| A07 U937 + 1G6 + a-His-PE | 8,149 | 95.6% | 9,314.4 |
| A08 U937 + 2F3 + a-His-PE | 1,087 | 12.4% | 3,566.2 |
| A09 U937 + 2F5 + a-His-PE | 8,073 | 95.5% | 9,260.4 |
| A10 U937 + 2H3 + a-His-PE | 8,234 | 93.8% | 8,127.9 |

CLL1 expression on U937

A03 U937 + a-CLL1-PE
Gate: (P3 in P1)

- A03 U937 + a-CLL1-PE
- A02 U937 + msIgG2a-PE
- A01 U937 unstained

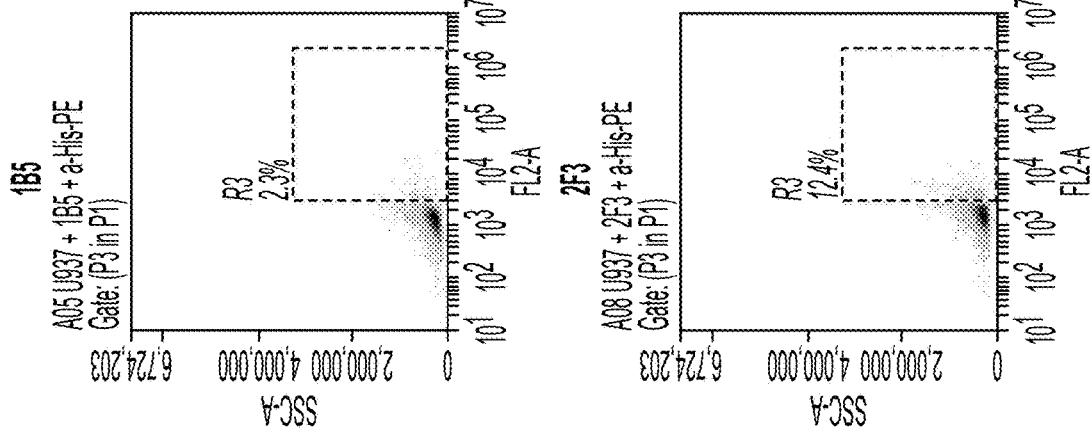
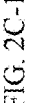
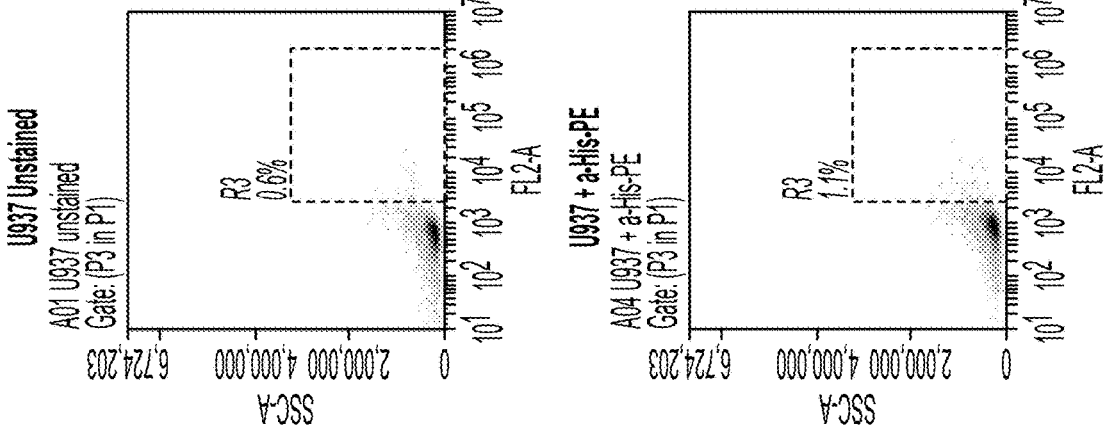
FIG. 2C-1

|  | Plot 9 (FL2-A/SSC-A) | | |
|  | R3 (PE+) | | |
|  | Count | % of This Plot | Mean FL2-A |
| A01 293-CLL1 unstained | 75 | 1.0% | 6,315.7 |
| A02 293-CLL1 + mslgG2a-PE | 102 | 1.6% | 5,966.6 |
| A03 293-CLL1 + a-CLL1-PE | 7,818 | 99.7% | 1,019,447.9 |
| B01 U937 Unstained | 19 | 0.3% | 820,950.2 |
| B02 U937-CLL1 + mslgG2a-PE | 5 | 0.1% | 5,214.4 |
| B03 U937-CLL1 + a-CLL1-PE | 8,793 | 99.2% | 37,911.1 |

% Binding of Llama a-CLL1 clones on U937 detectd with a-His-PE

| % of Llama anti-CLL1 clone binding on U937 detectd with a-His-PE | | | | | | | | |
|---|---|---|---|---|---|---|---|---|
| ng/ml | 1H1 | STD | 1G6 | STD | 2F5 | STD | 2H3 | STD |
| 3000 | 71.0% | 2.6% | 88.9% | 0.8% | 86.4% | 1.3% | 88.7% | 0.5% |
| 1000 | 35.7% | 1.1% | 88.6% | 0.5% | 85.9% | 0.9% | 90.3% | 0.5% |
| 333.3 | 10.4% | 0.7% | 88.2% | 0.5% | 86.7% | 1.0% | 89.9% | 1.1% |
| 111.1 | 2.1% | 0.2% | 87.7% | 0.9% | 86.0% | 0.3% | 89.4% | 0.5% |
| 37.0 | 0.9% | 0.0% | 83.1% | 4.9% | 83.1% | 0.8% | 89.0% | 0.4% |
| 12.3 | 0.7% | 0.0% | 56.7% | 5.1% | 59.3% | 1.7% | 70.5% | 0.4% |
| 4.1 | 0.7% | 0.1% | 26.8% | 2.8% | 24.2% | 0.8% | 33.5% | 0.5% |
| 1.4 | 0.6% | 0.1% | 6.0% | 0.7% | 4.6% | 0.6% | 6.2% | 0.4% |

FIG. 3B

| Backup a-CLL1 clones | Plot 9 (FL2-A/SSC-A) | | |
| --- | --- | --- | --- |
| | R3 | | |
| | Count | % of This I | Mean FL2-A |
| A11 U937 unstain _2-8-2018 | 3 | 0.0% | 4,885.0 |
| H07 U937 + a-Myc + a-mIgG-PE | 55 | 0.6% | 64,740.2 |
| H01 U937 + 1A10 + a-Myc + a-mIgG-PE | 8,430 | 99.5% | 62,003.7 |
| H02 U937 + 1B1 + a-Myc + a-mIgG-PE | 9,744 | 99.6% | 64,111.6 |
| H03 U937 + 1C6 + a-Myc + a-mIgG-PE | 591 | 6.0% | 12,334.3 |
| H04 U937 + 2C8 + a-Myc + a-mIgG-PE | 9,660 | 99.4% | 52,398.2 |
| H05 U937 + 1D2 + a-Myc + a-mIgG-PE | 9,659 | 99.4% | 57,089.7 |
| H06 U937 + 2F5 + a-Myc + a-mIgG-PE | 9,722 | 99.7% | 53,152.7 |

FIG. 4B

|   | 1 | 2 | 3 | 4 | 5 | 6 | 7 |
|---|---|---|---|---|---|---|---|
| A | 1B1/1B1* | 1B1/1G6* | 1B1/2F5* | 1B1/1A10* | 1B1/2H3* | 1B1/1H1* | 1B1/2C2* |
| B | 1G6/1B1* | 1G6/1G6* | 1G6/2F5* | 1G6/1A10* | 1G6/2H3* | 1G6/1H1* | 1G6/2C2* |
| C | 2F5/1B1* | 2F5/1G6* | 2F5/2F5* | 2F5/1A10* | 2F5/2H3* | 2F5/1H1* | 2F5/2C2* |
| D | 1A10/1B1* | 1A10/1G6* | 1A10/2F5* | 1A10/1A10* | 1A10/2H3* | 1A10/1H1* | 1A10/2C2* |
| E | 2H3/1B1* | 2H3/1G6* | 2H3/2F5* | 2H3/1A10* | 2H3/2H3* | 2H3/1H1* | 2H3/2C2* |
| F | 1H1/1B1* | 1H1/1G6* | 1H1/2F5* | 1H1/1A10* | 1H1/2H3* | 1H1/1H1* | 1H1/2C2* |
| G | 2C2/1B1* | 2C2/1G6* | 2C2/2F5* | 2C2/1A10* | 2C2/2H3* | 2C2/1H1* | 2C2/2C2* |

\* Biotinylated protein

FIG. 7A

Unlabeled 1B1 first on CLEC12a coated plate

Unlabeled 1H1 first on CLEC12a coated plate coated with clec12a, then 2H3, anti-myc, HRP-anti-mIgG

| 4-P Fit: y = (A - D)/( 1 + (x/C)^B ) + D: | A | B | C | D | R^2 |
|---|---|---|---|---|---|
| ○ Plot#1 (Clec Sino-2H3: Concentration vs Values) | 0.0547 | 1.98 | 66.1 | 0.332 | 0.999 |
| □ Plot#2 (clec AB-2H3: Concentration vs Values) | 0.0503 | 1.61 | 4.5e+06 | -129 | 0.131 |

Weighting: Fixed coated with clec12a, then 2H3, anti-myc, HRP-anti-mIgG

| 4-P Fit: y = (A - D)/( 1 + (x/C)^B ) + D: | A | B | C | D | R^2 |
|---|---|---|---|---|---|
| ○ Plot#1 (Clec Sino-2H3: Concentration vs Values) | 0.0625 | 1.92 | 62.5 | 0.498 | 0.999 |
| □ Plot#2 (clec AB-2H3: Concentration vs Values) | 0.0555 | 24.3 | 1.71e+03 | 0.054 | 0.0445 |

Weighting: Fixed

| 4-P Fit: y = (A - D)/( 1 + (x/C)^B ) + D: | A | B | C | D | R^2 |
|---|---|---|---|---|---|
| ○ Plot#1 (clec12-#330: Concentration vs Values) | 0.0557 | 1.01 | 5.11 | 1.51 | 1 |
| □ Plot#2 (clec12 AB-#330: Concentration vs Values) | 0.0532 | 0.978 | 1.75e+03 | 1.2 | 1 |

Weighting: Fixed

SINGLE DOMAIN ANTIBODIES AGAINST CLL-1

CROSS REFERENCE TO RELATED APPLICATIONS

The present application claims the benefit of U.S. provisional application No. 62/774,025 filed on Nov. 30, 2018, and of U.S. provisional application No. 62/780,092 filed Dec. 14, 2018, the contents of both of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Jan. 7, 2020, is named 2012106-0088_SL.txt and is 59,243 bytes in size.

BACKGROUND

C type Lectin Like molecule 1 (CLL-1, also known as MICL, and Clec12A) is expressed on acute myeloid leukemia (AML) cells, and on cancer stem cells (CSCs), which are cells that can give rise to additional cancer cells. AML remains a major therapeutic challenge and an unmet need in hematologic oncology. AML is a disease resulting in uncontrollable accumulation of immature myeloid blasts in the bone marrow and peripheral blood, and the disease has multiple subtypes that contribute to the challenge in developing an encompassing targeted therapy. Although there is an increased understanding in the molecular genetics of the disease, there have been relatively few novel therapies approved for AML. Accordingly, there remains a need for novel therapeutics for AML, such as therapeutics that target CLL-1.

SUMMARY OF INVENTION

In one aspect, the present disclosure provides, among other things, antibodies, or antigen binding fragments thereof, that bind (e.g., selectively bind) CLL-1, compositions useful for binding CLL-1, and methods for treating disease comprising administration of such antibodies, or antigen binding fragments thereof. In some embodiments, the present disclosure provides an antibody, or antigen binding fragment thereof, comprising a VHH described herein. In some embodiments, the present disclosure provides an antibody, or antigen-binding fragment thereof, that binds (e.g., selectively binds) CLL-1, comprising or consisting of a VHH having the amino acid sequence of any one of SEQ ID Nos:3-25, or a fragment thereof. In some embodiments, the present disclosure provides an antibody, or antigen-binding fragment thereof, that binds (e.g., selectively binds) CLL-1, comprising or consisting of a VHH having a portion (e.g., a CLL-1 binding portion) of the amino acid sequence of any one of SEQ ID Nos:3-25, wherein the portion lacks one or more of the C-terminal amino acids TSGPGGQGAEQKLISEEDLGAHHHHHHT-FIGAS (SEQ ID NO: 30) depicted in each of SEQ ID Nos:3-25. In some embodiments, the present disclosure provides an antibody, or antigen-binding fragment thereof, that binds (e.g., selectively binds) CLL-1, comprising or consisting of a VHH having a portion (e.g., a CLL-1 binding portion) of the amino acid sequence of any one of SEQ ID Nos:3-25, wherein the portion lacks all of the C-terminal amino acids TSGPGGQGAEQKLISEEDLGAHHHHHHT-FIGAS (SEQ ID NO: 30) depicted in each of SEQ ID Nos:3-25. In some embodiments, the present disclosure provides an antibody, or antigen-binding fragment thereof, that binds (e.g., selectively binds) CLL-1, comprising or consisting of a VHH having a portion (e.g., a CLL-1 binding portion) of the amino acid sequence of any one of SEQ ID Nos:3-25, wherein the portion lacks one or more of the C-terminal amino acids TSGPGGQGAEQKLISEEDL-GAHHHHHHTFIGAS (SEQ ID NO: 30) depicted in each of SEQ ID Nos:3-25, and wherein the portion lacks one or more (e.g., 1, 2, 3, 4, 5, or more), additional amino acids. In some embodiments, the present disclosure provides an antibody, or antigen-binding fragment thereof, that binds (e.g., selectively binds) CLL-1, comprising or consisting of a VHH having a portion (e.g., a CLL-1 binding portion) of the amino acid sequence of any one of SEQ ID Nos:3-25, wherein the portion lacks all of the C-terminal amino acids TSGPGGQGAEQKLISEEDLGAHHHHHHTFIGAS (SEQ ID NO: 30) depicted in each of SEQ ID Nos:3-25, and wherein the portion lacks one or more (e.g., 1, 2, 3, 4, 5, or more), additional amino acids. In some embodiments, the present disclosure provides an antibody, or antigen-binding fragment thereof, that binds (e.g., selectively binds) CLL-1, comprising or consisting of a VHH having an amino acid sequence that is at least 85%, 90%, 91%, 92%, 93%, 94%, 95%, 96%, 97%, 98%, 99%, or 100% identical to a portion of the amino acid sequence of any one of SEQ ID Nos:3-25, wherein the portion lacks one or more of the C-terminal amino acids TSGPGGQGAEQKLISEEDLGAHHHHHHT-FIGAS (SEQ ID NO: 30) depicted in each of SEQ ID Nos:3-25. In some embodiments, the present disclosure provides an antibody, or antigen-binding fragment thereof, that binds (e.g., selectively binds) CLL-1, comprising or consisting of a VHH having an amino acid sequence that is at least 85%, 90%, 91%, 92%, 93%, 94%, 95%, 96%, 97%, 98%, 99%, or 100% identical to a portion of the amino acid sequence of any one of SEQ ID Nos:3-25, wherein the portion lacks all of the C-terminal amino acids TSGPGGQ-GAEQKLISEEDLGAHHHHHHIIGAS (SEQ ID NO: 30) depicted in each of SEQ ID Nos:3-25. In some embodiments, the present disclosure provides an antibody, or antigen-binding fragment thereof, that binds (e.g., selectively binds) CLL-1, comprising or consisting of a VHH having an amino acid sequence that is at least 85%, 90%, 91%, 92%, 93%, 94%, 95%, 96%, 97%, 98%, 99%, or 100% identical to a portion of the amino acid sequence of any one of SEQ ID Nos:3-25, wherein the portion lacks one or more of the C-terminal amino acids TSGPGGQGAEQKLISEEDL-GAHHHHHHIIGAS (SEQ ID NO: 30) depicted in each of SEQ ID Nos:3-25, and wherein the portion lacks one or more (e.g., 1, 2, 3, 4, 5, or more), additional amino acids. In some embodiments, the present disclosure provides an antibody, or antigen-binding fragment thereof, that binds (e.g., selectively binds) CLL-1, comprising or consisting of a VHH having an amino acid sequence that is at least 85%, 90%, 91%, 92%, 93%, 94%, 95%, 96%, 97%, 98%, 99%, or 100% identical to a portion of the amino acid sequence of any one of SEQ ID Nos:3-25, wherein the portion lacks all of the C-terminal amino acids TSGPGGQGAEQKLISEED-LGAHHHHHHTFIGAS (SEQ ID NO: 30) depicted in each of SEQ ID Nos:3-25, and wherein the portion lacks one or more (e.g., 1, 2, 3, 4, 5, or more), additional amino acids. In some embodiments, the present disclosure provides an antibody, or antigen-binding fragment thereof, that binds (e.g., selectively binds) CLL-1, comprising or consisting of a VHH comprising at least one CDR (e.g., CDR1, CDR2, and/or CDR3) depicted in any one of SEQ ID Nos:3-25. In some embodiments, the present disclosure provides an antibody, or antigen-binding fragment thereof, that binds (e.g., selectively binds) CLL-1, comprising or consisting of a VHH comprising at least one CDR that is at least 85%, 90%, 91%, 92%, 93%, 94%, 95%, 96%, 97%, 98%, 99%, or 100% identical to a CDR (e.g., CDR1, CDR2, and/or CDR3) depicted in any one of SEQ ID Nos:3-25. In some embodiments, the present disclosure provides an antibody, or antigen-binding fragment thereof, that binds (e.g., selectively binds) CLL-1, comprising or consisting of a VHH comprising CDR1, CDR2, and/or CDR3 of any one of Groups 1-13 depicted in Table 1A and/or Table 1B. In some embodiments, the present disclosure provides an antibody, or antigen-binding fragment thereof, that binds (e.g., selectively binds) CLL-1, comprising or consisting of a VHH comprising (i) CDR1 and CDR2; (ii) CDR2 and CDR3; (iii) CDR1 and CDR3; or (iv) CDR1, CDR2, and CDR3 of any one of Groups 1-13 depicted in Table 1A and/or Table 1B. In some embodiments, the present disclosure provides an antibody, or antigen-binding fragment thereof, that binds (e.g., selectively binds) CLL-1, comprising or consisting of a VHH comprising CDR1, CDR2, and CDR3 of Group 1; CDR1, CDR2, and CDR3 of Group 2; CDR1, CDR2, and CDR3 of Group 3; CDR1, CDR2, and CDR3 of Group 4; CDR1, CDR2, and CDR3 of Group 5; CDR1, CDR2, and CDR3 of Group 6; CDR1, CDR2, and CDR3 of Group 7; CDR1, CDR2, and CDR3 of Group 8; CDR1, CDR2, and CDR3 of Group 9; CDR1, CDR2, and CDR3 of Group 10; CDR1, CDR2, and CDR3 of Group 11; CDR1, CDR2, and CDR3 of Group 12; or CDR1, CDR2, and CDR3 of Group 13 depicted in Table 1A and/or Table 1B.

In some embodiments, the present disclosure provides an antibody or antigen-binding fragment thereof that binds (e.g., selectively binds) to CLL-1 at, e.g., an epitope consisting of or comprising the last 50, 40, or 30 C-terminal amino acids of SEQ ID NO: 28. In some embodiments, the present disclosure provides an antibody or antigen-binding fragment thereof that binds (e.g., selectively binds) to CLL-1 at, e.g., an epitope consisting of or comprising amino acids 243 to 275 of SEQ ID NO: 28. In some embodiments, the present disclosure provides an antibody or antigen-binding fragment thereof that binds (e.g., selectively binds) to CLL-1 at, e.g., an epitope consisting of or comprising amino acids 248 to 262 of SEQ ID NO: 28. In some embodiments, the present disclosure provides an antibody or antigen-binding fragment thereof that binds (e.g., selectively binds) to CLL-1 at, e.g., an epitope consisting of or comprising amino acids 251 to 260 of SEQ ID NO: 28. In some embodiments, the present disclosure provides an antibody or antigen-binding fragment thereof that binds (e.g., selectively binds) to CLL-1 and does not compete for binding with SC02-357 antibody (e.g., consisting or comprising SEQ ID NO:26). In some embodiments, the present disclosure provides an antibody or antigen-binding fragment thereof that binds (e.g., selectively binds) to CLL-1 and competes for binding to CLL-1 with an antibody or antigen binding fragment described herein (e.g., comprising or consisting of a sequence selected from the group consisting of SEQ ID NO: 3 to SEQ ID NO: 25).

In some embodiments, the present disclosure provides a nucleic acid sequence encoding an antibody or antigen-binding fragment thereof described herein. In some embodiments, the present disclosure provides a vector comprising a nucleic acid sequence encoding an antibody or antigen-binding fragment thereof described herein. In some embodiments, the present disclosure provides a host cell comprising a nucleic acid sequence encoding an antibody or antigen-binding fragment thereof described herein. In some embodiments, the present disclosure provides a host cell comprising a vector comprising a nucleic acid sequence encoding an antibody or antigen-binding fragment thereof described herein. In some embodiments, the present disclosure provides a method of producing an antibody, or antigen-binding fragment thereof, comprising culturing a host cell, e.g., a host cell comprising a nucleic acid encoding an antibody or antigen-binding fragment thereof described herein, under conditions suitable for expression of an antibody or antigen-binding fragment thereof. In some embodiments, the present disclosure provides a method of treating a CLL-1 associated disease or disorder, the method comprising administering to a subject in need thereof an effective amount of an antibody, or antigen-binding fragment thereof, described herein, e.g., administering a composition (e.g., a pharmaceutical composition) comprising an effective amount of an antibody, or antigen-binding fragment thereof, described herein.

Other features, objects, and advantages of the present disclosure are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

Definitions

A or An: The articles "a" and "an" are used herein to refer to one or to more than one (i.e., to at least one) of the grammatical object of the article. By way of example, "an element" means one element or more than one element.

Affinity: As used herein, the term "affinity" refers to the characteristics of a binding interaction between an antigen binding moiety (e.g., a single domain antibody described herein) and an antigen target (e.g., CLL-1) and that indicates the strength of the binding interaction. In some embodiments, the measure of affinity is expressed as a dissociation constant ($K_D$). In some embodiments, an antigen binding moiety has a high affinity for an antigen target (e.g., a $K_D$ of less than about $10^{-7}$ M, less than about $10^{-8}$ M, or less than about $10^{-9}$ M).

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding domains or fragments of antibodies (e.g., single domain antibodies, single chain antibodies, Fab, F(ab')2, Fd, Fv, dAb fragments) as well as complete antibodies, e.g., intact immunoglobulins of types IgA, IgG, IgE, IgD, IgM (as well as subtypes thereof). The light chains of the immunoglobulin can be of types kappa or lambda.

Antigen target: As used herein, an "antigen target" is any molecule specifically bound by an antigen binding moiety of an antibody described herein. In some embodiments, an antigen target is CLL-1.

Constant region: As used herein, the term "constant region" refers to a polypeptide that corresponds to, or is derived from, one or more constant region immunoglobulin domains of an antibody. A constant region can include any or all of the following immunoglobulin domains: a CH1 domain, a hinge region, a CH2 domain, a CH3 domain (derived from an IgA, IgD, IgG, IgE, or IgM), and a CH4 domain (derived from an IgE or IgM).

Fc region: As used herein, the term "Fc region" refers to a dimer of two "Fc polypeptides", each "Fc polypeptide" comprising the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or all of the flexible hinge N-terminal to these domains. For IgG, "Fc polypeptide" comprises immunoglobulin domains Cgamma2 (C$\gamma$2) and Cgamma3 (C$\gamma$3) and the lower part of the hinge between Cgamma1 (C$\gamma$1) and C$\gamma$2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, VA). For IgA, Fc polypeptide comprises immunoglobulin domains Calpha2 (C$\alpha$2) and Calpha3 (C$\alpha$3) and the lower part of the hinge between Calpha1 (C$\alpha$1) and C$\alpha$2. An Fc region can be synthetic, recombinant, or generated from natural sources such as IVIG.

Identity: As used herein, the term "identity" refers to the overall relatedness between nucleic acid molecules (e.g., DNA molecules and/or RNA molecules) and/or between polypeptides. In some embodiments, nucleic acids or polypeptides are considered to be "substantially identical" to one another if their sequences are at least 25%, 30%, 35%, 40%, 45%, 50%, 55%, 60%, 65%, 70%, 75%, 80%, 85%, 90%, 95%, 96%, 97%, 98%, or 99% identical. Calculation of the percent identity of two nucleic acid or polypeptide sequences, for example, can be performed by aligning the two sequences for optimal comparison purposes (e.g., gaps can be introduced in one or both of a first and a second sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 75%, at least 80%, at least 85%, at least 90%, at least 95%, at least 96%, at least 97%, at least 98%, at least 99%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller, 1989, which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Immunoglobulin single variable domain: The term "immunoglobulin single variable domain" or "single variable domain", as used herein, means an immunoglobulin variable domain which is capable of specifically binding to an epitope of the antigen without pairing with an additional variable immunoglobulin domain. One example of an immunoglobulin single variable domain in the meaning of the present disclosure is "domain antibody", such as the immunoglobulin single variable domains VH and VL (VH domains and VL domains). Another example of an immunoglobulin single variable domain is "VHH domain" (or simply "VHH") from camelids, as described herein.

Immunoglobulin variable domain: The term "immunoglobulin variable domain" or "variable domain", as used herein, means an immunoglobulin domain that is or includes four "framework regions" (referred to in the art and herein as "framework region 1" or "FR1"; as "framework region 2" or "FR2"; as "framework region 3" or "FR3"; and as "framework region 4" or "FR4", respectively); which framework regions are interrupted by three "complementarity determining regions" or "CDRs" (referred to in the art and herein as "complementarity determining region 1" or "CDR1"; as "complementarity determining region 2" or "CDR2"; and as "complementarity determining region 3" or "CDR3", respectively). In some embodiments, the general structure or sequence of an immunoglobulin variable domain can be indicated as follows: FR1-CDR1-FR2-CDR2-FR3-CDR3-FR4.

$K_a$: As used herein, "$K_a$" refers to an association rate of a particular antigen binding moiety and an antigen target to form an antigen binding moiety/antigen target complex.

$K_d$: As used herein, "$K_d$" refers to a dissociation rate of a particular antigen binding moiety/antigen target complex.

$K_D$: As used herein, "$K_D$" refers to a dissociation constant, which is obtained from the ratio of $K_d$ to $K_a$ (i.e., $K_d/K_a$) and is expressed as a molar concentration (M). $K_D$ values can be determined using methods well established in the art, e.g., by using surface plasmon resonance, or using a biosensor system such as a Biacore® system.

Selective binding: As used herein, "selective binding", "selectively binds" "specific binding", or "specifically binds" refers, with respect to an antigen binding moiety and an antigen target, preferential association of an antigen binding moiety to an antigen target and not to an entity that is not the antigen target. A certain degree of non-specific binding may occur between an antigen binding moiety and a non-target. In some embodiments, an antigen binding moiety selectively binds an antigen target if binding between the antigen binding moiety and the antigen target is greater than 2-fold, greater than 5-fold, greater than 10-fold, or greater than 100-fold as compared with binding of the antigen binding moiety and a non-target. In some embodiments, an antigen binding moiety selectively binds an antigen target if the binding affinity is less than about $10^{-5}$ M, less than about $10^{-6}$ M, less than about $10^{-7}$ M, less than about $10^{-8}$ M, or less than about $10^{-9}$ M.

Subject: The term "subject", as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

Therapeutically effective amount: As used herein, the term "therapeutically effective amount" refers to an amount of an antibody or composition described herein that confers a therapeutic effect on a treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of an antibody or composition effective to treat, ameliorate, or prevent a particular disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount can be administered in a dosing regimen that may comprise multiple unit doses. For any particular antibody or composition, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific therapeutic molecule employed; the duration of the treatment; and like factors as is well known in the medical arts.

Treatment: As used herein, the term "treatment" (also "treat" or "treating") refers to any administration of an antibody or composition described herein that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

BRIEF DESCRIPTION OF DRAWINGS

FIGS. 3A-3C show determination of EC50s of certain VHH clones.

FIGS. 4A and 4B show U937 cell binding by certain VHH clones.

FIGS. 7A-7D shows determination of distinct or similar epitopes among certain VHH clones.

FIG. 11A discloses SEQ ID NO: 89 and FIG. 11B discloses SEQ ID NO: 89.

DETAILED DESCRIPTION OF INVENTION

Figure 1:
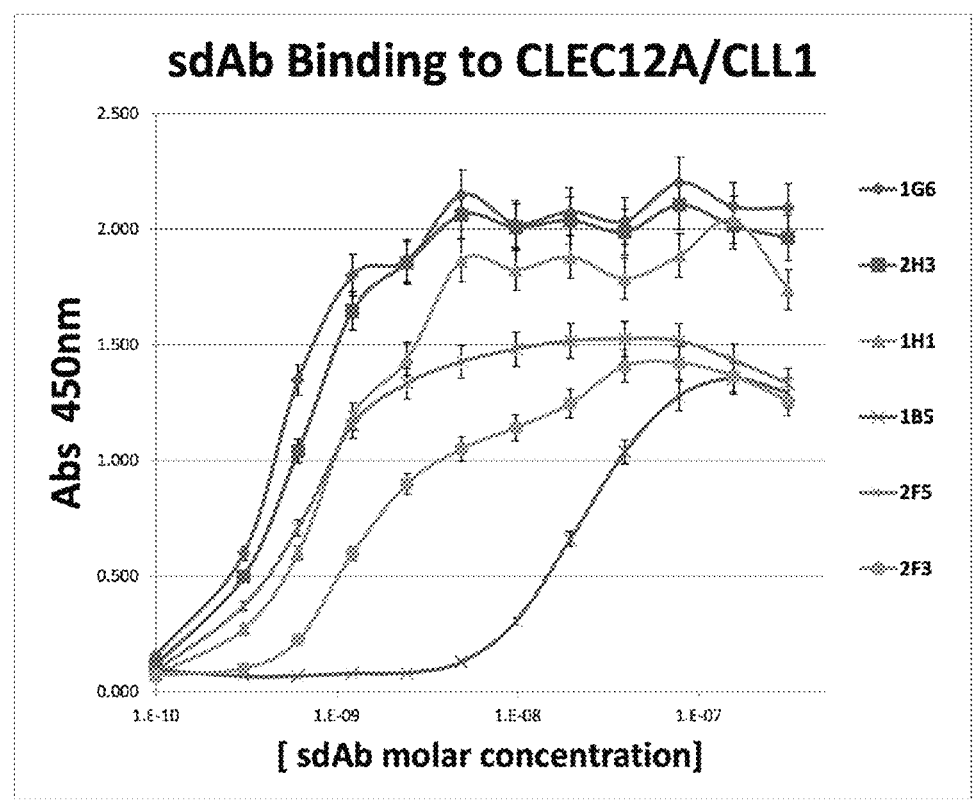
FIG. 1 shows binding of certain VHH clones to CLEC12A.

The present disclosure is based, in part, on the discovery of single domain antibodies that selectively bind to CLL-1/CLEC12A. The disclosure also relates to nucleic acids encoding said antibodies, or antigen-binding fragments thereof, cells comprising such nucleic acids, and methods of use.

Single Domain Antibodies

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art known, or any future single domain antibodies. Single domain antibodies may be derived from any species including, but not limited to mouse, human, camel, llama, goat, rabbit, bovine. According to one aspect of the disclosure, a single domain antibody as used herein is a naturally occurring single domain antibody known as heavy chain antibody devoid of light chains. Such single domain antibodies are disclosed in, e.g., WO 94/04678. Such variable domains derived from a heavy chain antibody naturally devoid of light chain is referred to herein as a "VHH" or "nanobody". Such a VHH can be derived from antibodies raised in Camelidae species, for example in camel, dromedary, llama, vicuna, alpaca and guanaco. Other species besides Camelidae may produce heavy chain antibodies naturally devoid of light chain; such VHHs are within the scope of the disclosure.

The amino acid residues of VHH domains from Camelids are numbered according to the general numbering for VH domains given by Kabat et al., "Sequence of proteins of immunological interest", US Public Health Services, NIH (Bethesda, MD), Publication No 91-3242 (1991); see also Riechmann et al., J. Immunol. Methods 231:25-38 (1999). According to this numbering, FR1 comprises the amino acid residues at positions 1-30, CDR1 comprises the amino acid residues at positions 31-35, FR2 comprises the amino acids at positions 36-49, CDR2 comprises the amino acid residues at positions 50-65, FR3 comprises the amino acid residues at positions 66-94, CDR3 comprises the amino acid residues at positions 95-102, and FR4 comprises the amino acid residues at positions 103-113.

It should be noted, however (as is well known in the art for VH domains and for VHH domains), that the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence.

Alternative methods for numbering the amino acid residues of VH domains, which methods can also be applied in an analogous manner to VHH domains, are known in the art. However, in the present disclosure, claims and figures, the numbering according to Kabat and applied to VHH domains as described above will be followed, unless indicated otherwise.

In some embodiments, the disclosure provides a CLL-1 binding antibody that is or includes a VHH having the amino acid sequence of any one of SEQ ID Nos:3-25, or a fragment thereof (e.g., a CLL-1 binding fragment thereof). As indicated in the listing of sequences provided herein, each of SEQ ID Nos:3-25 includes VHH amino acids at the N-terminus, and the following amino acids at the C-terminus: (i) a linker of 9 amino acids (TSGPGGQGA (SEQ ID NO: 31)), (ii) a myc-tag (EQKLISEEDL (SEQ ID NO: 32)), (iii) a linker of 2 amino acids (GA), (iv) a hexa-histidine tag (HHHHHH (SEQ ID NO: 33)), and (v) an additional 3 amino acids (GAS). In some embodiments, the disclosure provides an antibody that binds (e.g., selectively binds) CLL-1, that is or includes a VHH having a portion (e.g., a CLL-1 binding portion) of the amino acid sequence of any one of SEQ ID Nos:3-25, wherein the portion lacks one or more of (i)-(v) (and/or lacks a portion of one or more of (i)-(v)). In some embodiments, the disclosure provides an antibody that binds (e.g., selectively binds) CLL-1, that is or includes a VHH having a portion (e.g., a CLL-1 binding portion) of the amino acid sequence of any one of SEQ ID Nos:3-25, wherein the portion lacks one or more of the C-terminal amino acids TSGPGGQGAEQKLISEEDL-GAHHHIIHHHGAS (SEQ ID NO: 30) depicted in each of SEQ ID Nos:3-25. In some embodiments, the disclosure provides an antibody that binds (e.g., selectively binds) CLL-1, that is or includes a VHH having a portion (e.g., a CLL-1 binding portion) of the amino acid sequence of any one of SEQ ID Nos:3-25, wherein the portion lacks all of the C-terminal amino acids TSGPGGQGAEQKLISEEDL-GAHHHHHHTFIGAS (SEQ ID NO: 30) depicted in each of SEQ ID Nos:3-25.

In some embodiments, the disclosure provides an antibody that binds (e.g., selectively binds) CLL-1, that is or includes a VHH having a portion (e.g., a CLL-1 binding portion) of the amino acid sequence of any one of SEQ ID Nos:3-25, wherein the portion lacks one or more of (i)-(v) (and/or lacks a portion of one or more of (i)-(v)), and wherein the portion lacks one or more (e.g., 1, 2, 3, 4, 5, or more), additional amino acids (i.e., other than an amino acid included in (i)-(v)). In some embodiments, the disclosure provides an antibody that binds (e.g., selectively binds) CLL-1, that is or includes a VHH having a portion (e.g., a CLL-1 binding portion) of the amino acid sequence of any one of SEQ ID Nos:3-25, wherein the portion lacks one or more of the C-terminal amino acids TSGPGGQGAEQKLI-SEEDLGAHHHHHHIIGAS (SEQ ID NO: 30) depicted in each of SEQ ID Nos:3-25, and wherein the portion lacks one or more (e.g., 1, 2, 3, 4, 5, or more), additional amino acids. In some embodiments, the disclosure provides an antibody that binds (e.g., selectively binds) CLL-1, that is or includes a VHH having a portion (e.g., a CLL-1 binding portion) of the amino acid sequence of any one of SEQ ID Nos:3-25, wherein the portion lacks all of the C-terminal amino acids TSGPGGQGAEQKLISEEDLGAHHHHHHGAS (SEQ ID NO: 30) depicted in each of SEQ ID Nos:3-25, and wherein the portion lacks one or more (e.g., 1, 2, 3, 4, 5, or more), additional amino acids.

In some embodiments, the disclosure provides an antibody that binds (e.g., selectively binds) CLL-1, that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:3-25, wherein the portion lacks one or more of (i)-(v) (and/or lacks a portion of one or more of (i)-(v)). In some embodiments, the disclosure provides an antibody that binds (e.g., selectively binds) CLL-1, that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:3-25, wherein the portion lacks one or more of the C-terminal amino acids TSGPGGQGAEQKLISEEDLGAHHHHHHII-GAS (SEQ ID NO: 30) depicted in each of SEQ ID Nos:3-25. In some embodiments, the disclosure provides an antibody that binds (e.g., selectively binds) CLL-1, that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:3-25, wherein the portion lacks all of the C-terminal amino acids TSGPGGQGAEQKLISEEDLGA-HIIHIHHGAS (SEQ ID NO: 30) depicted in each of SEQ ID Nos:3-25.

In some embodiments, the disclosure provides an antibody that binds (e.g., selectively binds) CLL-1, that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:3-25, wherein the portion lacks one or more of (i)-(v) (and/or lacks a portion of one or more of (i)-(v)), and wherein the portion lacks one or more (e.g., 1, 2, 3, 4, 5, or more), additional amino acids (i.e., other than an amino acid included in (i)-(v)). In some embodiments, the disclosure provides an antibody that binds (e.g., selectively binds) CLL-1, that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:3-25, wherein the portion lacks one or more of the C-terminal amino acids TSGPGGQ-GAEQKLISEEDLGAHHHHHHHGAS (SEQ ID NO: 30) depicted in each of SEQ ID Nos:3-25, and wherein the portion lacks one or more (e.g., 1, 2, 3, 4, 5, or more), additional amino acids. In some embodiments, the disclosure provides an antibody that binds (e.g., selectively binds) CLL-1, that is or includes a VHH having an amino acid sequence that is at least 85%, 90%, 91%, 92%, 93%, 94%, 95%, 96%, 97%, 98%, 99%, or 100% identical to a portion (e.g., a CLL-1 binding portion) of the amino acid sequence of any one of SEQ ID Nos:3-25, wherein the portion lacks all of the C-terminal amino acids TSGPGGQGAEQKLI-SEEDLGAIHHHHHHMGAS (SEQ ID NO: 30) depicted in each of SEQ ID Nos:3-25, and wherein the portion lacks one or more (e.g., 1, 2, 3, 4, 5, or more), additional amino acids.

In some embodiments, the disclosure provides an antibody that binds (e.g., selectively binds) CLL-1, that is or includes a VHH comprising at least one CDR (e.g., CDR1, CDR2, and/or CDR3) depicted in any one of SEQ ID Nos:3-25. In some embodiments, the disclosure provides an antibody that binds (e.g., selectively binds) CLL-1, that is or includes a VHH comprising a portion of at least one CDR (e.g., CDR1, CDR2, and/or CDR3) depicted in any one of SEQ ID Nos:3-25, wherein the portion lacks 1, 2, 3, 4, 5, or more amino acids of a CDR depicted in any one of SEQ ID Nos:3-25. In some embodiments, the disclosure provides an antibody that binds (e.g., selectively binds) CLL-1, that is or includes a VHH comprising at least one CDR that is at least 85%, 90%, 91%, 92%, 93%, 94%, 95%, 96%, 97%, 98%, 99%, or 100% identical to a CDR (e.g., CDR1, CDR2, and/or CDR3) depicted in any one of SEQ ID Nos:3-25. In some embodiments, the disclosure provides an antibody that binds (e.g., selectively binds) CLL-1, that is or includes a VHH comprising an amino acid sequence that is at least 85%, 90%, 91%, 92%, 93%, 94%, 95%, 96%, 97%, 98%, 99%, or 100% identical to a portion of at least one CDR (e.g., CDR1, CDR2, and/or CDR3) depicted in any one of SEQ ID Nos:3-25, wherein the portion lacks 1, 2, 3, 4, 5, or more amino acids of a CDR depicted in any one of SEQ ID Nos:3-25.

In some embodiments, the disclosure provides an antibody that binds (e.g., selectively binds) CLL-1, that is or includes a VHH comprising CDR1, CDR2, and/or CDR3 of any one of Groups 1-13 depicted in Table 1A and/or Table 1B. In some embodiments, the disclosure provides an antibody that binds (e.g., selectively binds) CLL-1, that is or includes a VHH comprising (i) CDR1 and CDR2; (ii) CDR2 and CDR3; (iii) CDR1 and CDR3; or (iv) CDR1, CDR2, and CDR3 of any one of Groups 1-13 depicted in Table 1A and/or Table 1B (e.g., wherein the CDRs are from one particular Group, or wherein the CDRs are selected from two or more different Groups). In some embodiments, the disclosure provides an antibody that binds (e.g., selectively binds) CLL-1, that is or includes a VHH comprising CDR1, CDR2, and CDR3 of Group 1; CDR1, CDR2, and CDR3 of Group 2; CDR1, CDR2, and CDR3 of Group 3; CDR1, CDR2, and CDR3 of Group 4; CDR1, CDR2, and CDR3 of Group 5; CDR1, CDR2, and CDR3 of Group 6; CDR1, CDR2, and CDR3 of Group 7; CDR1, CDR2, and CDR3 of Group 8; CDR1, CDR2, and CDR3 of Group 9; CDR1, CDR2, and CDR3 of Group 10; CDR1, CDR2, and CDR3 of Group 11; CDR1, CDR2, and CDR3 of Group 12; or CDR1, CDR2, and CDR3 of Group 13, as depicted in Table 1A and/or Table 1B.

TABLE 1A

| Group | SEQ ID NO: | CDR1 | SEQ ID NO: | CDR2 | SEQ ID NO: | CDR3 |
|---|---|---|---|---|---|---|
| 1 | 34 | CAASGSIFAINEI | 47 | VAACASDGNTY | 58 | DANSRGNYY |
| 2 | 35 | CVVSGDTRSI | 47 | VAACASDGNTY | 58 | DANSRGNYY |
| 3 | 36 | CVASGSIRSI | 47 | VAACASDGNTY | 58 | DANSRGNYY |
| 4 | 37 | CAASGFTFNSYA | 48 | WVSDINSGGGSTN | 59 | ATELRGSDYYRGPIREYAY |
| 5 | 38 | CAASGLTFSNYA | 49 | AINWSGGTTD | 60 | AASYRLRITVVVTPDEYHY |
| 6 | 39 | CAASGFAFDDYA | 50 | WVSSISWNGGGTY | 61 | VKLVDSGWYSAYDY |
| 7 | 40 | CVVSGATSNVNA | 51 | LVAAISSGGSTS | 62 | AAQDWATEGYEYDY |
| 8 | 41 | CVVSGTMFSGKD | 52 | VATVSSDGGTD | 63 | HFLWGRHY |
| 9 | 42 | CVASGNDISGSA | 53 | VAVDAPRERPF | 64 | GPSLRTFHGREWYRPPWFTS |
| 10 | 43 | CAASGSIFSINA | 54 | VAVVSRFGETT | 65 | NARIRGNYGSRIDY |
| 11 | 44 | CVVSGNMLDLNT | 55 | LVAALGISTY | 66 | ARDYNFES |
| 12 | 45 | GSDRSINV | 56 | ITSGGTT | 67 | KADTRWGGMY |
| 13 | 46 | GRTIDNGA | 57 | INWSGGAT | 68 | ASRRGVDLRRNSYEYDY |

TABLE 1B

CDRs as identified based on IMGT numbering and ANARCI software (http://opig.stats.ox.ac.uk/webapps/sabdab-sabpred/ANARCI.php)

| Group | SEQ ID NO: | CDR1 | SEQ ID NO: | CDR2 | SEQ ID NO: | CDR3 |
|---|---|---|---|---|---|---|
| 1 | 69 | GSIFAINEINL | 80 | CASDGNT | 58 | DANSRGNYY |
| 2 | 70 | GDTRSINL | 80 | CASDGNT | 58 | DANSRGNYY |

TABLE 1B-continued

CDRs as identified based on IMGT numbering and ANARCI software
(http://opiq.stats.ox.ac.uk/webapps/sabdab-sabpred/ANARCI.php)

| Group | SEQ ID NO: | CDR1 | SEQ ID NO: | CDR2 | SEQ ID NO: | CDR3 |
|---|---|---|---|---|---|---|
| 3 | 71 | GSIRSINV | 80 | CASDGNT | 58 | DANSRGNYY |
| 4 | 72 | GFTFNSYA | 81 | INSGGGST | 59 | ATELRGSDYYRGPIREYAY |
| 5 | 73 | GLTFSNYA | 82 | INWSGGTT | 60 | AASYRLRITVVVTPDEYHY |
| 6 | 74 | GFAFDDYA | 83 | ISWNGGGT | 61 | VKLVDSGWYSAYDY |
| 7 | 75 | GATSNVNA | 84 | ISSGGST | 62 | AAQDWATEGYEYDY |
| 8 | 76 | GTMFSGKD | 85 | VSSDGGT | 63 | HFLWGRHY |
| 9 | 77 | GNDISGSA | 86 | VDAPRERP | 64 | GPSLRTFHGREWYRPPWFTS |
| 10 | 78 | GSIFSINA | 87 | VSRFGET | 65 | NARIRGNYGSRIDY |
| 11 | 79 | GNMLDLNT | 88 | LGIST | 66 | ARDYNFES |
| 12 | 45 | GSDRSINV | 56 | ITSGGTT | 67 | KADTRWGGMY |
| 13 | 46 | GRTIDNGA | 57 | INWSGGAT | 68 | ASRRGVDLRRNSYEYDY |

In some embodiments, the present disclosure provides an antibody or antigen-binding fragment thereof that binds (e.g., selectively binds) to CLL-1 at, e.g., an epitope in the last 50, 40, or 30 amino acids of SEQ ID NO: 28. In some embodiments, the present disclosure provides an antibody or antigen-binding fragment thereof that binds (e.g., selectively binds) to CLL-1 at, e.g., an epitope within amino acids 243 to 275 of SEQ ID NO: 28. In some embodiments, the present disclosure provides an antibody or antigen-binding fragment thereof that binds (e.g., selectively binds) to CLL-1 at, e.g., an epitope within amino acids 248 to 262 of SEQ ID NO: 28. In some embodiments, the present disclosure provides an antibody or antigen-binding fragment thereof that binds (e.g., selectively binds) to CLL-1 at, e.g., an epitope within amino acids 251 to 260 of SEQ ID NO: 28. In some embodiments, the present disclosure provides an antibody or antigen-binding fragment thereof that binds (e.g., selectively binds) to CLL-1 and does not compete for binding with SC02-357. In some embodiments, the present disclosure provides an antibody or antigen-binding fragment thereof that binds (e.g., selectively binds) to CLL-1 and that competes for binding to CLL-1 with an antibody or antigen binding fragment described herein (e.g., comprising a sequence selected from the group consisting of SEQ ID NO: 3 to SEQ ID NO: 25).

As will be understood by those of skill in the art, any such CDR sequence may be readily combined, e.g., using molecular biology techniques, with any other polypeptide (e.g., antibody) sequences or domains provided herein or otherwise known in the art, including any framework regions, CDRs, or constant domains, or portions thereof as disclosed herein or otherwise known in the art, as may be present in an antibody or binding molecule of any format as disclosed herein or otherwise known in the art.

Antibodies or fragments can be produced by any method known in the art for synthesizing antibodies (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324;

WO 98/46645). Chimeric antibodies can be produced using methods described in, e.g., Morrison, 1985, Science 229: 1202, and humanized antibodies by methods described in, e.g., U.S. Pat. No. 6,180,370.

Additional antibodies of compositions and methods described herein are bispecific antibodies and multivalent antibodies, as described in, e.g., Segal et al., J. Immunol. Methods 248:1-6 (2001); and Tutt et al., J. Immunol. 147: 60 (1991).

Fusion Proteins and Conjugates

In some embodiments, the disclosure provides fusion proteins comprising (i) one or more single domain antibodies, or antigen-binding fragments thereof, described herein (e.g., one or more CDRs described herein), and (ii) one or more additional polypeptides. For example, a fusion protein can include one or more single domain antibodies described herein and a constant region or Fc region described herein. In some embodiments, one or more single domain antibodies, or antigen-binding fragments thereof, described herein (e.g., one or more CDRs described herein) can be conjugated noncovalently or covalently, e.g., fused, to an antigen (e.g., an antigen target for a cellular therapeutic, e.g., a CAR-T cell or antibody drug conjugate) as described in, e.g., WO2017/075537, WO2017/075533, WO2018156802, and WO2018156791.

In some embodiments, the disclosure provides a fusion protein comprising one or more VHH as described herein and one or more additional polypeptides. In some embodiments, an additional polypeptide comprises an additional antibody or fragment thereof. Additional antibodies include, e.g., intact IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular ImmunoPharmaceuticals ("SMIPs™"), single chain or Tandem diabodies (TandAb®), VHHs (including but not limited to those described in the present disclosure), Anticalins®, Nanobodies®, minibodies, BiTE®s, ankyrin repeat proteins or DARPINs®, Avimers®, a DART, a TCR-like antibody, Adnectins®, Affilins®, Trans-Bodies®, Affibodies®, a TrimerX®, MicroProteins, Fynomers®, Centyrins®, and a KALBITOR®. Exemplary additional antibodies are listed in Table 4. In some embodiments, an additional antibody targets PD-1, TIM-3, LAG-3, IDO, A2AR, TGFbeta, CD47, or another protein involved in an immunosuppressive pathway.

TABLE 4

| Human Antigen | Antibody (commercial or scientific name) | Cancer indication |
| --- | --- | --- |
| CD2 | Siplizumab | Non-Hodgkin's Lymphoma |
| CD3 | UCHT1 | Peripheral or Cutaneous T-cell |
| CD4 | HuMax-CD4 | Lymphoma |
| CD19 | SAR3419, MEDI-551 | Diffuse Large B-cell Lymphoma |
| CD19 and CD3 or CD22 | Bispecific antibodies such as Blinatumomab, DT2219ARL | Non-Hodgkin's Lymphoma |
| CD20 | Rituximab, Veltuzumab, Tositumomab, Ofatumumab, Ibritumomab, Obinutuzumab, | B cell malignancies (Non-Hodgkin's lymphoma, Chronic lymphocytic leukemia) |
| CD22 (SIGLEC2) | Inotuzumab, tetraxetan, CAT-8015, DCDT2980S, Bectumomab | Chemotherapy-resistant hairy cell leukemia, Hodgkin's lymphoma |
| CD30 | Brentuximab vedotin | |
| CD33 | Gemtuzumab ozogamicin (Mylotarg) | Acute myeloid leukemia |
| CD37 | TRU-016 | Chronic lymphocytic leukemia |
| CD38 | Daratumumab | Multiple myeloma, hematological tumors |
| CD40 | Lucatumumab | Non-Hodgkin's lymphoma |
| CD52 | Alemtuzumab (Campath) | Chronic lymphocytic leukemia |
| CD56 (NCAM1) | Lorvotuzumab | Small Cell Lung Cancer |
| CD66e (CEA) | Labetuzumab | Breast, colon and lung tumors |
| CD70 | SGN-75 | Non-Hodgkin's lymphoma |
| CD74 | Milatuzumab | Non-Hodgkin's lymphoma |
| CD138 (SYND1) | BT062 | Multiple Myeloma |
| CD152 (CTLA-4) | Ipilimumab | Metastatic melanoma |
| CD221 (IGF1R) | AVE1642, IMC-A12, MK-0646, R150, CP 751871 | Glioma, lung, breast, head and neck, prostate and thyroid cancer |
| CD254 (RANKL) | Denosumab | Breast and prostate carcinoma |
| CD261 (TRAILR1) | Mapatumumab | Colon, lung and pancreas tumors and |
| CD262 (TRAILR2) | HGS-ETR2, CS-1008 | haematological malignancies |
| CD326 (Epcam) | Edrecolomab, 17-1A, IGN101, Catumaxomab, Adecatumumab | Colon and rectal cancer, malignant ascites, epithelial tumors (breast, colon, lung) |
| CD309 (VEGFR2) | IM-2C6, CDP791 | Epithelium-derived solid tumors |
| CD319 (SLAMF7) | HuLuc63 | Multiple myeloma |
| CD340 (HER2) | Trastuzumab, Pertuzumab, Ado-trastuzumab emtansine | Breast cancer |
| CAIX (CA9) | cG250 | Renal cell carcinoma |
| EGFR (c-erbB) | Cetuximab, Panitumumab, nimotuzumab and 806 | Solid tumors including glioma, lung, breast, colon, and head and neck tumors |
| EPHA3 (HEK) | KB004, IIIA4 | Lung, kidney and colon tumors, melanoma, glioma and haematological malignancies |
| Episialin | Epitumomab | Epithelial ovarian tumors |
| FAP | Sibrotuzumab and F19 | Colon, breast, lung, pancreas, and head and neck tumors |
| HLA-DR beta | Apolizumab | Chronic lymphocytic leukemia, non-Hodkin's lymphoma |
| FOLR-1 | Farletuzumab | Ovarian tumors |
| 5T4 | Anatumomab | Non-small cell lung cancer |
| GD3/GD2 | 3F8, ch14. 18, KW-2871 | Neuroectodermal and epithelial tumors |
| gpA33 | huA33 | Colorectal carcinoma |
| GPNMB | Glembatumumab | Breast cancer |
| HER3 (ERBB3) | MM-121 | Breast, colon, lung, ovarian, and prostate tumors |
| Integrin αVβ3 | Etaracizumab | Tumor vasculature |
| Integrin α5β1 | Volociximab | Tumor vasculature |
| Lewis-Y antigen | hu3S193, IgN311 | Breast, colon, lung and prostate tumors |
| MET (HGFR) | AMG 102, METMAB, SCH900105 | Breast, ovary and lung tumors |
| Mucin-1/CanAg | Pemtumomab, oregovomab, Cantuzumab | Breast, colon, lung and ovarian tumors |
| PSMA | ADC, J591 | Prostate Cancer |
| Phosphatidylserine | Bavituximab | Solid tumors |
| TAG-72 | Minretumomab | Breast, colon and lung tumors |
| Tenascin | 81C6 | Glioma, breast and prostate tumours |
| VEGF | Bevacizumab | Tumour vasculature |

In some embodiments, an additional polypeptide comprises or consists of all or a portion of a tumor associated antigen (TAA) or tumor specific antigen (TSA). Non-limiting examples of TSA or TAA antigens include differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other tumor antigens include TSP-180, MAGE-4, MAGE-5, MAGE-6, RAGE, NY-ESO, erbB, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3CA 27.29BCAA, CA 195, CA 242, CA-50, CAM43, CD68P1, CO-029, FGF-5, G250, Ga733EpCAM, HTgp-175, M344, MA-50, MG7-Ag, MOV18, NB/70K, NY-CO-1, RCAS1, SDCCAG16, TA-90Mac-2 binding proteincyclophilin C-associated protein, TAAL6, TAG72, TLP, MUC16, IL13Rα2, FRα, VEGFR2, Lewis Y, FAP, EphA2, CEACAM5, EGFR, CA6, CA9, GPNMB, EGP1, FOLR1, endothelial receptor, STEAP1, SLC44A4, Nectin-4, AGS-16, guanalyl cyclase C, MUC-1, CFC1B, integrin alpha 3 chain (of a3b1, a laminin receptor chain), and TPS.

In some embodiments, an additional polypeptide comprises or consists of all or a portion of a tumor antigen selected from CD19, CD20, CD22, CD30, CD72, CD180, CD171 (L1CAM), CD123, CD133, CD138, CD37, CD70, CD79a, CD79b, CD56, CD74, CD166, CD71, CLL-1/CLECK12A, ROR1, Glypican 3 (GPC3), Mesothelin, CD33/IL3Ra, c-Met, PSCA, PSMA, Glycolipid F77, EGFRvIII, GD-2, MY-ESO-1, and MAGE A3.

In some embdoiments, an additional polypeptide comprises or consists of all or a portion of a B cell specific marker selected from CD19, CD20, CD21, CD22, CD23, CD24, CD40, CD72, CD180, ROR1, BCMA, CD79a, and CD79b (see, e.g., LeBien et al., Blood 112:1570-1580 (2008)).

In some embodiments, the disclosure provides antibodies conjugated to a therapeutic moiety, such as a cytotoxin, a biologically active protein (e.g., one or more peptide or one or more cytokine) or a radioisotoperadiotoxin. Such conjugates are referred to herein as "immunococonjugates". Immunoconjugates that include one or more cytotoxins are referred to as "immunotoxins". A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Therapeutic agents that can be conjugated also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to antibodies described herein include duocarmycins, calicheamicins, maytansines and auristatins, and derivatives thereof.

Cytotoxins can be conjugated to antibodies using linker technology available in the art. Examples of linker types that have been used to conjugate a cytotoxin to antibodies include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. etal. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C J. (2001) Adv. Drug Deliv. Rev. 53:247-264.

Antibodies described herein can also be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine[131], indium[111], yttrium[90] and lutetium[177]. Methods for preparing radioimmunoconjugates are established in the art. Examples of radioimmunoconjugates are commercially available, including Zevalin™ (Spectrum Pharmaceuticals) and Bexxar™ (formally sold by GlaxoSmithKline), and similar methods can be used to prepare radioimmunoconjugates using antibodies described herein.

Nucleotide Sequences

The present disclosure includes nucleotide sequences encoding one or more antibodies described herein (e.g., a VHH described herein), or portion thereof (e.g., one or more CDRs described herein), and/or one or more fusion proteins described herein. In various instances, such nucleotide sequences may be present in a vector. In various instances such nucleotides may be present in the genome of a cell, e.g., a cell of a subject in need of treatment or a cell for production of an antibody, e.g. a mammalian cell for production of an antibody.

CLL-1

Human C-type lectin-like molecule-1 (CLL-1), also known as MICL or CLEC12A, is a type II transmembrane glycoprotein and member of the large family of C-type lectin-like receptors involved in immune regulation. CLL-1 has previously been identified from myeloid-derived cells. The intracellular domain of CLL-1 contains an immunotyrosine-based inhibition motif (ITIM) and a YXXM motif. Phosphorylation of ITIM-containing receptors on a variety of cells results in inhibition of activation pathways through recruitment of protein tyrosine phosphatases SUP-1, SHP-2 and SHIP. The YXXM motif has a potential SH2 domain-binding site for the p85 subunit of PI-3 kinase, 13 which has been implicated in cellular activation pathways, revealing a potential dual role of CLL-1 as an inhibitory and activating molecule on myeloid cells. Indeed, association of CLL-1 with SHP-1 and SHP-2 has been demonstrated experimentally in transfected and myeloid-derived cell lines.

The pattern of expression of CLL-1 in hematopoietic cells is restricted. It is found in particular in myeloid cells derived from peripheral blood and bone marrow, as well as in the majority of AML blasts. A recent study indicated that CLL-1 is also present on the majority of leukemic stem cells in the CD34+/CD38− compartment in AML but absent from CD34+/CD38− cells in normal and in regenerating bone marrow controls, which aids the discrimination between normal and leukemic stem cells. (See, e.g., Zhao et al., Haematologica 95:71-78 (2010); Bakker et al., Cancer Res. 64:8443-8450 (2004)).

The nucleotide and protein sequences of CLL-1 are known for many species. For example, the human sequences can be found at Genbank accession number AF247788.1 (coding sequence shown in SEQ ID NO:1) and Uniprot accession number Q5QGZ9 (SEQ ID NO:2). For the human CLL-1 protein shown as SEQ ID NO:2, the extracellular domain comprises approximately amino acids 65-265, the transmembrane domain comprises approximately amino acids 44-64, and the cytoplasmic domain comprises approximately amino acids 1-43. The stalk domain of human CLL-1 spans amino acids 65-139, and the C lectin domain spans amino acids 140-249, both with reference to the sequence shown in SEQ ID NO:2. One of ordinary skill will understand that CLL-1 variants (e.g., species homologs, allelic variants, etc.) can be optimally aligned, e.g., for identification of conserved residues and domains.

CLL-1 Associated Disorders

The antibodies and/or fusion proteins of the disclosure can be used, e.g., to detect and/or treat CLL-1 associated disorders, i.e., diseases correlated with elevated or reduced cell surface expression of CLL-1 as compared to CLL-1 expression in a standard control (e.g., a normal, non-disease, non-cancer cell). CLL-1 expression is normally limited to myeloid lineage cells, e.g., dendritic cells, granulocytes, and monocytes in the peripheral blood and spleen. In some instances, elevated CLL-1 levels are associated with cancer, in particular, in hematopoietic CSCs (e.g., LSCs), and in myeloproliferative disorders, including leukemias such as AML (acute myelogenous or myeloproliferative leukemia), MDS (myelodysplastic syndrome), myelofibrosis, CMML (chronic myelomonocytic leukemia), multiple myeloma, plasmacytoma, and CML (chronic myelogenous or myeloproliferative leukemia). See, e.g., Morsink et al., Blood Rev. 2018 Nov. 1. pii: 50268-960X(18)30072-9. doi: 10.1016/j.blre.2018.10.003. [Epub]; Bakker et al., Cancer Res. 64:8443-8450 (2004); Van Rhenen et al., Blood 110:2659-66 (2007); Zhao et al., Haematologica 95:71-78 (2010); Van Rhenen et al., Leukemia 21:1700-7 (2007); and Herrmann et al., Haematologica 97:219-26 (2012).

AML cells can be characterized and distinguished from other cells by detecting cell surface marker expression. Aside from being CLL-1+, AML cells can be CD33+(though some are CD33−), CD45+, and CDw52+. AML blasts (including LSCs) are typically CD34+CD38−. HSCs and LSCs can be characterized by expression of CD34, but the former do not express CLL-1. MDS cells can be characterized by expression of CDS, CD7, CD13, and CD34. CML cells can be characterized by expression of 7-ADD, CD33, CD34, and CD38.

Myelodysplastic Syndromes (MDS) include a group of closely-related blood formation disorders, in which the bone marrow shows qualitative and quantitative changes suggestive of a preleukemic process, but having a chronic course that does not necessarily terminate as acute leukemia. A variety of terms, including preleukemia, refractory anemia, refractory dysmyelopoietic anemia, smoldering or subacute leukemia, dysmyelopoietic syndrome (DMPS), and myelodysplasia, have all been used to describe MDS. These conditions can be characterized by a cellular marrow with impaired maturation (dysmyelopoiesis) and a reduction in the number of blood cells. DMPS can be characterized by presence of megablastoids, megarkaryocyte dysplasia, and an increase in number of abnormal blast cells, reflective of enhanced granulocyte maturation process. Patients with DMPS typically show chromosomal abonormalities similar to those found in acute myeloid leukemia and progress to acute myeloid leukemia in a certain fraction of afflicted patients.

Chronic myeloproliferative disorders are a collection of conditions that can be characterized by increased number of mature and immature granulocytes, erythrocytes, and platelets. Chronic myeloproliferative disorders can transition to other forms within this group, with a tendency to terminate in acute myeloid leukemia. Specific diseases within this group include polycythemia vera, chronic myeloid leukemia, agnogenic myeloid leukemia, essential thrombocythemia, and chronic neutrophilic leukemia.

Myelofibrosis can be characterized by scarring of the bone marrow that can result in reduced number of red and white blood cells, and platelets. Myelofibrotic scarring can result from leukemia, but can have other causes, such as thrombocytosis or adverse drug effects.

In various instances, an antibody and/or fusion protein described herein treats, alleviates, reduces the prevalence of, reduces the frequency of, or reduces the level or amount of one or more symptoms or biomarkers of a CLL-1-associated disorder. Specific symptoms and progression of symptoms vary among subjects. Thus, in some embodiments, an antibody and/or fusion protein described herein is administered to a subject in need thereof, e.g., a subject having a CLL-1-associated disorder.

In various instances, administration of an antibody and/or fusion protein described herein results in a decrease in the prevalence, frequency, level, and/or amount of one or more symptoms or biomarkers of a CLL-1-associated disorder, e.g., a decrease of at least 3%, 4%, 5%, 6%, 7%, 8%, 9%, 10%, 15%, 20%, 25%, 30%, 35%, 40%, 45%, 50%, 60%, 70%, 80%, 90%, 95%, 99%, or 100% of one or more symptoms or biomarkers as compared to a prior measurement in the subject or to a reference value.

In some embodiments, an effective dose of an antibody and/or fusion protein as described herein may be, e.g., less than 1,000 mg/dose, e.g., less than 900 mg/dose, 800 mg/dose, 700 mg/dose, 600 mg/dose, 500 mg/dose, 550 mg/dose, 400 mg/dose, 350 mg/dose, 300 mg/dose, 200 mg/dose, 100 mg/dose, 50 mg/dose, 25 mg/dose, or less. Alternatively or in combination with a dosage as disclosed herein, an antibody and/or fusion protein as described herein may be effectively or usefully administered at a frequency that is less than once per week, e.g., less than once every week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months, 7 months, 8 months, 9 months, 10 months, 11 months, or year.

In some embodiments, an antibody and/or fusion protein described herein can be used in a number of diagnostic and/or therapeutic applications. For example, detectably-labeled versions of antibodies as described herein can be used in assays to detect the presence or amount of CLL-1 in a sample (e.g., a biological sample). Antibodies and/or fusion proteins described herein can be used in in vitro assays for studying inhibition of CLL-1 activity. In some embodiments, an antibody and/or fusion protein described herein can be used as a positive control in an assay designed to identify additional novel compounds that inhibit CLL-1 or otherwise are useful for treating a CLL-1-associated disorder.

Antibodies and/or fusion proteins described herein may be used in monitoring a subject, e.g., a subject having, suspected of having, at risk of developing, or under treatment for one or more CLL-1-associated disorders. Monitoring may include determining the amount or activity of CLL-1 in a subject, e.g., in the serum of a subject. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration of an antibody and/or fusion protein as described herein. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a CLL-1-associated disorder described herein.

Measuring Interactions of Antibodies and CLL-1

The binding properties of an antibody described herein to CLL-1 can be measured by methods known in the art, e.g., one of the following methods: BIACORE analysis, Enzyme Linked Immunosorbent Assay (ELISA), x-ray crystallography, sequence analysis and scanning mutagenesis. The binding interaction of an antibody and CLL-1 can be analyzed using surface plasmon resonance (SPR). SPR or Biomolecular Interaction Analysis (BIA) detects bio-specific interactions in real time, without labeling any of the interactants. Changes in the mass at the binding surface (indicative of a binding event) of the BIA chip result in alterations of the refractive index of light near the surface. The changes in the refractivity generate a detectable signal, which are measured as an indication of real-time reactions between biological molecules. Methods for using SPR are described, for example, in U.S. Pat. No. 5,641,640; Raether (1988) Surface Plasmons Springer Verlag; Sjolander and Urbaniczky (1991) Anal. Chem. 63:2338-2345; Szabo et al. (1995) Curr. Opin. Struct. Biol. 5:699-705 and on-line resources provide by BIAcore International AB (Uppsala, Sweden). Additionally, a KinExA® (Kinetic Exclusion Assay) assay, available from Sapidyne Instruments (Boise, Id.) can also be used.

Information from SPR can be used to provide an accurate and quantitative measure of the equilibrium dissociation constant ($K_D$), and kinetic parameters, including $K_{on}$ and $K_{off}$, for the binding of an antibody to CLL-1. Such data can be used to compare different molecules. Information from SPR can also be used to develop structure-activity relationships (SAR). Variant amino acids at given positions can be identified that correlate with particular binding parameters, e.g., high affinity.

In certain embodiments, an antibody described herein exhibits high affinity for binding CLL-1. In various embodiments, $K_D$ of an antibody as described herein for CLL-1 is less than about $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, or $10^{-15}$ M. In certain instances, $K_D$ of an antibody as described herein for CLL-1 is between 0.001 and 1 nM, e.g., 0.001 nM, 0.005 nM, 0.01 nM, 0.05 nM, 0.1 nM, 0.5 nM, or 1 nM.

22

Formulations and Administration

The present disclosure includes compositions, e.g., pharmaceutical compositions, containing one or more antibodies and/or fusion proteins described herein, formulated together with a pharmaceutically acceptable carrier. Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). As used herein, "pharmaceutically acceptable carrier" includes any and all solvents, dispersion media, coatings, antibacterial and antifungal agents, isotonic and absorption delaying agents, and the like that are physiologically compatible. For example, the carrier can be suitable for intravenous, intramuscular, subcutaneous, parenteral, spinal or epidermal administration (e.g., by injection or infusion). Depending on the route of administration, the antibody may be coated in a material to protect the compound from the action of acids and other natural conditions that may inactivate the compound.

A pharmaceutical composition may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. These compositions may also contain adjuvants such as preservatives, wetting agents, emulsifying agents and dispersing agents.

Prevention of presence of microorganisms can be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Sterile injectable solutions can be prepared by incorporating an antibody in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of antibody and/or fusion protein described herein that can be combined with a carrier material to produce a single dosage form will vary depending upon the subject being treated, and the particular mode of administration. The amount of antibody and/or fusion protein that can be combined with a carrier material to produce a single dosage form will generally be that amount of the composition which produces a therapeutic effect. Generally, out of one hundred percent, this amount will range from about 0.01 percent to about ninety-nine percent of antibody, preferably from about 0.1 percent to about 70 percent, most preferably from about 1 percent to about 30 percent of antibody in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of antibody calculated to produce the desired therapeutic effect in association with the required pharmaceutical carrier. The specification for the dosage unit forms are dictated by and directly dependent on (a) the unique characteristics of the antibody and the particular therapeutic effect to be achieved, and (b) the limitations inherent in the art of compounding such an antibody for the treatment of sensitivity in individuals.

For administration of an antibody and/or fusion protein disclosed herein, the dosage ranges from about 0.0001 to 100 mg/kg, and more usually 0.01 to 5 mg/kg, of the subject body weight. For example dosages can be 0.3 mg/kg body weight, 1 mg/kg body weight, 3 mg/kg body weight, 5 mg/kg body weight, 10 mg/kg body weight or 20 mg/kg body weight or within the range of 1-20 mg/kg. An exemplary treatment regime entails administration once per week, once every two weeks, once every three weeks, once every four weeks, once a month, once every 3 months or once every three to 6 months, or with a short administration interval at the beginning (such as once per week to once every three weeks), and then an extended interval later (such as once a month to once every three to 6 months).

Alternatively, antibody and/or fusion protein can be administered as a sustained release formulation, in which case less frequent administration is required. Dosage and frequency vary depending on the half-life of the antibody and/or fusion protein in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of antibody and/or fusion protein in the pharmaceutical compositions of the disclosure may be varied so as to obtain an amount of antibody and/or fusion protein that is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition of the disclosure can be administered via one or more routes of administration using one or more of a variety of methods known in the art. As will be appreciated by the skilled artisan, the route and/or mode of administration will vary depending upon the desired results. Preferred routes of administration include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a composition can be administered via a non-parenteral route, such as a topical, epidermal or mucosal route of administration, for example, intranasally, orally, vaginally, rectally, sublingually or topically.

The antibody and/or fusion protein can be prepared with carriers that will protect against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition of the disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medicaments through the skin; U.S.

Pat. No. 4,447,233, which discloses a medication infusion
pump for delivering medication at a precise infusion rate;
U.S. Pat. No. 4,447,224, which discloses a variable flow
implantable infusion apparatus for continuous drug delivery;
U.S. Pat. No. 4,439,196, which discloses an osmotic drug
delivery system having multi-chamber compartments; and
U.S. Pat. No. 4,475,196, which discloses an osmotic drug
delivery system. Many other such implants, delivery sys-
tems, and modules are known to those skilled in the art.

In some embodiments, an antibody and/or fusion protein
described can be administered to a subject using a vector,
e.g., a viral vector, e.g., using known methods. In some
embodiments, a viral vector can be used to introduce an
antibody and/or fusion protein into a cancer cell (e.g., a
tumor cell). Introduction of such antibody and/or fusion
protein can increase susceptibility to a subject's immune
system and/or one or more additional therapeutic agents
(see, e.g., WO2017/075533).

A nucleic acid sequence encoding an antibody and/or
fusion protein described herein can be cloned into a number
of types of vectors. For example, a nucleic acid can be
cloned into a plasmid, a phagemid, a phage derivative, an
animal virus, and a cosmid. Other vectors can include
expression vectors, replication vectors, probe generation
vectors, sequencing vectors, and viral vectors. In other
examples, the vector can be a foamy viral (FV) vector, a type
of retroviral vector made from spumavirus. Viral vector
design and technology is well known in the art as described
in Sambrook et al, (Molecular Cloning: A Laboratory
Manual, 2001), and in other virology and molecular biology
manuals.

A number of viral based systems have been developed for
gene transfer into mammalian cells. Examples of viral
vectors include, but are not limited to, retroviruses, adeno-
viruses, adeno-associated viruses, herpes viruses, lentivi-
ruses, poxviruses, herpes simplex 1 virus, herpes virus,
oncoviruses (e.g., murine leukemia viruses), and the like. In
general, a suitable vector contains an origin of replication
functional in at least one organism, a promoter sequence,
convenient restriction endonuclease sites, and one or more
selectable markers, (e.g., WO 01/96584; WO 01/29058; and
U.S. Pat. No. 6,326,193). Lentiviral and Retroviral trans-
duction can be enhanced by the addition of polybrene
(SantaCruz sc-134220; Millipore TR-1003-G; Sigma
107689), a cationic polymer (also known as hexamehtrine
bromide) that is used to increase the efficiency of the
retrovirus transduction.

Retroviruses are enveloped viruses that belong to the viral
family Retroviridae. Once in a host's cell, the virus repli-
cates by using a viral reverse transcriptase enzyme to
transcribe its RNA into DNA. The retroviral DNA replicates
as part of the host genome, and is referred to as a provirus.
A selected gene can be inserted into a vector and packaged
in retroviral particles using techniques known in the art. The
recombinant virus can then be isolated and delivered to cells
of the subject in vivo. A number of retroviral systems are
known in the art, (see, e.g., U.S. Pat. Nos. 5,994,136,
6,165,782, and 6,428,953).

Retroviruses include the genus of Alpharetrovirus (e.g.,
avian leukosis virus), the genus of Betaretrovirus; (e.g.,
mouse mammary tumor virus) the genus of Deltaretrovirus
(e.g., bovine leukemia virus and human T-lymphotropic
virus), the genus of Epsilonretrovirus (e.g., Walleye dermal
sarcoma virus), and the genus of Lentivirus. In some
embodiments, a retrovirus is a lentivirus a genus of viruses
of the Retroviridae family, e.g., characterized by a long
incubation period. Lentiviruses are unique among the retroviruses in being able to infect non-dividing cells; they can
deliver a significant amount of genetic information into the
DNA of the host cell, so can be used as an efficient gene
delivery vector. In some examples, a lentivirus can be, but
not limited to, human immunodeficiency viruses (HIV-1 and
HIV-2), simian immunodeficiency virus (S1V), feline
immunodeficiency virus (FIV), equine infections anemia
(EIA), and visna virus. Vectors derived from lentiviruses
offer the means to achieve significant levels of gene transfer
in vivo.

In some embodiments, a vector is an adenovirus vector.
Adenoviruses are a large family of viruses containing double
stranded DNA. They replicate the DNA of the host cell,
while using a host's cell machinery to synthesize viral RNA
DNA and proteins. Adenoviruses are known in the art to
affect both replicating and non-replicating cells, to accom-
modate large transgenes, and to code for proteins without
integrating into the host cell genome.

In some embodiments, an AAVP vector is used. An AAVP
vector is a hybrid of prokaryotic-eukaryotic vectors, which
are chimeras of genetic cis-elements of recombinant adeno-
associated virus and phage. An AAVP combines selected
elements of both phage and AAV vector systems, providing
a vector that is simple to produce in bacteria and can exhibit
little or no packaging limit, while allowing infection of
mammalian cells combined with integration into the host
chromosome. Vectors containing many of the appropriate
elements are commercially available, and can be further
modified by standard methodologies to include the neces-
sary sequences. Among other things, AAVPs do not require
helper viruses or trans-acting factors. In addition, the native
tropism of AAV for mammalian cells is eliminated since
there is not AAV capsid formation. Other methods and
details are in U.S. Pat. No. 8,470,528 and Hajitou A. et al.,
Cell, 125: 358-398.

In some embodiments, a human papilloma (HPV)
pseudovirus is used. DNA plasmids can be packaged into
papillomavirus L1 and L2 capsid protein to generate
pseudovirion that can efficiently deliver DNA. The encap-
sulation can protect the DNA from nucleases and provides a
targeted delivery with a high level of stability. Many of the
safety concerns associated with the use of viral vectors can
be mitigated with an HPV pseudovirus. Other methods and
examples are in Hung, C., et al., Plos One, 7:7(e40983);
2012, U.S. Pat. No. 8,394,411, and Kines, R., et al Int J of
Cancer, 2015.

In some embodiments, an oncolytic virus is used. Onco-
lytic virus therapy can selectively replicate the virus in
cancer cells, and can subsequently spread within a tumor,
e.g., without affecting normal tissue. Alternatively, an onco-
lytic virus can preferentially infect and kill cells without
causing damage to normal tissues. Oncolytic viruses can
also effectively induce immune responses to themselves as
well as to the infected tumor cell. Typically, oncolytic
viruses fall into two classes: (I) viruses that naturally rep-
licate preferentially in cancer cells and are nonpathogenic in
humans. Exemplary class (I) oncolytic viruses include
autonomous parvoviruses, myxoma virus (poxvirus),
Newcastle disease virus (NDV; paramyxovirus), reovirus,
and Seneca valley virus (picornavirus). A second class (II),
includes viruses that are genetically manipulated for use as
vaccine vectors, including measles virus (paramyxovirus),
poliovirus (picornavirus), and vaccinia virus (poxvirus).
Additionally, oncolytic viruses may include those geneti-
cally engineered with mutations/deletions in genes required
for replication in normal but not in cancer cells including
adenovirus, herpes simplex virus, and vesicular stomatitis virus. Oncolytic viruses can be used as a viral transduction method due to their low probability of genetic resistance because they can target multiple pathways and replicate in a tumor-selective method. The viral dose within a tumor can increase over time due to in situ viral amplification (as compared to small molecule therapies which decrease with time), and safety features can be built in (i.e., drug and immune sensitivity).

Combination Therapies

In various embodiments, an antibody and/or fusion protein as described herein may be included in a course of treatment that further includes administration of at least one additional agent to a subject. In various instances, an additional agent administered in combination with an antibody and/or fusion protein as described herein can be cytarabine (cytosine arabinoside, or ara-C) and/or antharcycline drugs such as doxorubicin, daunorubicin, daunomycin, idarubicin and mitoxantrone; other chemotherapeutic drugs such as Hydroxyurea (Hydrea®), Decitabine (Dacogen®), Cladribine (Leustatin®, 2-CdA), Fludarabine (Fludara®), Topotecan, Etoposide (VP-16), 6-thioguanine (6-TG), corticosteroid drugs, such as prednisone or dexamethasone (Decadron®), methotrexate (MTX), 6-mercaptopurine (6-MP) or Azacitidine (Vidaza®), all-trans-retinoic acid (ATRA), tretinoin, or Vesanoid® and arsenic trioxide (ATO, Trisenox®). In some embodiments, a fusion protein described herein (e.g., a fusion protein consisting of or comprising one or more VHH and one or more tumor antigen) is administered in combination with a cellular therapeutic (e.g., a CAR-T cell) or antibody drug conjugate that binds to such one or more tumor antigen as described in, e.g., WO2017/075537, WO2017/075533, WO2018156802, and WO2018156791.

In various instances, an additional agent administered in combination with an antibody and/or fusion protein as described herein may be administered at the same time as an antibody and/or fusion protein, on the same day as an antibody and/or fusion protein, or in the same week as an antibody and/or fusion protein. In various instances, an additional agent administered in combination with an antibody and/or fusion protein as described herein may be administered in a single formulation with an antibody and/or fusion protein. In certain embodiments, an additional agent administered in a manner temporally separated from administration of an antibody and/or fusion protein as described herein, e.g., one or more hours before or after, one or more days before or after, one or more weeks before or after, or one or more months before or after administration of an antibody and/or fusion protein. In various embodiments, the administration frequency of one or more additional agents may be the same as, similar to, or different from the administration frequency of an antibody and/or fusion protein as described herein.

When compositions are to be used in combination with a second active agent, the compositions can be co-formulated with the second agent or the compositions can be formulated separately from the second agent formulation. For example, the respective pharmaceutical compositions can be mixed, e.g., just prior to administration, and administered together or can be administered separately, e.g., at the same or different times.

In some embodiments, combined administration of an antibody and/or fusion protein described herein and an additional agent results in an improvement in a condition or a symptom thereof to an extent that is greater than one produced by either the antibody (or fusion protein) or the additional agent alone. The difference between the combined effect and the effect of each agent alone can be a statistically significant difference. In some embodiments, combined administration of an antibody and/or fusion protein described herein and an additional agent allows administration of the additional agent at a reduced dose, at a reduced number of doses, and/or at a reduced frequency of dosage compared to a dosing regimen for the additional agent, e.g., a standard dosing regimen approved for the additional agent.

Kits

An antibody, or antigen-binding fragment thereof, and/or fusion described herein (e.g., a pharmaceutical composition comprising an antibody or antigen-binding fragment and/or fusion protein) can be provided in a kit. In some instances, the kit includes (a) a container that contains an antibody and/or fusion protein described herein (e.g., a pharmaceutical composition comprising an antibody and/or fusion protein described herein) and, optionally (b) informational material. The informational material can be descriptive, instructional, marketing or other material that relates to the methods described herein and/or the use of an antibody and/or fusion protein, e.g., for therapeutic benefit.

The informational material of a kit is not limited in its form. In some instances, the informational material can include information about production of an antibody and/or fusion protein, amino acid of an antibody and/or fusion protein, nucleic acid encoding an antibody and/or fusion protein, molecular weight of an antibody and/or fusion protein, concentration, date of expiration, batch or production site information, and so forth. In other situations, the informational material relates to methods of administering an antibody and/or fusion protein, e.g., in a suitable amount, manner, or mode of administration (e.g., a dose, dosage form, or mode of administration described herein). The method can be a method of treating a subject having a CLL-1 associated disorder.

In some cases, the informational material, e.g., instructions, is provided in printed matter, e.g., a printed text, drawing, and/or photograph, e.g., a label or printed sheet. The informational material can also be provided in other formats, such as Braille, computer readable material, video recording, or audio recording. In other instances, the informational material of the kit is contact information, e.g., a physical address, email address, website, or telephone number, where a user of the kit can obtain substantive information about an antibody therein and/or their use in the methods described herein. The informational material can also be provided in any combination of formats.

In addition to an antibody and/or fusion protein described herein, a kit can include other ingredients, such as a solvent or buffer, a stabilizer, or a preservative. A kit can also include other agents, e.g., a second or third agent, e.g., other therapeutic agents. The components can be provided in any form, e.g., liquid, dried or lyophilized form. The components can be substantially pure (although they can be combined together or delivered separate from one another) and/or sterile. When the components are provided in a liquid solution, the liquid solution can be an aqueous solution, such as a sterile aqueous solution. When the components are provided as a dried form, reconstitution generally is by the addition of a suitable solvent. The solvent, e.g., sterile water or buffer, can optionally be provided in the kit.

A kit can include one or more containers for an antibody (and/or fusion protein) and/or other agents. In some cases, a kit contains separate containers, dividers or compartments for an antibody and/or fusion protein and informational material. For example, an antibody and/or fusion protein can be contained in a bottle, vial, or syringe, and the informational material can be contained in a plastic sleeve or packet. In other situations, the separate elements of a kit are contained within a single, undivided container. For example, an antibody and/or fusion protein can be contained in a bottle, vial or syringe that has attached thereto the informational material in the form of a label. In some cases, a kit can include a plurality (e.g., a pack) of individual containers, each containing one or more unit dosage forms (e.g., a dosage form described herein) of an antibody and/or fusion protein. Containers can include a unit dosage, e.g., a unit that includes an antibody and/or fusion protein. For example, a kit can include a plurality of syringes, ampules, foil packets, blister packs, or medical devices, e.g., each containing a unit dose. The containers of kits can be air tight, waterproof (e.g., impermeable to changes in moisture or evaporation), and/or light-tight.

A kit can optionally include a device suitable for administration of an antibody and/or fusion protein, e.g., a syringe or other suitable delivery device. A device can be provided preloaded with an antibody and/or fusion protein, e.g., in a unit dose, or can be empty, but suitable for loading.

Recombinant Gene Technology

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

Recombinant expression of a gene, such as a nucleic acid encoding a polypeptide, such as an antibody described herein, can include construction of an expression vector containing a nucleic acid that encodes the polypeptide. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then be cultured by conventional techniques to produce polypeptides. A number of viral based systems have been developed for gene transfer into mammalian cells. Examples of viral vectors include, but are not limited to, retroviruses, adenoviruses, adeno-associated viruses, herpes viruses, lentiviruses, poxviruses, herpes simplex 1 virus, herpes virus, oncoviruses (e.g., murine leukemia viruses, vaccinia virus), and the like. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193). For example, lymphocytes (e.g., T cells) can be transduced using a lentiviral or retroviral vector. An oncolytic viral vector (e.g., adenovirus, vaccinia, AAV) can be used to transduce a tumor cell (e.g., which can secrete an antibody described herein). See, e.g., WO2017/075533.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1—Assessment of VHH Antibodies

The clones described in the Examples have the amino acid sequences noted in Table 2.

TABLE 2

| Clone | Sequence |
| --- | --- |
| 1B1, 2A6, 2A10, 2C5, 1B2, 1B3, 1B8, 1C2, 1C3, 1C10, 1E11, 1G2, 1H9, 2D7, 2D11, 2D3, 2B3, 2B8, 1A6 | SEQ ID NO: 3 |
| 1A9, 1C7, 1F2, 1D6, 2C11, 2E3, 2B6 | SEQ ID NO: 4 |
| 2G11, 2H2, 1G6 | SEQ ID NO: 5 |
| 2F6, 2A7 | SEQ ID NO: 6 |
| 1C8 and 1H6 | SEQ ID NO: 7 |
| 1C9, 1A8, 1B12, 2F10, 2G3 | SEQ ID NO: 8 |
| 1G4, 1H11, 1F10 | SEQ ID NO: 9 |
| 1G3 and 2H10 | SEQ ID NO: 10 |
| 2C8 | SEQ ID NO: 11 |
| 2F5 | SEQ ID NO: 12 |
| 2A11 | SEQ ID NO: 13 |
| 1A10 | SEQ ID NO: 14 |
| 2H3 | SEQ ID NO: 15 |
| 2F4 and 1H1 | SEQ ID NO: 16 |
| 1C6 | SEQ ID NO: 17 |
| 1D2 | SEQ ID NO: 18 |
| 1B5 | SEQ ID NO: 19 |
| 2F3 | SEQ ID NO: 20 |
| 2A8 | SEQ ID NO: 21 |
| 2G10 | SEQ ID NO: 22 |
| IE3 | SEQ ID NO: 23 |
| 1B11 | SEQ ID NO: 24 |
| 2C2 | SEQ ID NO: 25 |

Around 184 sdAb samples were screened for binding to CLEC12A (also known as CLL-1), coated onto a plate, by ELISA. Plates were coated with 1 µg/mL human CLEC12A in PBS (O/N 4C), then blocked with 5% milk/PBST (2 hr, room temp); added bacterially expressed sdAbs diluted in 1:1 in Block (1 hr), washed 5× with PBST, detected with mouse anti-myc-Tag monoclonal antibody (mAb) for 1 hr, followed by goat anti-mouse IgG-HRP (1 hr), both in Block, washed 5× with PBST between antibodies, and plate developed 30 minutes. Each plate included 4 controls/92 samples per plate. About 32% of sdAb screened were ELISA posi-
tive. FIG. 1 shows binding data for certain clones.

Figure 2A:
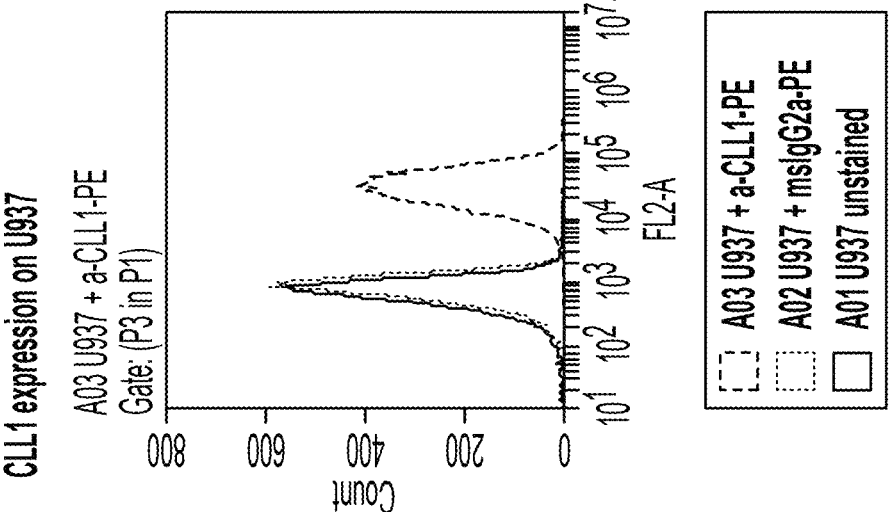
FIGS. 2A-2C show U937 cell binding by certain VHH clones.
Figure 2B:
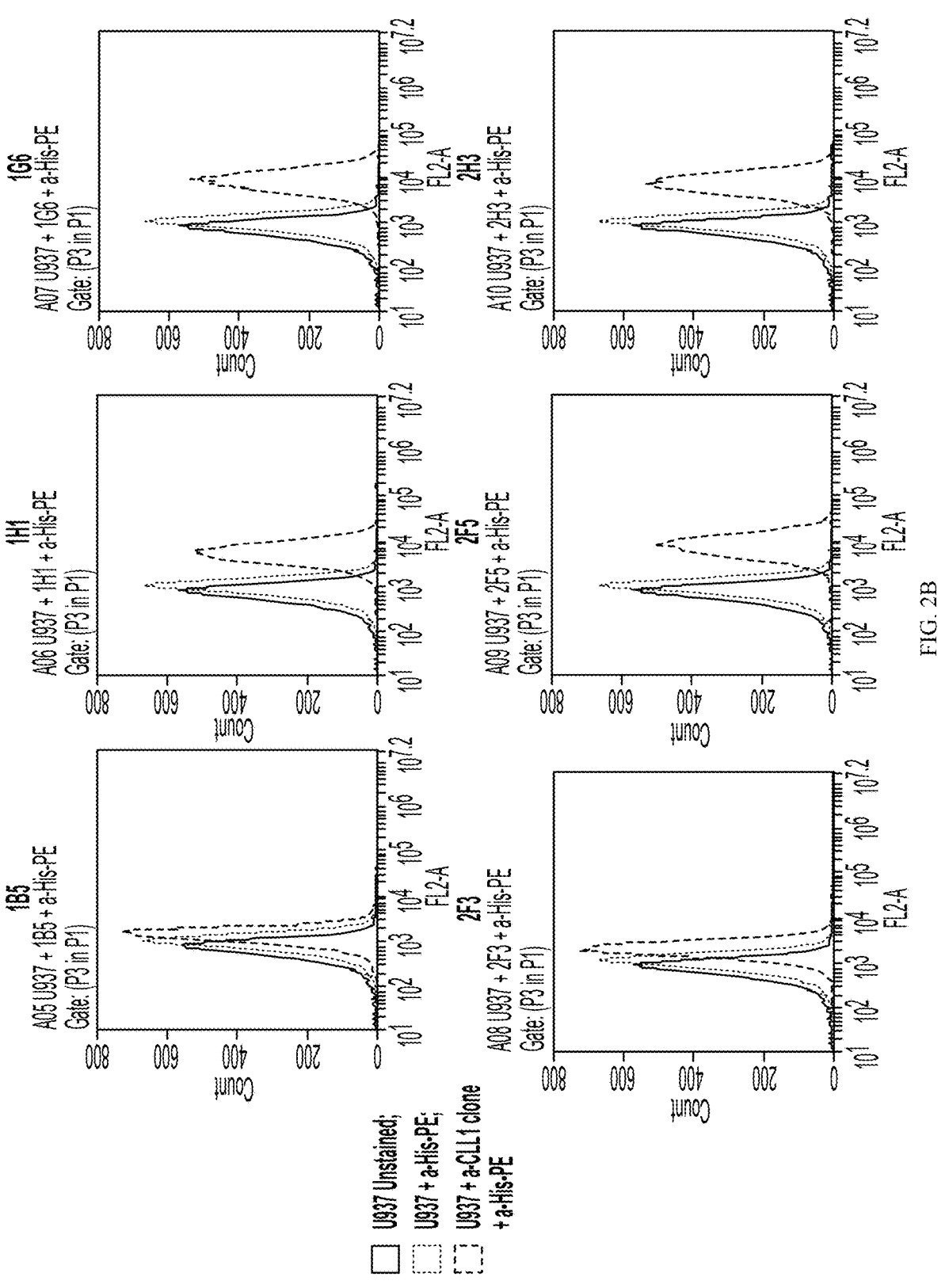
Figures 2, 2C:
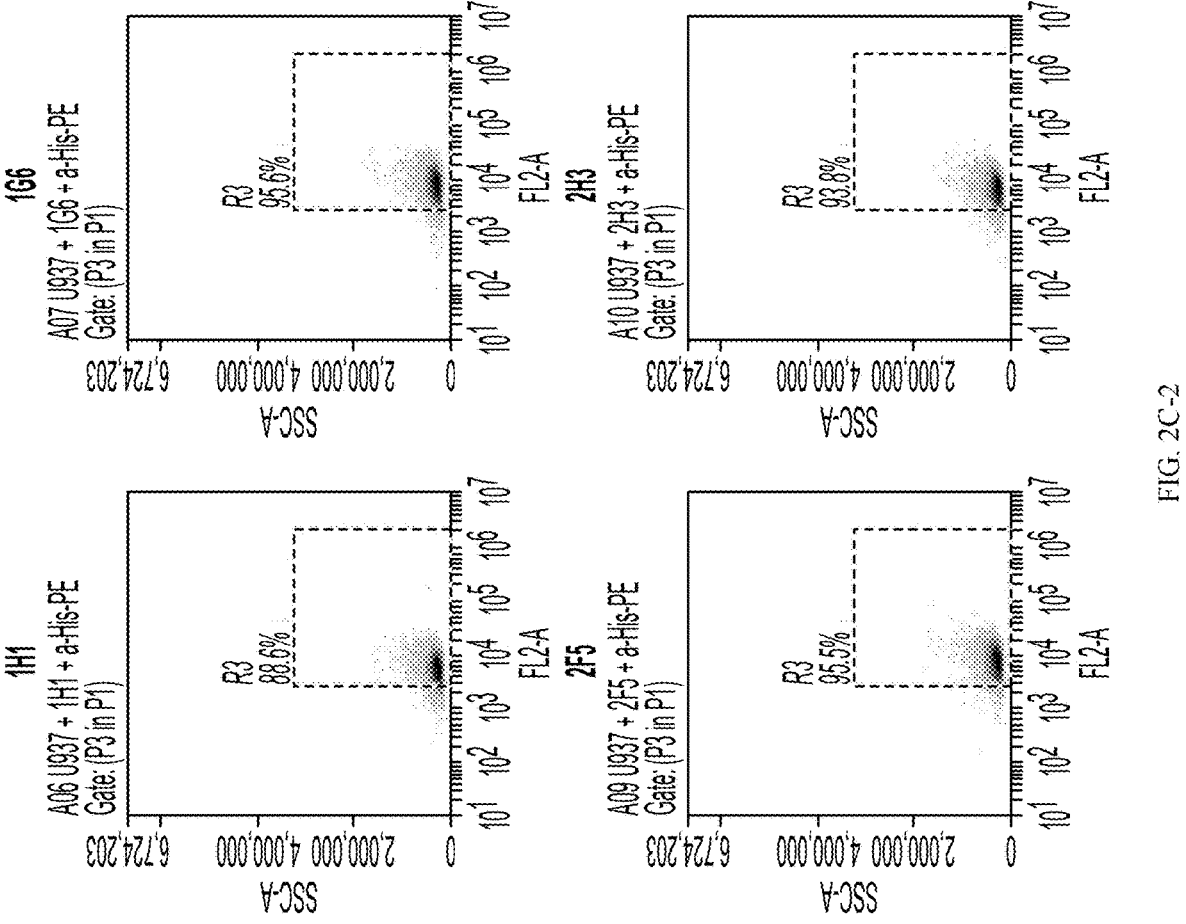

U937 cell binding by VHH clones was assessed. Briefly,
the method included: U937 cells (2.5×10^5) were Fc blocked
(human Fc block, BD Cat. #BDB564220) for 10 min at room
temperature, then washed once with FACS buffer (PBS+1%
BSA+0.1% Sodium Azide) by spinning at 500G for 2 min;
VHH clones (3 µg/ml as final conc) in FACS buffer were
added to the cell pellets and incubated for 30 min at 4° C.,
then washed twice with FACS buffer by spinning at 500G
for 2 min; anti-His-PE (R&D Systems, Cat. #IC050P) was
added to cells; the mixture was incubated for 30 min at 4°
C. and washed twice with FACS buffer by spinning at 500G
for 2 min; 1% PFA (Paraformaldehyde) in PBS was added
to cell pellet to fix the cells, followed by FACS analysis.
VHH clones tested: 1B5: stock=1.6 mg/ml; 1H1: stock=1.9
mg/ml; 1G6: stock=1.1 mg/ml; 2F3: stock=1.45 mg/ml;
2F5: stock=0.5 mg/ml; 2H3: stock=2 mg/ml. As shown in
FIGS. 2A-2C, binding of clones 1H1, 1G6, 2F5 and 2H3 to
U937 cells was detected with anti-His-PE; very little binding
of clones 1B5 and 2F3 to U937 cells could be detected by
anti-His-PE.

Figure 3A:
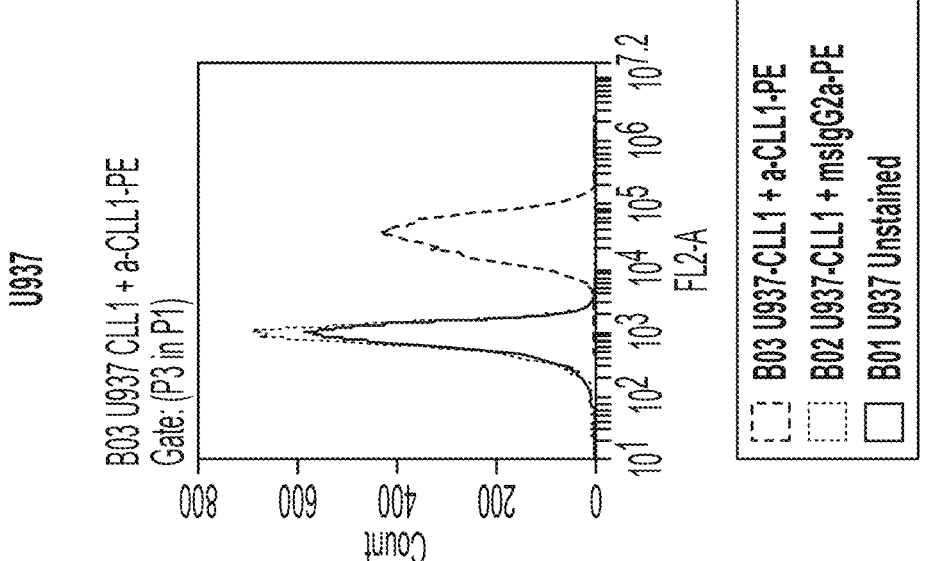
Figure 3C:
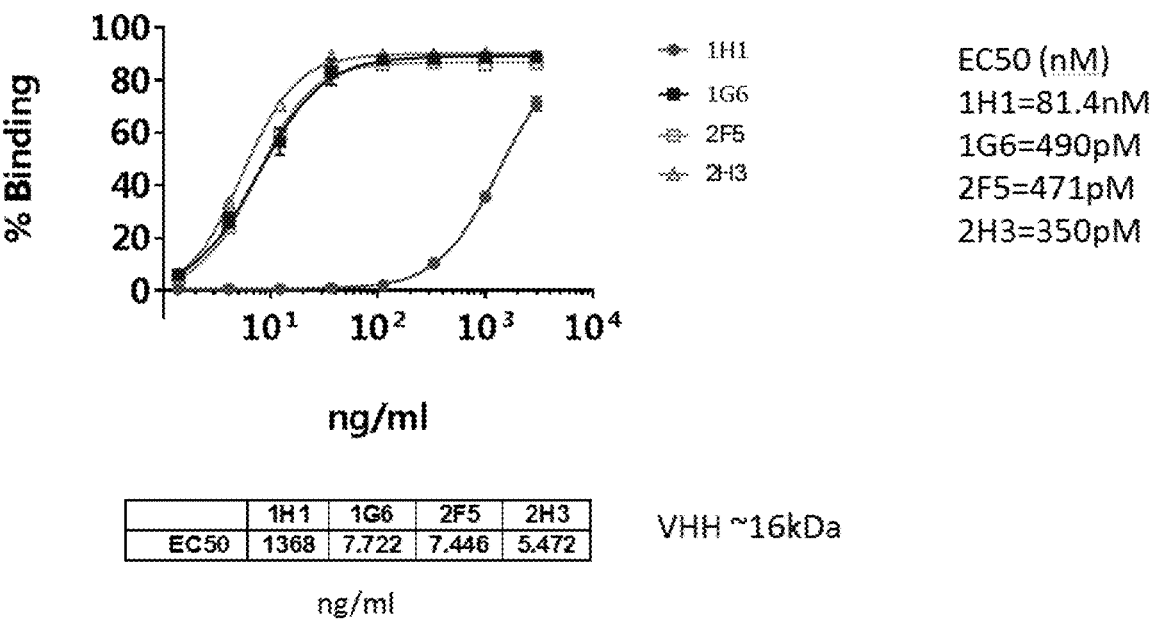

U937 cell binding by VHH clones was assessed using
varying doses to determine EC50s. Briefly, the method
included: VHH clones (3 ug/ml as starting conc./test, with
3× serial dilutions) in FACS buffer were added to Fc blocked
U937 or 293T-CLL1 cells (2.5×10^5), the mixtures were
incubated for 30 min at 4° C., then washed twice with FACS
buffer by spinning at 500G for 2 min; anti-His-PE was added
to cells, the mixture was incubated for 30 min at 4° C. and
washed twice with FACS buffer by spinning at 500G for 2
min; 1% PFA (Paraformaldehyde) in PBS was added to cell
pellet to fix the cells, followed by FACS analysis. VHH
clones tested: 1B5: stock=1.6 mg/ml; 1H1: stock=1.9
mg/ml; 1G6: stock=1.1 mg/ml; 2F3: stock=1.45 mg/ml;
2F5: stock=0.5 mg/ml; 2H3: stock=2 mg/ml. As shown in
FIGS. 3A-3C, the EC50s of clones on U937 cells were:
1G6=0.49 nM, 2F5=0.47 nM, 2H3=0.35 nM and 1H1=81
nM.

Figures 1, 4A:
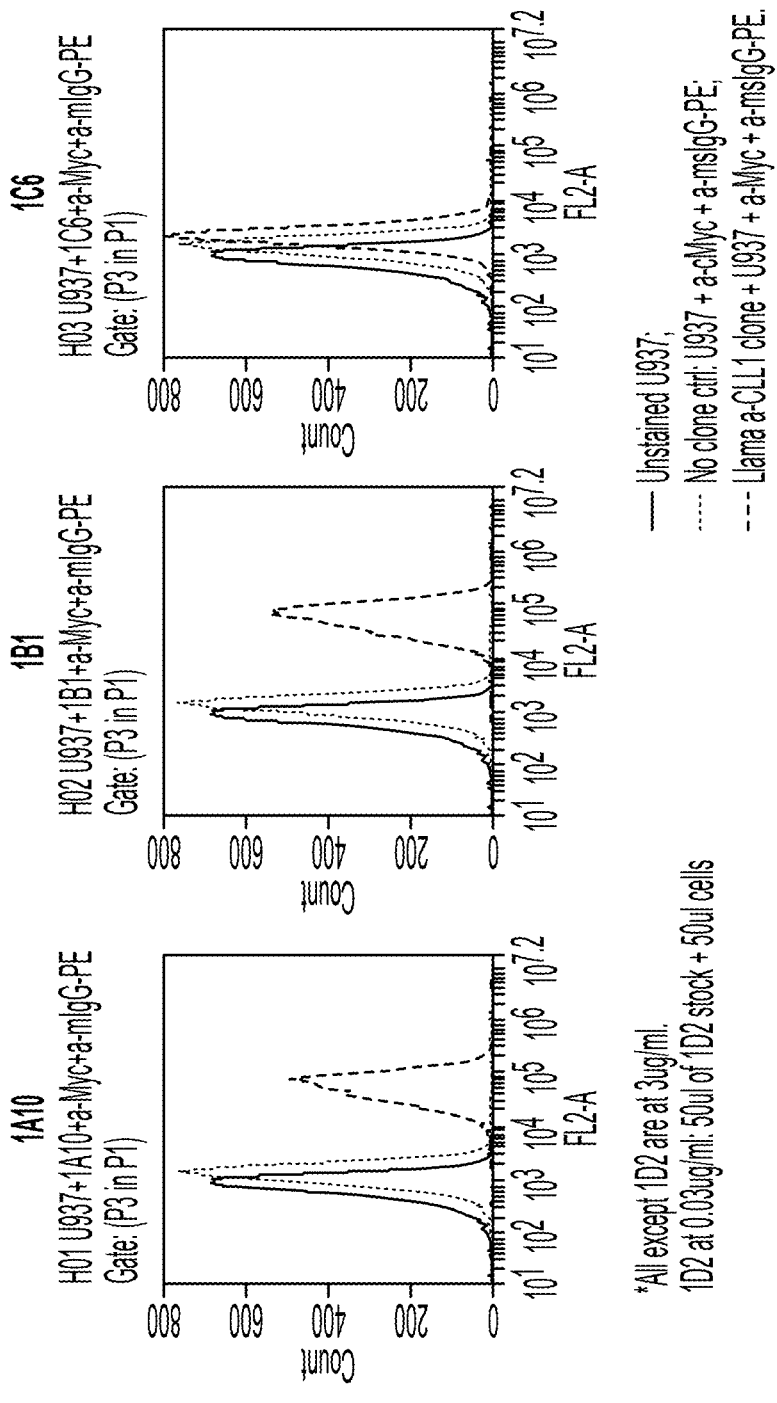
Figures 2, 4A:
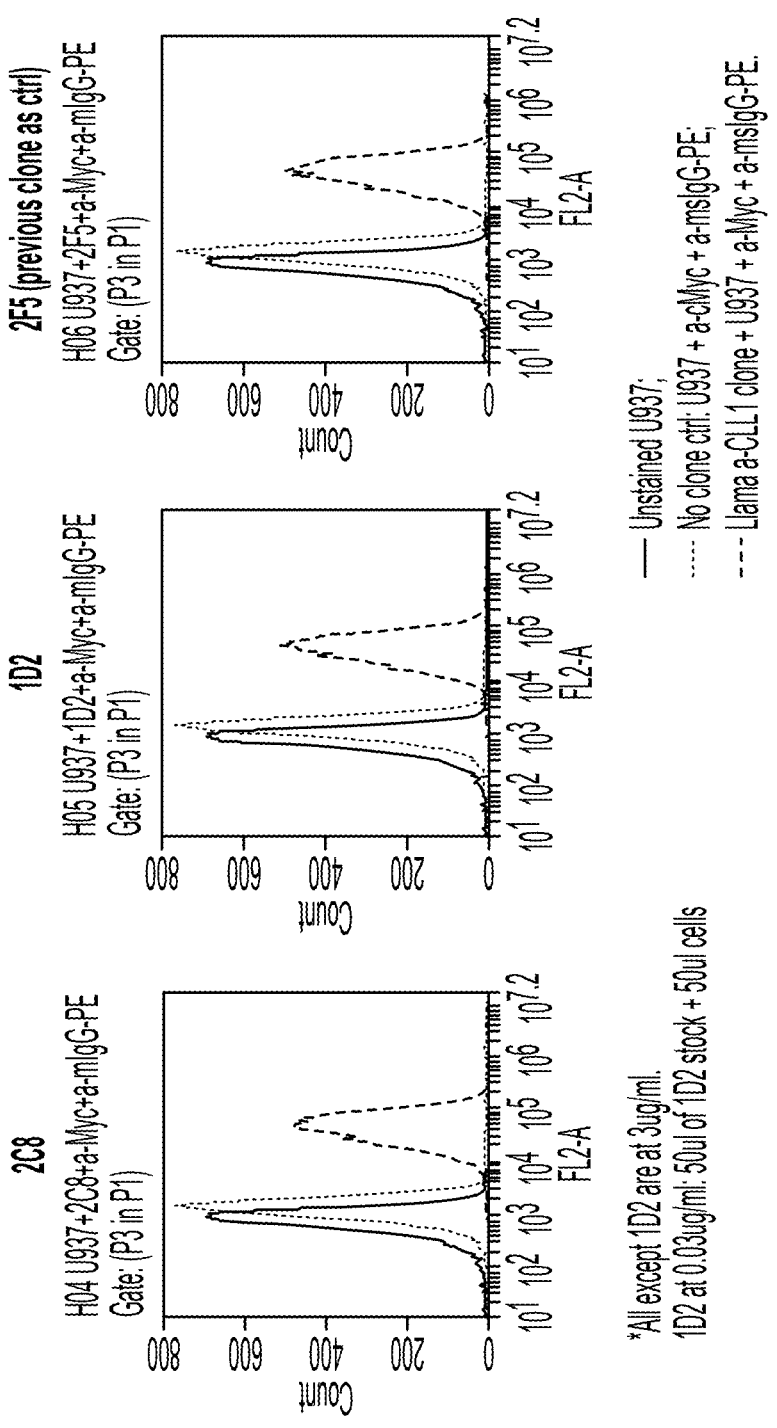
Figures 1, 5A:
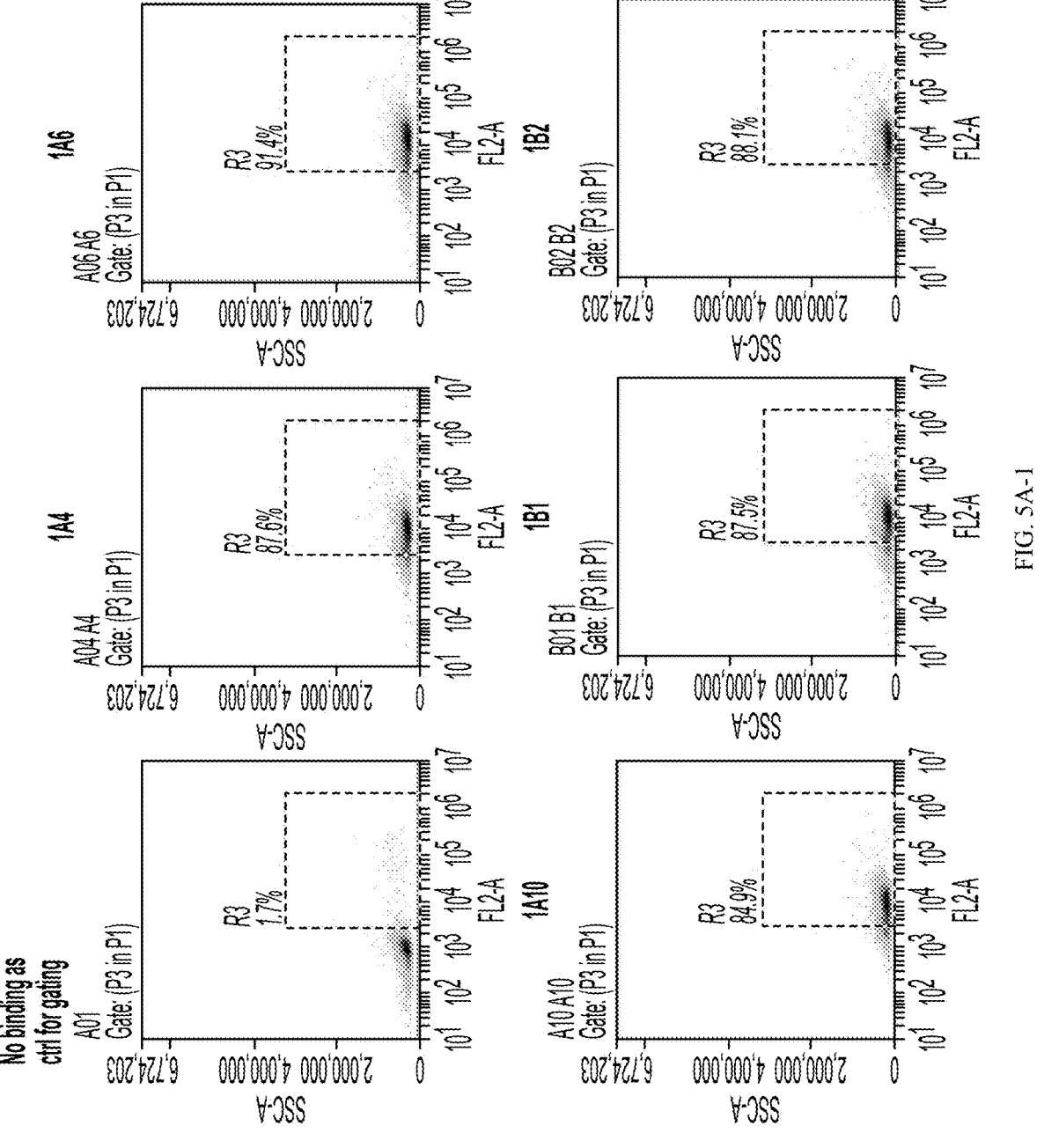
FIGS. 5A-5D show U937 cell binding by certain VHH clones.
Figures 2, 5A:
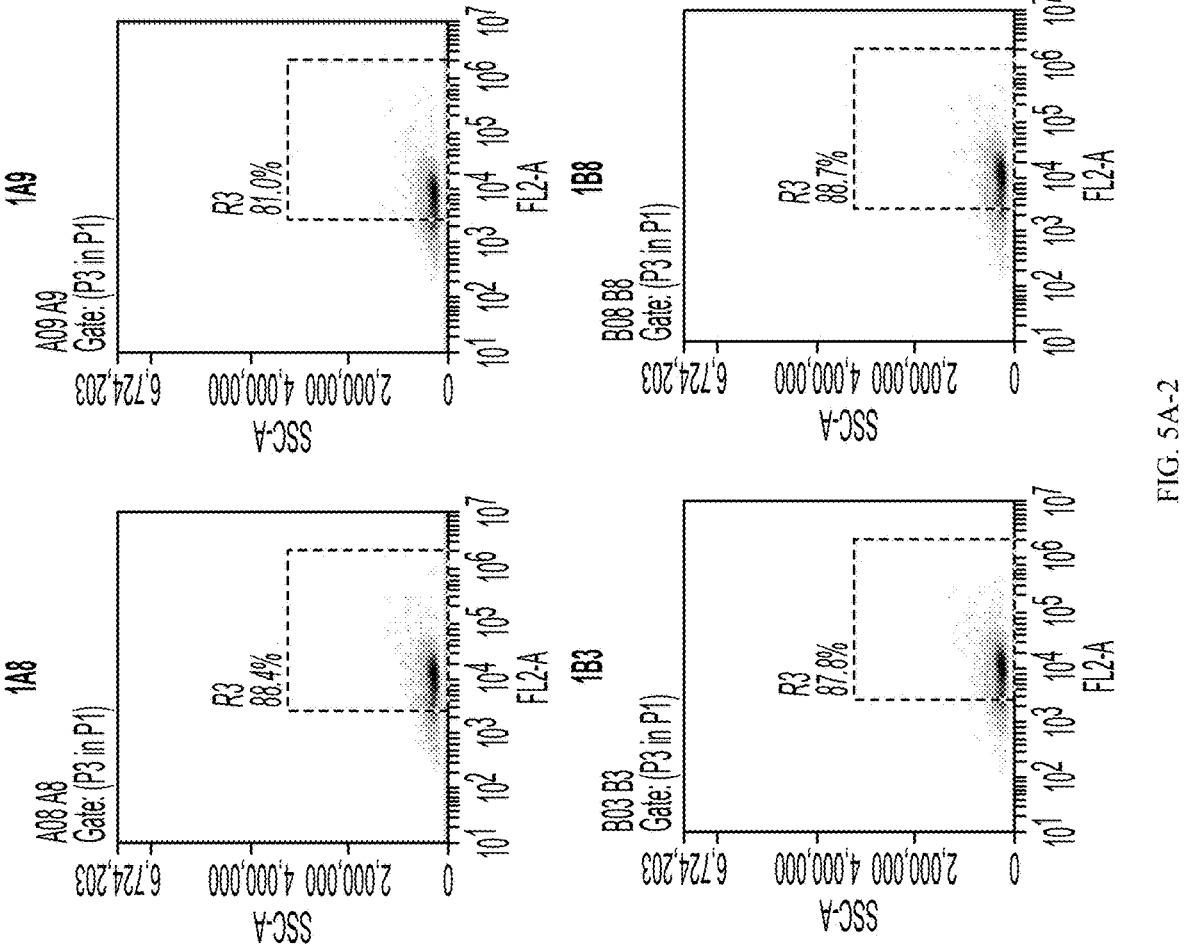
Figures 1, 5B:
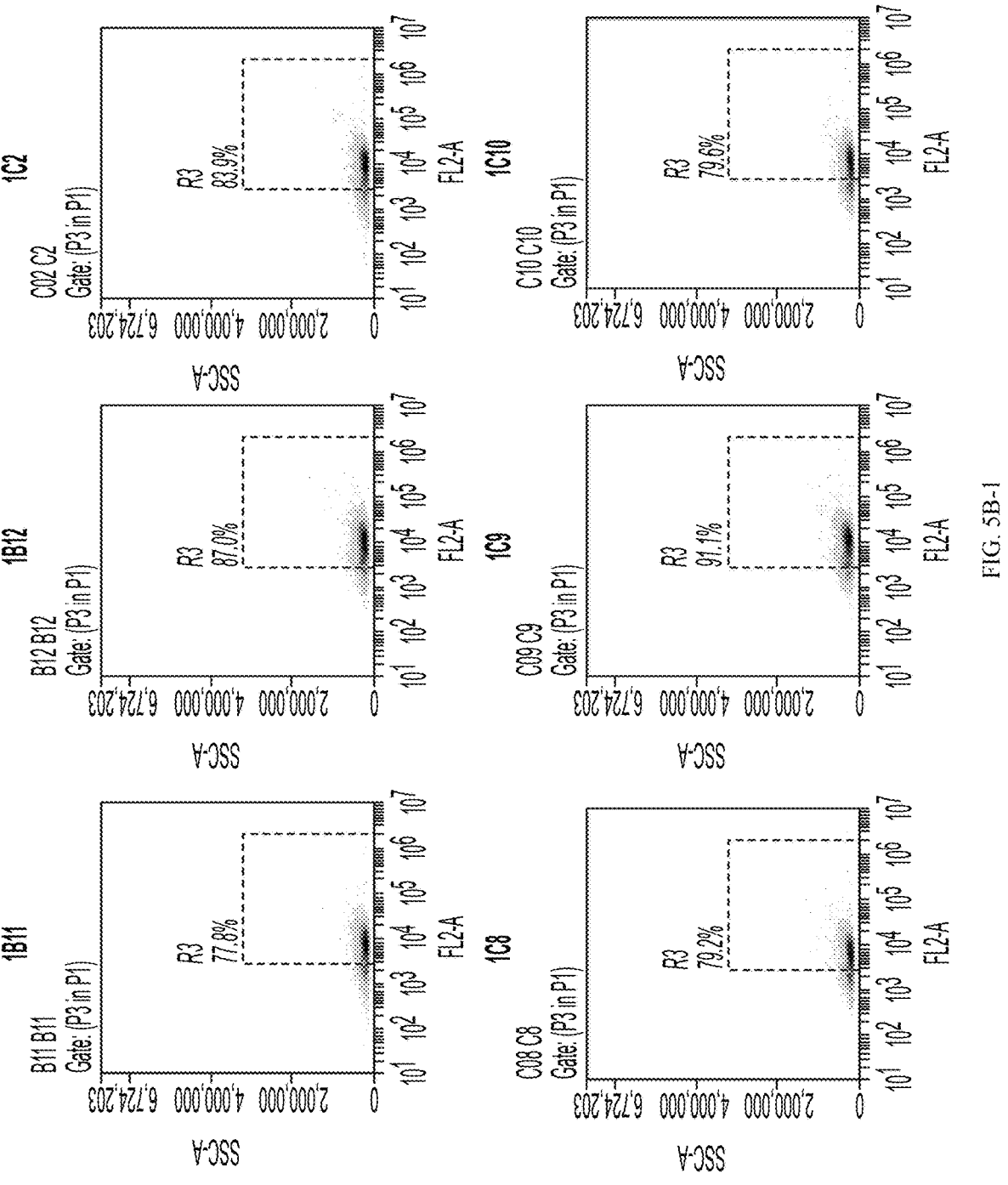
Figures 2, 5B:
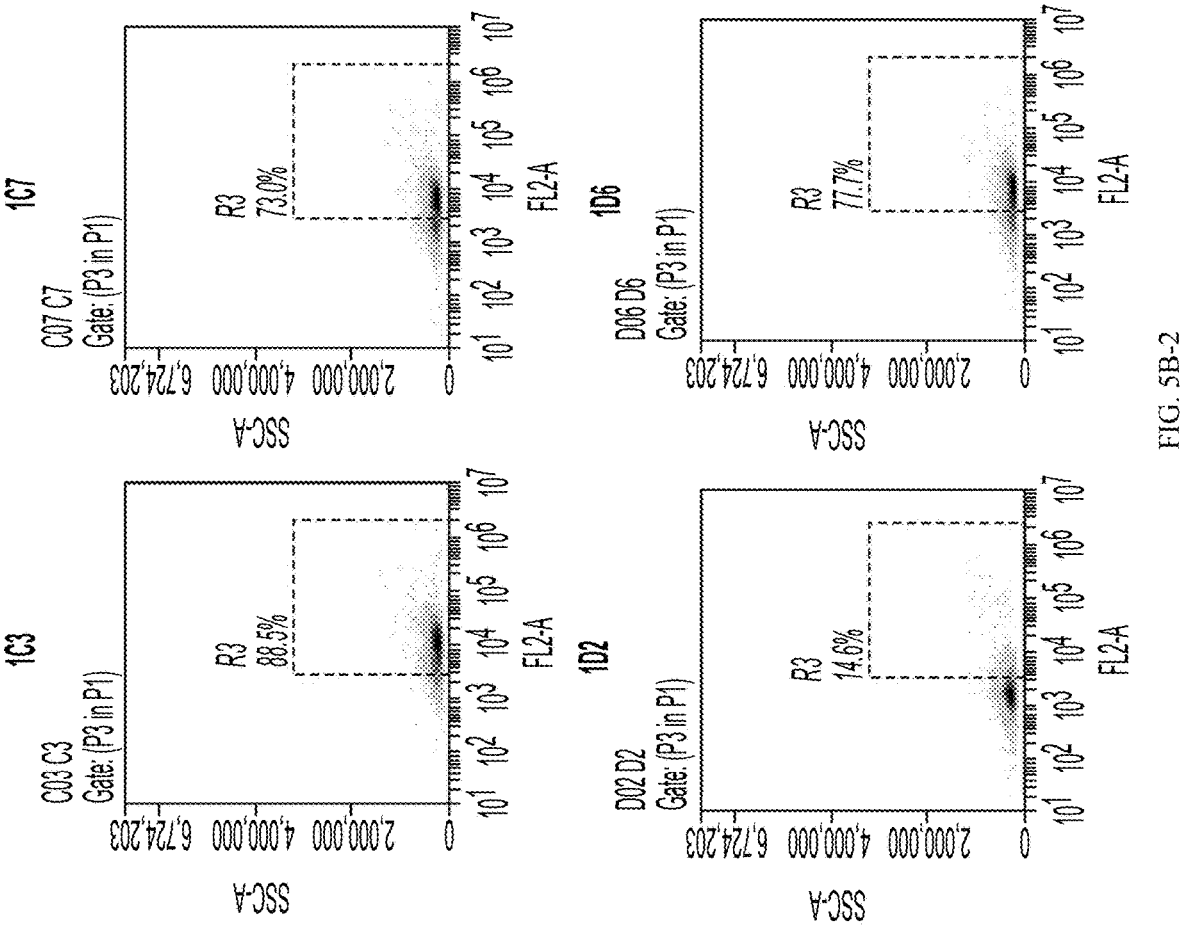
Figures 1, 5C:
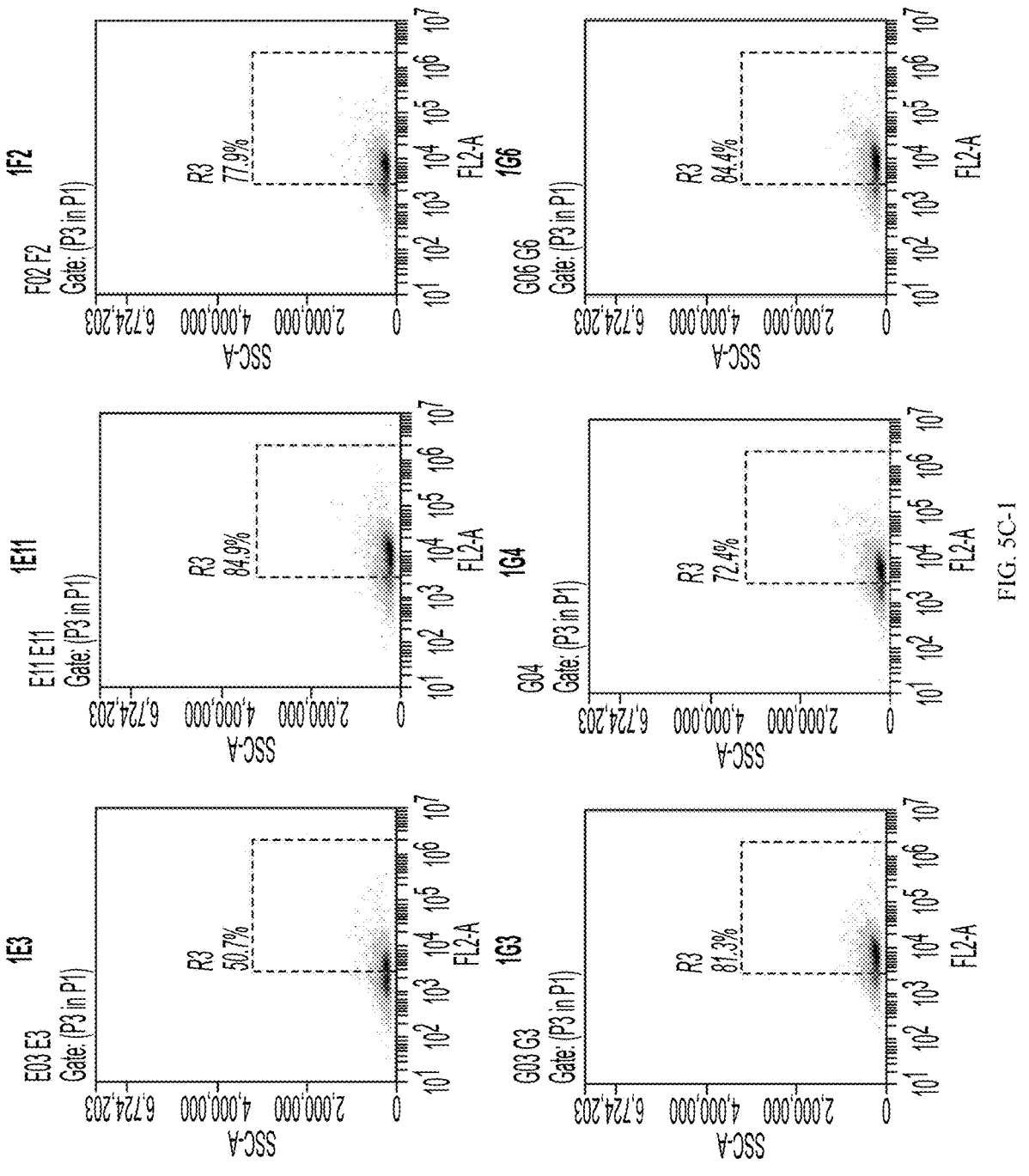
Figures 2, 5C:
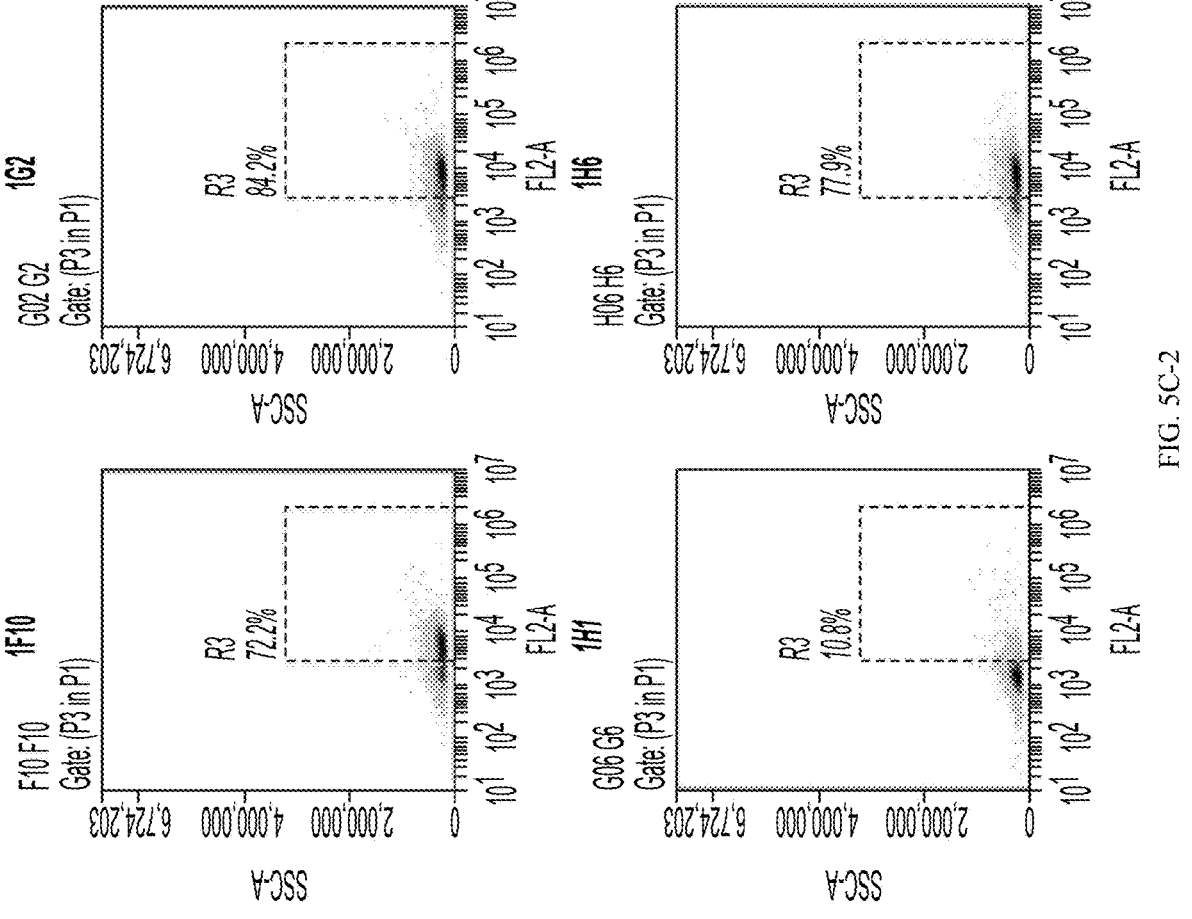
Figure 5D:
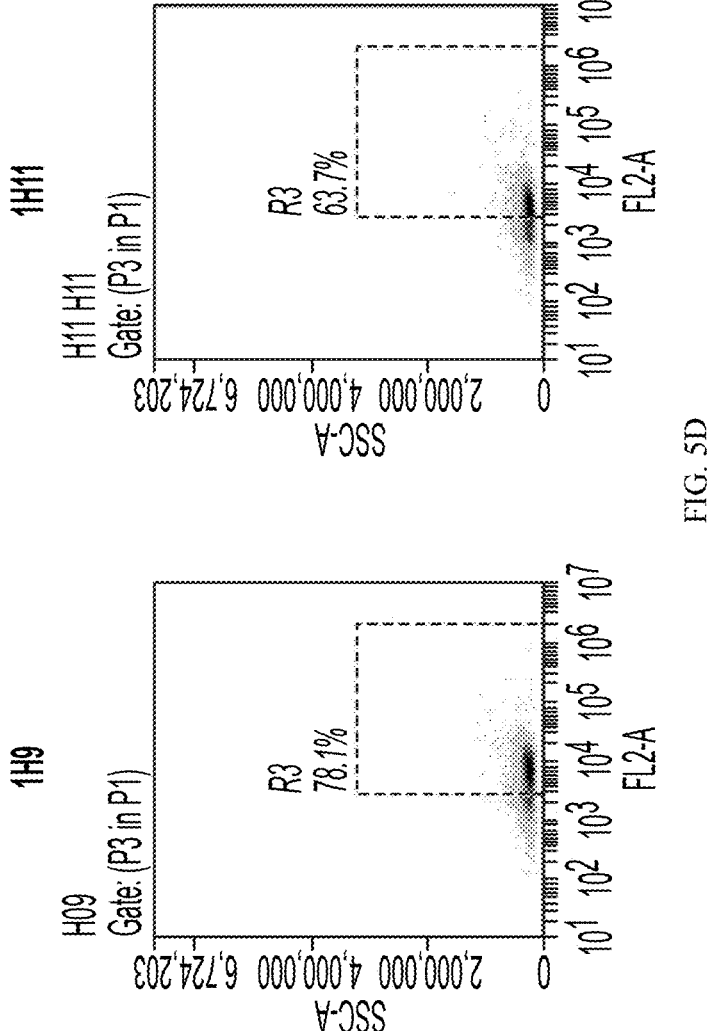
Figures 1, 6A:
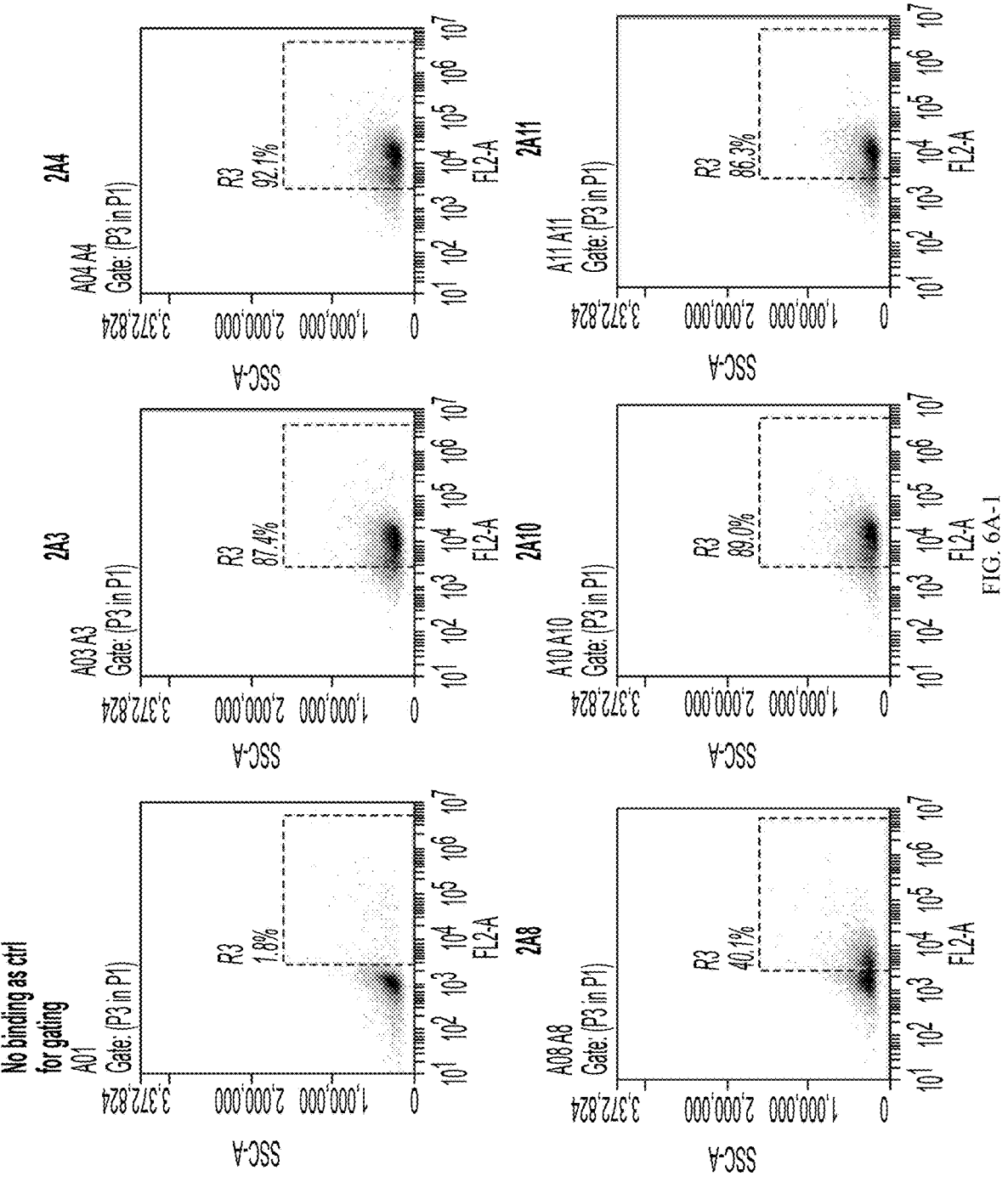
FIGS. 6A-6C show U937 cell binding by certain VHH clones.
Figures 2, 6A:
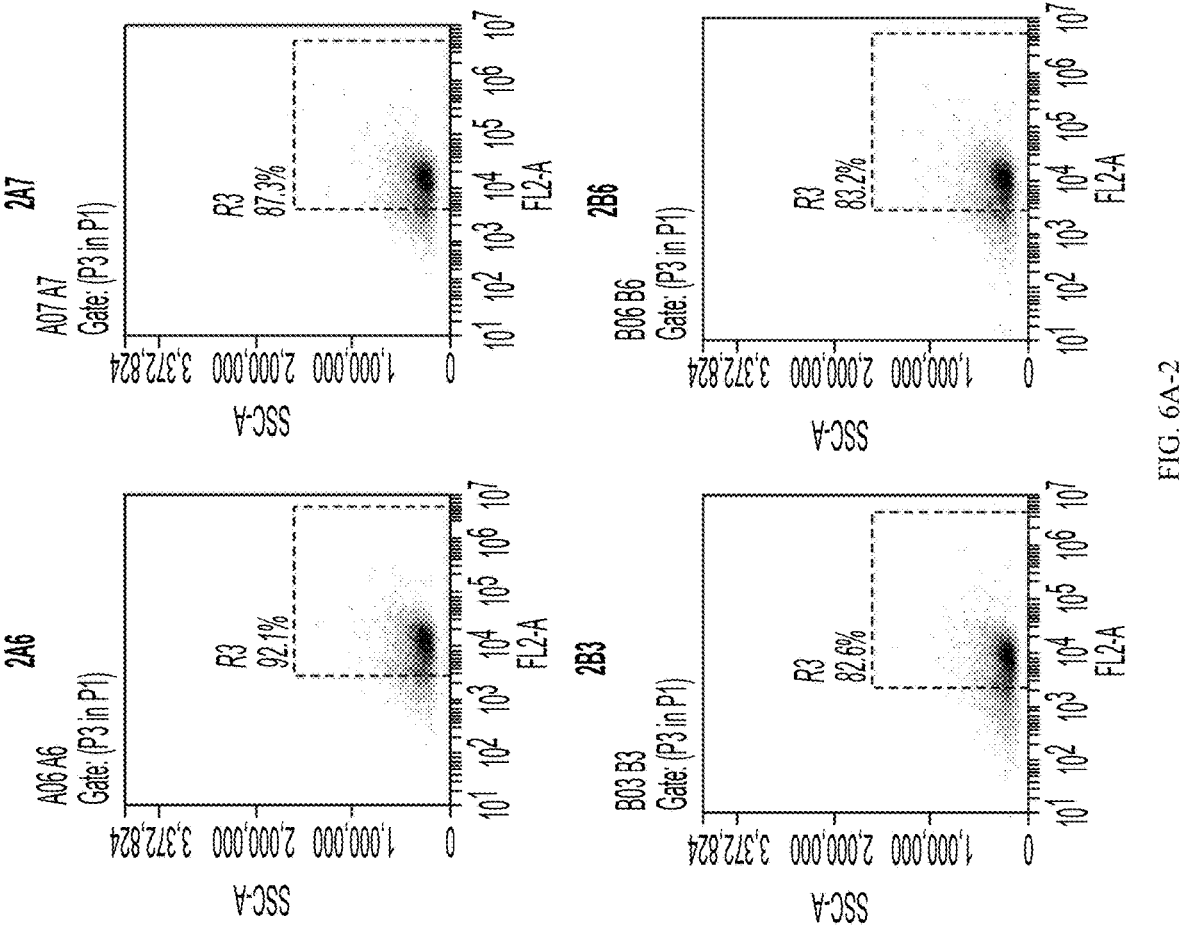
Figures 1, 6B:
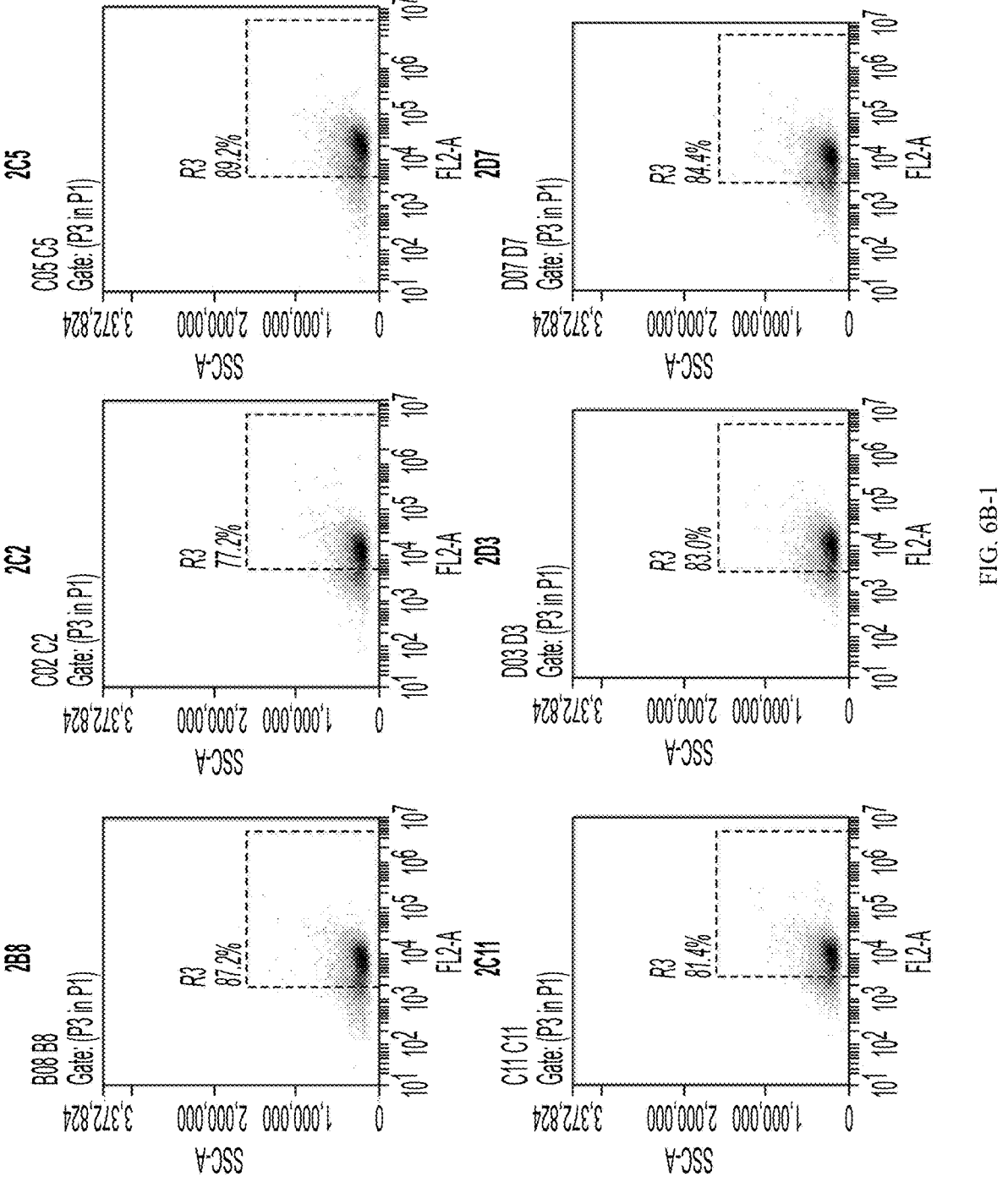
Figure 6B:
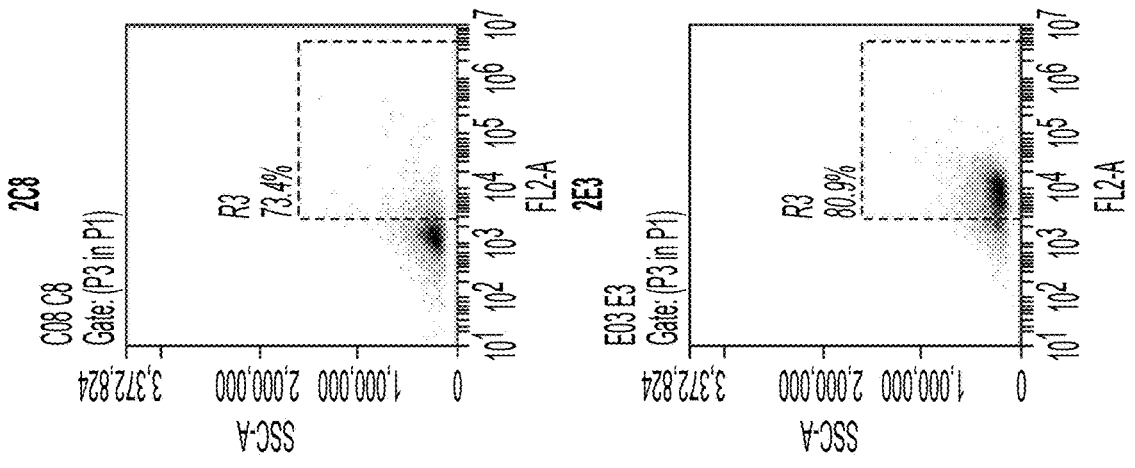
Figure 2:
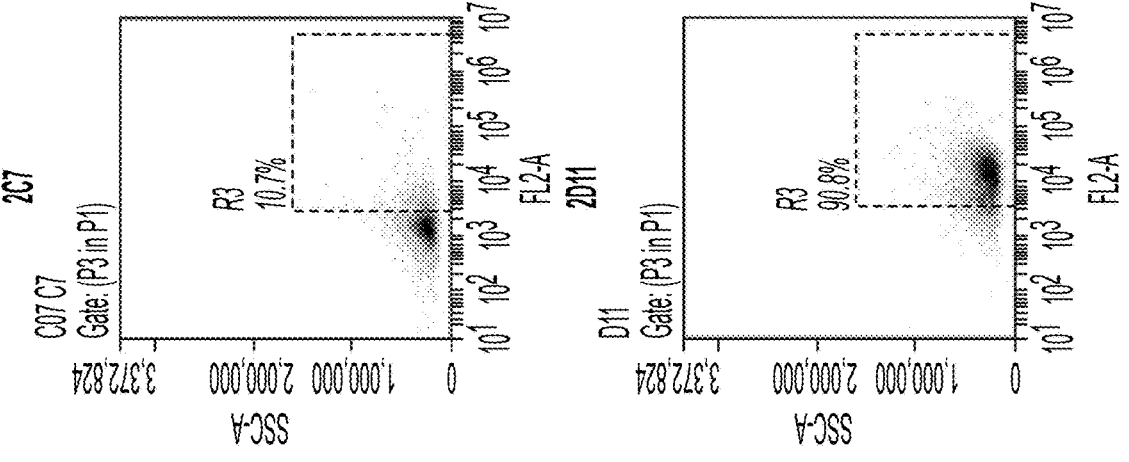
Figures 1, 6C:
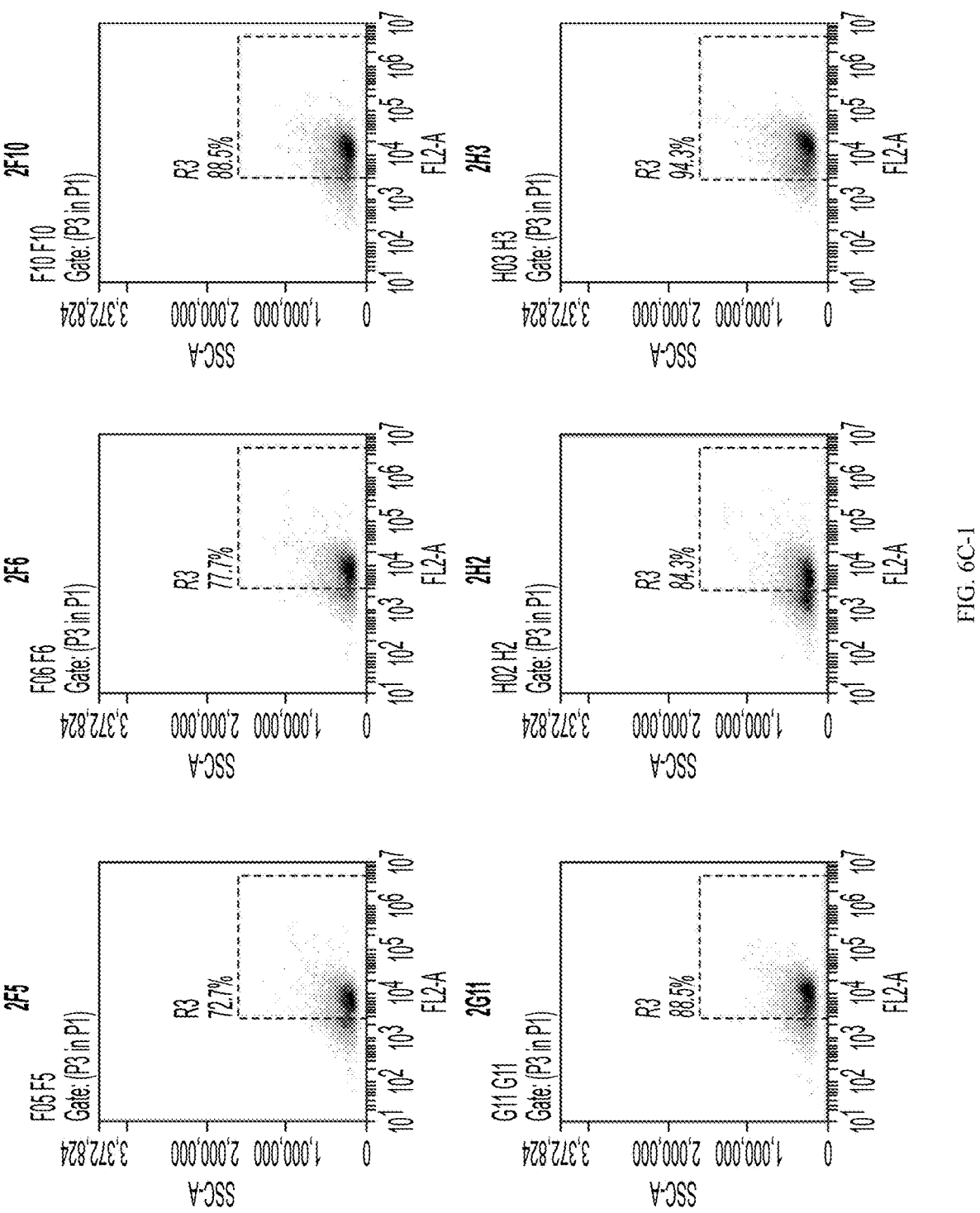
Figures 2, 6C:
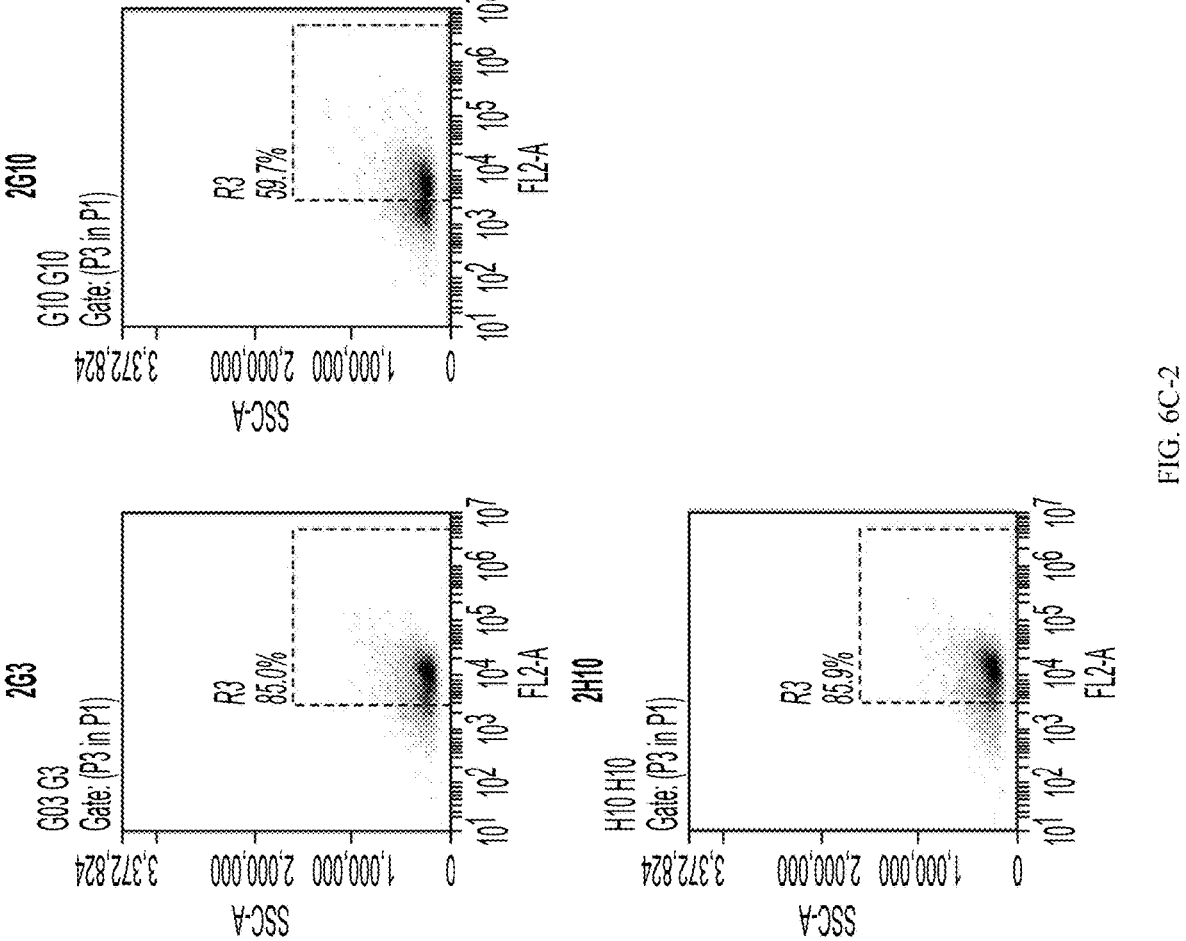
Figure 7B:
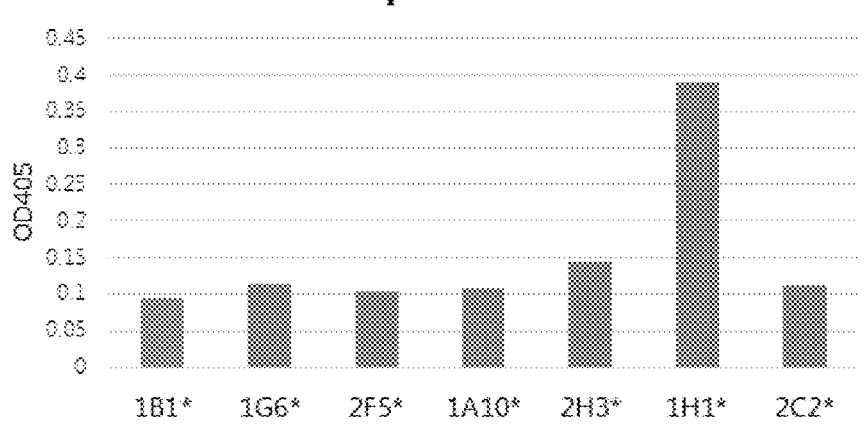
Figure 7B:
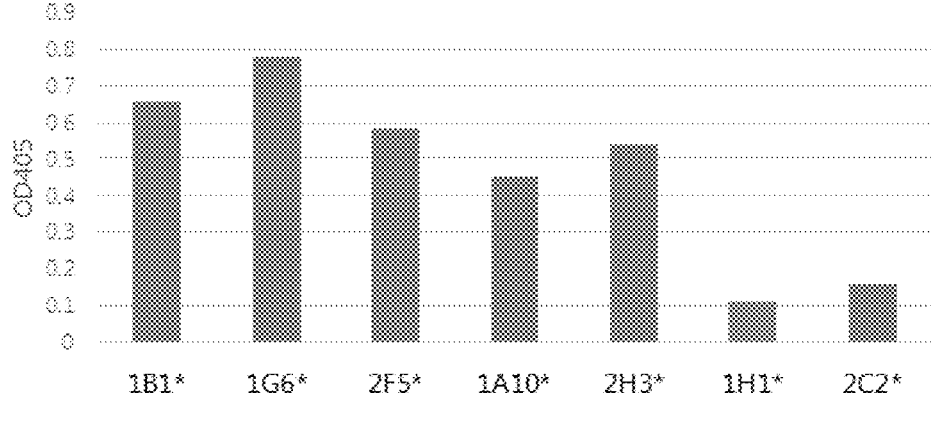
Figure 7C:
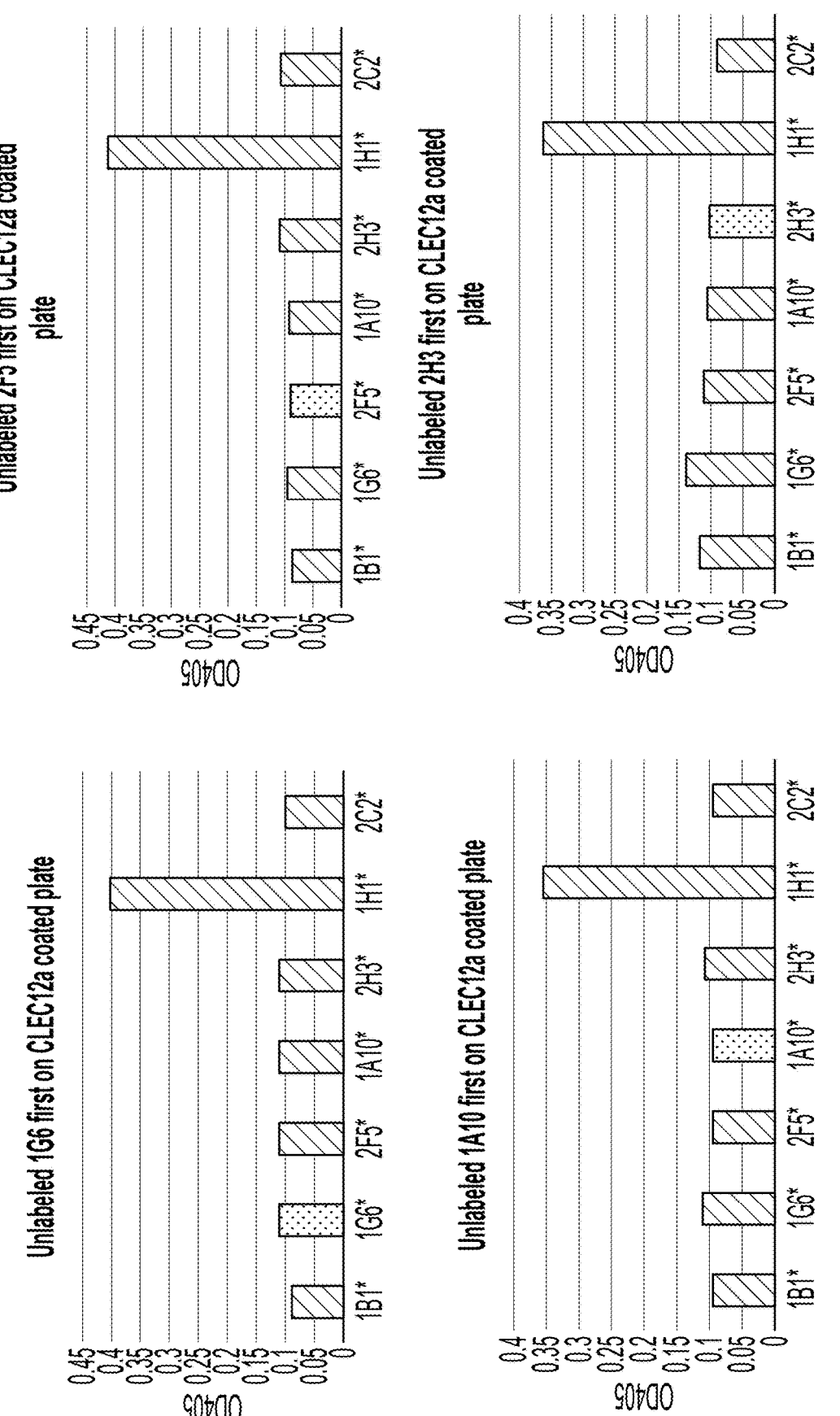
Figure 7D:
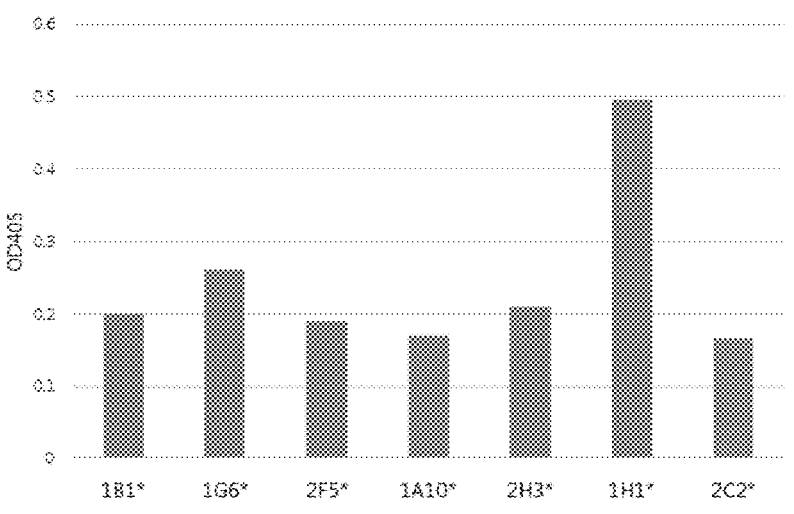

Additional VHH clones were assessed for binding to
U937. Briefly, VHH clones (3 µg/ml as final conc./test) in
FACS buffer were added to Fc blocked U937 cells (2.5×
10^5), the mixtures were incubated for 30 min at 4° C., then
washed twice with FACS buffer by spinning at 500G for 2
min; anti-cMyc (Novus, Cat. #NBP2-37822) was added to
cells, the mixture was incubated for 30 min/4° C. and
washed twice with FACS buffer by spinning at 500G/2 min,
then anti-msIgG-PE (Jackson ImmunoResearch, Cat. #115-
116-146) was added to the cells, the mixture was incubated
for 30 min/4° C. and washed twice with FACS buffer by
spinning at 500G/2 min, 1% PFA (Paraformaldehyde) in
PBS was added to cell pellet to fix the cells, followed by
FACS analysis. Clones tested: 1A10: stock=0.9 mg/ml; 1B1:
stock=0.9 mg/ml; 1C6: stock=1.5 mg/ml; 2C8: stock=0.9
mg/ml; 1D2: stock=0.06 mg/ml. Previous clone as control
2F5: stock=0.5 mg/ml. As shown in FIGS. 4A and 4B, four
clones showed 99% binding on U937 by a-cMyc detection.

An additional plate was screened for clones binding to
U937 cells. Briefly, 10 µl of clone lysate was added to 90 µl
of Fc blocked U937 (2.5×10^5) in FACS buffer, incubated
for 30 min at 4° C., washed twice with FACS buffer by
spinning at 500G for 2 min, a-cMyc-PE (Novus Cat.
NB200-108PE, 1:200 dilution) was added to the cells,
incubated for 30 min at 4° C., washed twice with FACS
buffer by spinning at 500G for 2 min, fixed with 1% PFA in PBS, then analyzed by flow cytometry. As shown in FIGS.
5A-5D, 31 anti-CLL1 positive clones were identified from
96 lysates.

Additional plates were screened for clones binding to
U937 cells. Briefly, 10 µl of clone lysate was added to 90 µl
of Fc blocked U937 (2.5×10^5) in FACS buffer, incubated
for 30 min at 4° C., washed twice with FACS buffer by
spinning at 500G for 2 min, a-cMyc-PE (1:200 dilution) was
added, incubated for 30 min/4° C., washed twice with FACS
buffer by spinning at 500G for 2 min, fixed with 1% PFA in
PBS, then analyzed by flow cytometry. As shown in FIGS.
5A-5D, 31 anti-CLL1 positive clones were identified from
96 lysates from a first plate. As shown in FIGS. 6A-6C, 28
anti-CLL1 positive clones were identified from 96 lysates
from a second plate.

A summary of binding is provided in Table 3:

TABLE 3

| Clone | % FACS positive |
|-------|-----------------|
| 1A4 | 87.6 |
| 1A6 | 91.4 |
| 1A8 | 88.4 |
| 1A9 | 81 |
| 1A10 | 84.9 |
| 1B1 | 87.5 |
| 1B2 | 88.1 |
| 1B3 | 87.8 |
| 1B8 | 88.7 |
| 1B11 | 77.8 |
| 1B12 | 87 |
| 1C2 | 83.9 |
| 1C3 | 88.5 |
| 1C7 | 73 |
| 1C8 | 79.2 |
| 1C9 | 91.1 |
| 1C10 | 79.6 |
| 1D2 | 14.6 |
| 1D6 | 77.7 |
| 1E3 | 50.7 |
| 1E11 | 84.9 |
| 1F2 | 77.9 |
| 1F10 | 72.2 |
| 1G6 | 84.4 |
| 1H1 | 10.8 |
| 1H6 | 77.9 |
| 1H9 | 78.1 |
| 1H11 | 63.7 |
| 2A3 | 87.4 |
| 2A4 | 92.1 |
| 2A6 | 92.1 |
| 2A7 | 83.7 |
| 2A8 | 40.1 |
| 2A10 | 89 |
| 2A11 | 86.3 |
| 2B3 | 82.6 |
| 2B6 | 83.2 |
| 2B8 | 87.2 |
| 2C2 | 77.2 |
| 2C5 | 89.2 |
| 2C7 | 10.7 |
| 2C8 | 73.4 |
| 2C11 | 81.4 |
| 2D3 | 83 |
| 2D7 | 84.4 |
| 2D11 | 90.8 |
| 2E3 | 80.9 |
| 2F5 | 72.7 |
| 2F6 | 77.7 |
| 2F10 | 88.5 |
| 2G3 | 85 |
| 2G10 | 59.7 |
| 2G11 | 88.5 |
| 2H2 | 84.3 |
| 2H3 | 94.3 |
| 2H10 | 85.9 |

ELISAs were used to determine if the VHH clones recognized distinct or similar epitopes. 96 well plates (Pierce Cat. #15041) were coated with 0.1 ug/ml soluble CLEC12a-His (Sino Biological #11896-H07H) in 0.1 M carbonate buffer, pH9.5, O/N at 4C. The plate was blocked with 0.3% nonfat milk in TBS (200 ul/well) for 1 hr at RT. The plates were washed 3× with 1×TBST (0.1M Tris, 0.5M NaCl and 0.05% Tween-20). The test anti-CLEC12a VHHs were added at 10 μg/ml horizontally across the plate, 100 ul per well and incubated for 1h. Without washing, the test anti-CLEC12a biotinylated VHHs were added at 0.2 ug/ml vertically down the plate, 100 ul per well and incubate for 1 h. After being washed 3× with 1×TBST, HRP-conjugated streptavidin (Pierce #21130) at 1:2000 (100 ul/well) was added, followed by incubation at RT in the dark for 1 hr. For detection, 1-Step Ultra TMB-ELISA reagent (Thermo Fisher #34028) was added at 100 ul per well and read at 450 nm. The mapping results indicated that most anti-CLEC12A VHHs recognized the same epitope, except for 1H1 and perhaps 2C2. This indicates that the VHHs from 1B1, IG6 and 2F5 recognize the same epitope as the VHHs from clones that differ in CDR1 (i.e., 1A10 and 2H3). The 1H1 VHH was distinct from these, and 2C2 was intermediate. Results are depicted in FIGS. 7A-7D.

Example 2—Epitope Mapping

One or more of the following methods are used to define the binding epitope for each antibody. Epitopes are either linear or conformational. A linear epitope is composed of a linear stretch of amino acids in the sequence that does not form 3-dimensional structure. A conformational epitope is one that requires tertiary folding to create the proper binding region. Epitope mapping techniques are used for identifying either linear or conformational epitopes. However, linear techniques do not map conformational epitopes. Linear techniques include peptide array scanning, scanning muta-genesis, peptide library phage display and related techniques that define the amino acids found in the linear epitope. These linear techniques are used to map the epitope of antibodies that can bind to a non-conformational part of the antigen, e.g., as is known for antibodies that can bind to denatured proteins that have had their conformations disrupted. Most epitopes are conformational and are defined by using one or more techniques including X-ray co-crystallography, con-formational peptide scanning as can be performed with large peptides displayed on the surface of phage, mutagenesis technologies whereby specific amino acid residues of the antigen are mutated or changed (often to alanine) and the presence of the complex is detected (often with fluorescence, e.g., in FRET assays), a technique that can be automated, i.e., as when many plasmid clones are generated in a library format using computers to perform statistical calculations of the database, cross-link coupled Mass Spectrometry in which the antibody and the antigen are tagged with a mass-labeled chemical crosslinker. The antibody/antigen complex is confirmed using high mass MALDI detection. Once created the antibody/antigen complex is extremely stable, and various enzymes and digestion conditions are applied to the complex to provide many different overlap-ping peptides. Identification of these peptides is performed using high-resolution mass spectrometry and MS/MS tech-niques. Identification of the crosslinked peptides is deter-mined using mass tags linked to the cross-linking reagents. After MS/MS fragmentation and data analysis using specific interaction software, both epitope and paratope are deter-mined in the same experiment. In another technique, Hydro-gen Deuterium Exchange (HDX), the availability of hydro-gen molecules in the backbone of a protein structure is measured. During analysis, both the unbound antigen and the bound antibody-antigen complex are incubated in deu-terated water in order to exchange any hydrogens from exposed amino acids of the protein's backbone. By com-paring the unbound antigen with the bound antibody-antigen complex the residues of the epitope are determined. One or more of these technologies is used to identify linear and conformational epitopes of the VHH antibodies of the inven-tion.

Linear Epitopes

Figure 8:
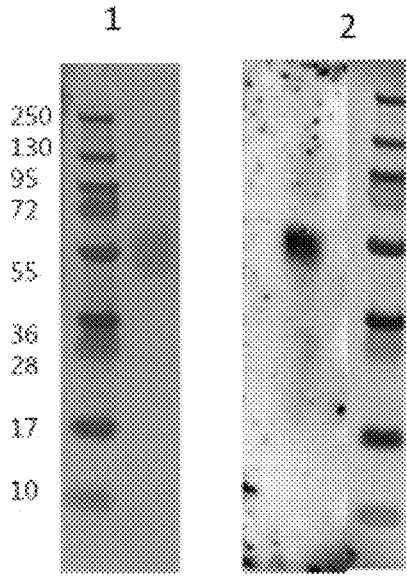
FIG. 8 demonstrates VHH clone 1H1 binds a linear epitope of Clec12A.

To evaluate if any identified VHH clones bind a linear epitope on Clec12A, clones were evaluated for binding denatured Clec12A via Western Blot following SDS-PAGE. To test recognition of Clec12A by the VHH clones, 0.5 μg of Clec12A-His (Sino Biological, 11896-H07H) was run on a 4-12% gradient SDS gel (Invitrogen, NP0321) under reducing conditions. After blotting, using the iBlot 2 system (Invitrogen, IB23002), the membrane was blocked in 5% non-fat milk in Tris buffered saline (TBS) for 1 hr. Next, half the blot was incubated with about 1 μg/ml protein superna-tant of myc tagged anti CLEC12a VHH for 2 hrs followed by 3× wash in wash buffer (lx TBST: 0.1 M Tris, 0.5 M NaCl, 0.05% Tween 20). The blot was then incubated with 1:2000 HRP-anti-Myc (Rockland/Fisher, 50-105-8097) for another 1 hr and washed 3× in wash buffer and then developed using SuperSignal West Femto Maximum Sen-sitivity Substrate (Thermo Fisher, 34095). The other half of the blot was directly incubated with 1:2000 HRP-anti-his (BioLegend/Fisher, 652504) for 1 hr at 0.1 μg/ml and developed as a positive control for the presence of Clec12A on the blot. Only one clone, VHH clone 1H1, was found to bind denatured Clec12A by Western Blot. Results are depicted in FIG. 8.

Figure 9:
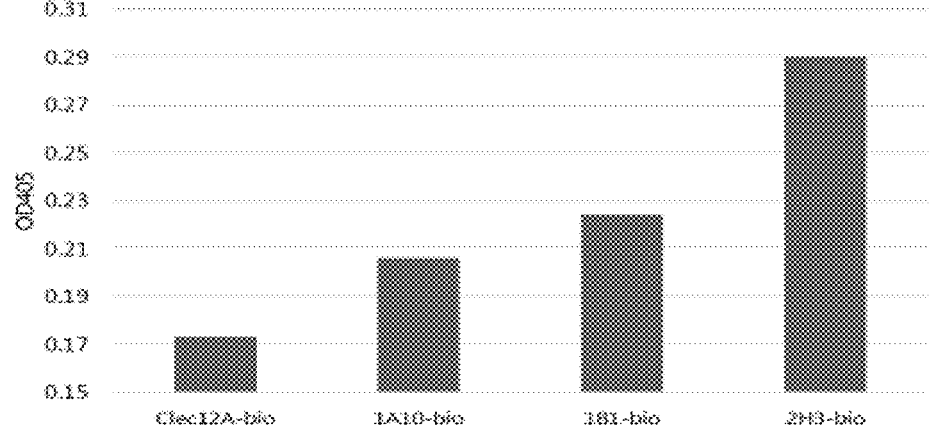
FIG. 9 demonstrates epitope differences between an anti-Clec12A scFv and certain VHH clones.

Example 3—VHH Clones Recognize an Epitope Distinct from Previously Reported Anti-Clec12A scFv To further elucidate epitopes bound by the VHH clones, several VHH clones were tested for their ability to compete for binding with a known anti-Clec12A scFv. A fusion protein comprising the anti-Clec12A scFv SC02-357 described in U.S. Pat. No. 7,741,443 (included herein as SEQ ID NO:26) was immobilized on plastic plates followed by binding of recombinant Clec12A. Three biotinylated VHH clones, 1A10, 1B1, and 2H3, each from the same epitope cluster, and a negative control of biotinylated Clec12A (lane 1), were then evaluated for binding. Each of the three clones was able to bind the Clec12A pre-bound to the anti-Clec12A scFv. This result (FIG. 9) demonstrates that the epitope recognized by the anti-Clec12A scFv is distinct from the epitope recognized by the VHH clones.

Example 4 Binding of VHH Clones to Clec12A Variants

The ability of VHH clones to recognize commercially available recombinant Clec12a proteins was tested by ELISA. Briefly, a 96 well plate (Pierce, 15041) was coated with 1.0 ug/ml Clec12A (Sino Biological, 11896-H07H or ABclonal, RP01018) in 0.1 M carbonate, pH9.5 overnight at 4° C. The plate was blocked with 200 μl/well 0.3% non-fat milk in Tris buffered saline (TBS) for 1 hr at room tem-perature (RT). Then, the plates were washed 3× with wash buffer (1×TBST: 0.1 M Tris, 0.5 M NaCl, 0.05% Tween 20).

Figure 10A:
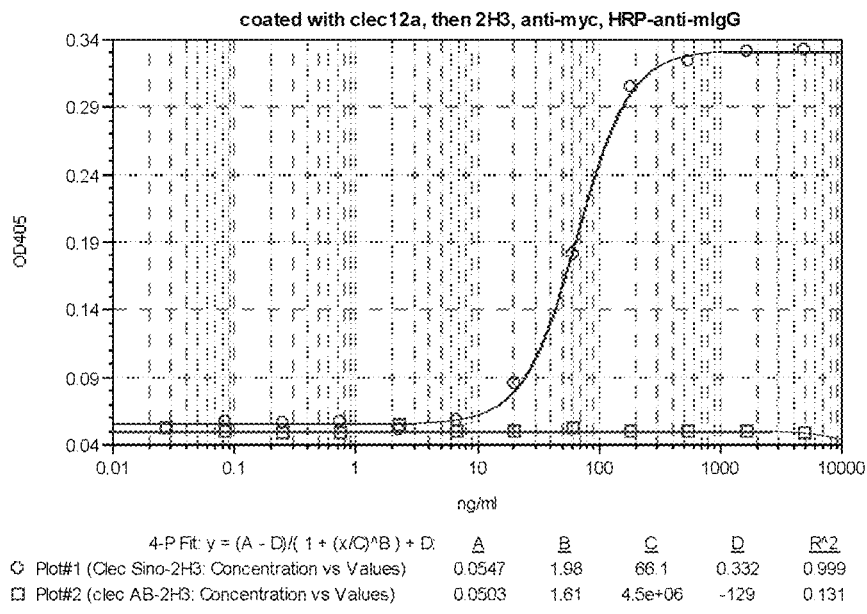
FIGS. 10A and 10B demonstrate the ability of VHH clone 2H3 to recognize recombinant Clec12A proteins.
Figure 10A:
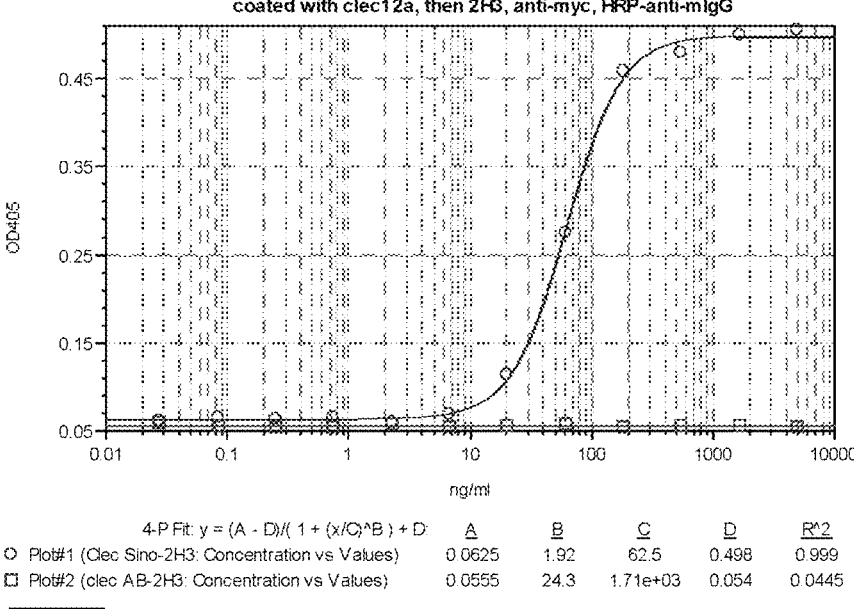

Next, 100 μl of the 2H3 VHH-Myc-His (SEQ ID NO: 15, purified by ProSci), was added starting at 5 μg/ml with 3 fold dilutions, and incubated for 1h at RT. The plate was washed 3× with wash buffer and 100 μl of 1 μg/ml anti-Myc antibody (NOVUS/Fisher, NBP2-37822) was added per well. The plate was incubated for 1h at RT and then washed 3× with wash buffer. Following the wash step, 100 μl of a 1:2000 dilution of HRP-anti-mIgG (Jackson ImmunoResearch, 115-035-062) was added per well and incubated at RT in the dark for 1 hr. For detection, 100 μl of 1-Step Ultra TMB-ELISA from Thermo Fisher, 34028 was added per well and then the plate was read at 405 nM when the color developed. This experiment was repeated twice. Graphs for each experiment were generated using the Softmax software and are shown in FIG. 10A.

Figure 10B:
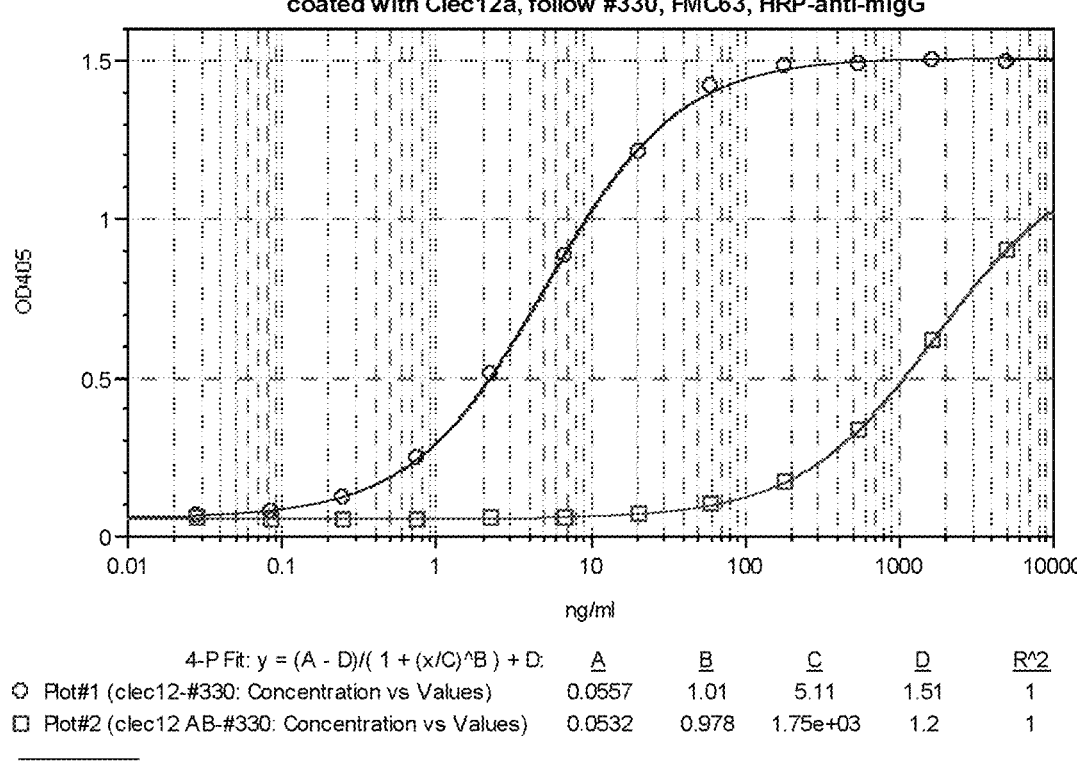

In a second ELISA, the plate was coated with the Clec12A proteins as above, but instead of probing with the 2H3 VHH, a 2H3 VHH-G4Sx4-CD19-His fusion protein was added starting at 5 μg/ml with 3 fold dilutions. Also, instead of the anti-Myc reagent, the anti-CD19 Ab FMC63 was added at 1 μg/ml conc. After washing, the protocol using the HRP anti-mIgG reagent was followed as above. Graphs were generated using the Softmax software and are shown in FIG. 10B.

It is understood that commercially available recombinant Clec12A proteins have an added six histidine tag (SEQ ID NO: 33) to allow for easy analysis. The Clec12A from Sino Biological has the HIS tag at the N-terminus, while the Clec12A from ABclonal has the HIS tag at the C-terminus. We found that VHH clone 2H3 bound immobilized Sino Biological Clec12A but not immobilized ABelonal Clec12A (see FIG. 10A). It is possible that the epitope for the VHH cluster containing 2H3 bound close to the C-terminus, i.e. that the added C-terminal HIS tag might be interfering with binding. It should be noted that Clec12A is a Type II membrane protein, i.e. the C-terminus is extracellular. To obviate potential problems with direct binding of the Clec12A to plastic (FIG. 4A), the Clec12A's from each source were also immobilized using an anti-Clec12A antibody immobilized on plastic plates first, which gave similar results (FIG. 10B).

To further investigate whether the observed difference in binding was caused by the HIS tag at the C-terminus interfering with binding of clone 2H3 we reviewed the amino acid sequences of the two recombinant Clec12A proteins. We discovered that there are two forms of Clec12A with a single amino acid difference in this region. The canonical sequence (UniProt; Q5QGZ9-1) contains a Lysine (K in bold underline; SEQ ID NO:27).

```
                                          (SEQ ID NO: 27)
MWIDFFTYSSMSEEVTYADLQFQNSSEMEKIPEIGKFGEKAPPAPSHVWR

PAALFLTLLCLLLLIGLGVLASMFHVTLKIEMKKMNKLQNISEELQRNIS

LQLMSNMNISNKIRNLSTTLQTIATKLCRELYSKEQEHKCKPCPRRWIWH

KDSCYFLSDDVQTWQESKMACAAQNASLLKINNKNALEFIKSQSRSYDYW

LGLSPEEDSTRGMRVDNIINSSAWVIRNAPDLNNMYCGYINRLYVQYYHC

TYKKRMICEKMANPVQLGSTYFREA
```

However, the Sino Biological sequence (GenBank: EAW96132.1) has a Glutamine instead (Q in in bold underline; SEQ ID NO:28).

```
                                          (SEQ ID NO: 28)
MWIDFFTYSSMSEEVTYADLQFQNSSEMEKIPEIGKFGEKAPPAPSHVWR

PAALFLTLLCLLLLIGLGVLASMFHVTLKIEMKKMNKLQNISEELQRNIS

LQLMSNMNISNKIRNLSTTLQTIATKLCRELYSKEQEHKCKPCPRRWIWH

KDSCYFLSDDVQTWQESKMACAAQNASLLKINNKNALEFIKSQSRSYDYW

LGLSPEEDSTRGMRVDNIINSSAWVIRNAPDLNNMYCGYINRLYVQYYHC

TYKQRMICEKMANPVQLGSTYFREA
```

Upon evaluation of binding to other Clec12A sequences we found that VHH clone 2H3 did not bind a Clec12A from AbClonal (NCBI Reference Sequence: NP_001193939.1, isoform3) or a cDNA from Genscript both of which contain a Lysine residue at amino acid 254. This suggests that the K/Q amino-acid is within or close to the 2H3 epitope, and is consistent with the 2H3 epitope being close to the C-terminus. In contrast the scFv binds to both protein variants.

Example 5—Mass Spectrometry Based Epitope Identification

Figure 11A:
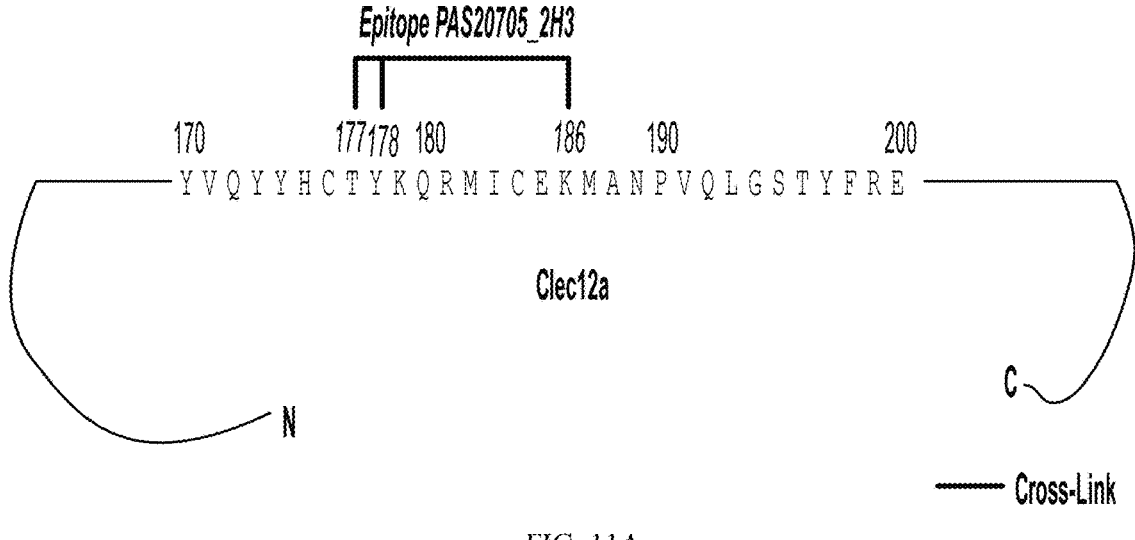
FIGS. 11A and 11B demonstrate mass spectrometry identified epitopes of an anti-Clec12A scFv and VHH clone 2H3 (Note: amino acid numbering in figure based on only extracellular domain amino acids (i.e., the 200 amino acids 65-25 of the full length sequence).
Figure 11B:
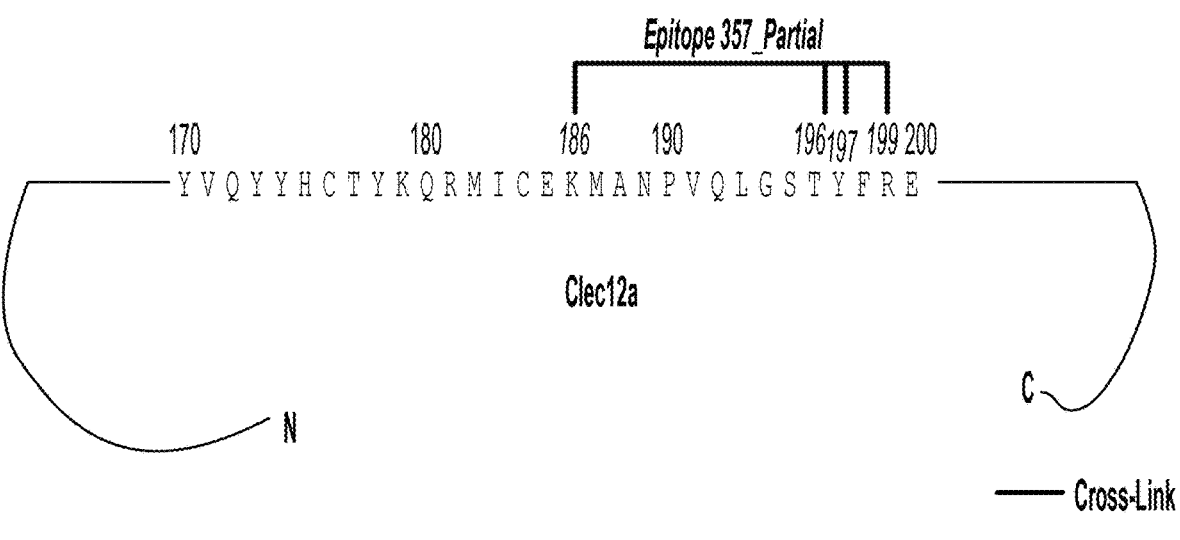

To further define the epitopes of the scFv and VHH 2H3, we used a commercially available process (CovalX), which covalently cross-links the binders to the target, then uses mass spectrometry to define the binding sites. By mixing a protein sample containing non-covalent interactions with a specially developed cross-linking mixture (Bich, C et al. Anal. Chem., 2010, 82 (1), pp 172-179), it is possible to specifically detect non-covalent complex with high-sensitivity. The covalent binding generated allows the interacting species to survive the sample preparation process and the MALDI ionization. A special High-Mass detection system allows characterizing the interaction in the High-Mass range. FIG. 11A shows the amino acids crosslinked between 2H3 and Clec12A defining the region of the 2H3 epitope. Amino acids 251 (T); 252 (Y); and 260 (K) (based on full length Clec12A SEQ ID NO 28) were identified as cross linked. The epitope spans the region containing the K/Q variant, entirely consistent with a change in charge in this region (K vs. Q) disrupting the 2H3 epitope as suggested in Example 3. FIG. 11B shows the epitope for the SC02-357 scFv. Again, its presence near the C-terminal is consistent with all other results, i.e., a distinct epitope from 2H3, yet within the last 50 AA of Clec12A.

Example 6—Specificity of Binding

To examine binding to proteins related to Clec12A, family members with the highest degree of homology were determined. Clec1A and Clec12B were the most related with identity in their extracellular domains of 36% and 32%, respectively. Expression plasmids for C terminal Flag tagged Clec12A (OHu09814D), Clec12B (OHu13983B) and Clec1A (OHu27138D) were purchased from GenScript. They were transfected into 293T cells using 2 μg plasmid and 10 μl of lipofectamine 2000 (Invitrogen, 11668019) per well (6 well plate) using the manufacturer's protocol. After 48 hrs, the cells were removed using Accutase (Thermo Fisher, 00-4555-56) and washed with PBS. The cells were then blocked for 10 minutes with human Fc-Block (BD Biosciences, 564219). Fc-blocked 293T-Clec12A; Clec12B; or Clec1A cells were resuspended in 50 μl FACs buffer (PBS/1% BSA/0.1% Sodium Azide) and then added to 50 μl of a 2H3VHH-CD19-His fusion protein (His Trap Excel (GE Healthcare, 17-3712 purified) serially diluted in FACS buffer, starting at 5 µg/ml, final concentration. The sequence of the 2H3 VHH used is a version of SEQ ID NO: 15 lacking the C-terminal myc and His tags disclosed in SEQ ID 29 Serial dilutions were done in 3-fold steps. The cells and the 2H3VHH-CD19 fusion protein were incubated together for 30 minutes at 4° C. The samples were washed in FACS buffer and centrifuged at 500 RCF at 4° C. for 2 minutes. This wash step was repeated and then the cells were resuspended in FACs buffer containing 2.5 µg/ml PE-labeled FMC63 (MilliporeSigma, MAB1794H). After incubation for 30 minutes at 4° C., the cells were washed twice as described resuspended in 150 µl PBS/1% paraformaldehyde to fix the cells. Expression of the Clec receptors was verified by staining the transfected cells with 5 µl anti-Flag-APC reagent (BioLegend, 637307) per sample. After 30 minutes

Figure 12:
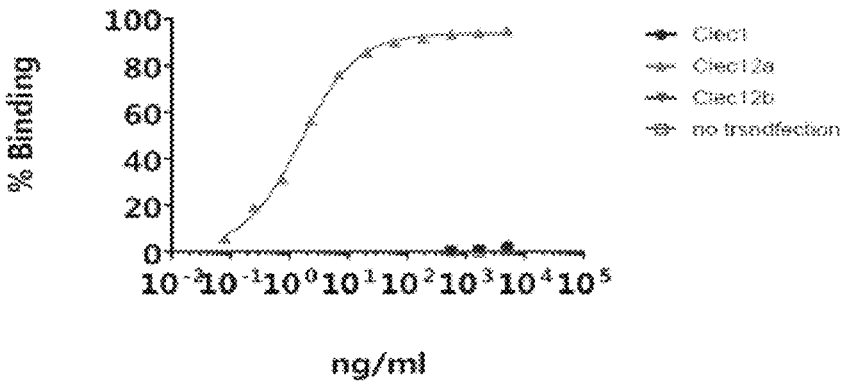
FIG. 12 shows VHH clone 2H3 binds specifically to Clec12A.

38 at 4° C., the samples were washed and fixed as above. Cell samples data were collected by flow cytometry (BD Accuri 6) and analyzed using BD Accuri 6 software. It was determined that the fusion protein containing the VHH 2H3 only bound to Clec12A expressing cells (FIG. 12).

Other Embodiments

While a number of embodiments of this invention are described herein, the present disclosure and examples may be altered to provide other methods and compositions of this invention. Therefore, it will be appreciated that the scope of this invention is to be defined by the appended claims in addition to the specific embodiments that have been represented by way of example. All references cited herein are hereby incorporated by reference.

```
LISTING OF SEQUENCES
                                                    SEQ ID NO: 1
atgtctgaag aagttactta tgcagatctt caattccaga actccagtga gatggaaaaa    60
atcccagaaa ttggcaaatt tggggaaaaa gcacctccag ctccctctca tgtatggcgt   120
ccagcagcct tgtttctgac tcttctgtgc cttctgttgc tcattggatt gggagtcttg   180
gcaagcatgt ttcatgtaac tttgaagata gaaatgaaaa aaatgaacaa actacaaaac   240
atcagtgaag agctccagag aaatatttct ctacaactga tgagtaacat gaatatctcc   300
aacaagatca ggaacctctc caccacactg caaacaatag ccaccaaatt atgtcgtgag   360
ctatatagca aagaacaaga gcacaaatgt aagccttgtc caaggagatg gatttggcat   420
aaggacagct gttatttcct aagtgatgat gtccaaacat ggcaggagag taaaatggcc   480
tgtgctgctc agaatgccag cctgttgaag ataaacaaca aaaatgcatt ggaatttata   540
aaatcccaga gtagatcata tgactattgg ctgggattat ctcctgaaga agattccact   600
cgtggtatga gagtggataa tataatcaac tcctctgcct gggttataag aaacgcacct   660
gacttaaata acatgtattg tggatatata aatagactat atgttcaata ttatcactgc   720
acttataaac aaagaatgat atgtgagaag atggccaatc cagtgcagct tggttctaca   780
tattttaggg aggcatgagg c                                             801

SEQ ID NO: 2
Met Ser Glu Glu Val Thr Tyr Ala Asp Leu Gln Phe Gln Asn Ser Ser
1               5                   10                  15

Glu Met Glu Lys Ile Pro Glu Ile Gly Lys Phe Gly Glu Lys Ala Pro
20                  25                  30

Pro Ala Pro Ser His Val Trp Arg Pro Ala Ala Leu Phe Leu Thr Leu
35                  40                  45

Leu Cys Leu Leu Leu Leu Ile Gly Leu Gly Val Leu Ala Ser Met Phe
50                  55                  60

His Val Thr Leu Lys Ile Glu Met Lys Lys Met Asn Lys Leu Gln Asn
65                  70                  75                  80

Ile Ser Glu Glu Leu Gln Arg Asn Ile Ser Leu Gln Leu Met Ser Asn
85                  90                  95

Met Asn Ile Ser Asn Lys Ile Arg Asn Leu Ser Thr Thr Leu Gln Thr
100                 105                 110

Ile Ala Thr Lys Leu Cys Arg Glu Leu Tyr Ser Lys Glu Gln Glu His
115                 120                 125

Lys Cys Lys Pro Cys Pro Arg Arg Trp Ile Trp His Lys Asp Ser Cys
130                 135                 140

Tyr Phe Leu Ser Asp Asp Val Gln Thr Trp Gln Glu Ser Lys Met Ala
145                 150                 155                 160
```

-continued

```
Cys Ala Ala Gln Asn Ala Ser Leu Leu Lys Ile Asn Asn Lys Asn Ala
165                 170                 175

Leu Glu Phe Ile Lys Ser Gln Ser Arg Ser Tyr Asp Tyr Trp Leu Gly
180                 185                 190

Leu Ser Pro Glu Glu Asp Ser Thr Arg Gly Met Arg Val Asp Asn Ile
195                 200                 205

Ile Asn Ser Ser Ala Trp Val Ile Arg Asn Ala Pro Asp Leu Asn Asn
210                 215                 220

Met Tyr Cys Gly Tyr Ile Asn Arg Leu Tyr Val Gln Tyr Tyr His Cys
225                 230                 235                 240

Thr Tyr Lys Lys Arg Met Ile Cys Glu Lys Met Ala Asn Pro Val Gln
245                 250                 255

Leu Gly Ser Thr Tyr Phe Arg Glu Ala
260                 265
```

SEQ ID NO: 3 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQESGGGLVQAGGSLRLSCAASGSIFAINEINLMGWYRQAPGKQRELVAACASDG

NTYYADSVKGRFTISRDNAEKTVYLQMNNLKPDDTAVYYCDANSRGNYYSGQGTQVT

VSS*TSGPGGQGAEQKLISEEDLGAHHHHHHGAS*

SEQ ID NO: 4 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQESGGGLVQAGGSLRLSCAASGSIFAINEINLMGWYRQAPGKQRELVAACASDG

NTYYADSVKGRFTISRDNAEKTVYLQMNNLKPDDTAVYYCDANSRGNYYSGQGTLVT

VSS*TSGPGGQGAEQKLISEEDLGAHHHHHHGAS*

SEQ ID NO: 5 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQQSGGGLVQAGGSLRLSCAASGSIFAINEINLMGWYRQAPGKQRELVAACASDG

NTYYADSVKGRFTISRDNAEKTVYLQMNNLKPDDTAVYYCDANSRGNYYSGQGTQVT

VSS*TSGPGGQGAEQKLISEEDLGAHHHHHHGAS*

SEQ ID NO: 6 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQQSGGGLVQAGGSLRLSCAASGSIFAINEINLMGWYRQAPGKQRELVAACASDG

NTYYADSVKGRFTISRDNAEKTVYLQMNNLKPDDTAVYYCDANSRGNYYSGQGTLVT

VSS*TSGPGGQGAEQKLISEEDLGAHHHHHHGAS*

SEQ ID NO: 7 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQQFGGGLVQAGGSLRLSCAASGSIFAINEINLMGWYRQAPGKQRELVAACASDG

NTYYADSVKGRFTISRDNAEKTVYLQMNNLKPDDTAVYYCDANSRGNYYSGQGTLVT

VSS*TSGPGGQGAEQKLISEEDLGAHHHHHHGAS*

SEQ ID NO: 8 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*

-continued

*(SEQ ID NO: 33)), and (v) an additional 3 amino acids (GAS)):*
QVQLQASGGGLVQAGGSLRLSCAASGSIFAINEINLMGWYRQAPGKQRELVAACASDG

NTYYADSVKGRFTISRDNAEKTVYLQMNNLKPDDTAVYYCDANSRGNYYSGQGTQVT

VSS*TSGPGGQGAEQKLISEEDLGAHHHHHHGAS*

SEQ ID NO: 9 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQEFGGGLVQAGGSLRLSCAASGSIFAINEINLMGWYRQAPGKQRELVAACASDG

NTYYADSVKGRFTISRDNAEKTVYLQMNNLKPDDTAVYYCDANSRGNYYSGQGTLVT

VSS*TSGPGGQGAEQKLISEEDLGAHHHHHHGAS*

SEQ ID NO: 10 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQEFGGGLVQAGGSLRLSCAASGSIFAINEINLMGWYRQAPGKQRELVAACASDG

NTYYADSVKGRFTISRDNAEKTVYLQMNNLKPDDTAVYYCDANSRGNYYSGQGTQVT

VSS*TSGPGGQGAEQKLISEEDLGAHHHHHHGAS*

SEQ ID NO: 11 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLVESGGGLVQAGGSLRLSCAASGSIFAINEINLMGWYRQAPGKQRELVAACASDG

NTYYADSVKGRFTISRDNAEKTVYLQMNNLKPDDTAVYYCDANSRGNYYSGQGTLVT

VSS*TSGPGGQGAEQKLISEEDLGAHHHHHHGAS*

SEQ ID NO: 12 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQQSGGGLAQTGGSLILSCAASGSIFAINEINLMGWYRQAPGKQRELVAACASDGN

TYYADSVKGRFTISRDNAEKTVYLQMNNLKPDDTAVYYCDANSRGNYYSGQGTQVTV

SS*TSGPGGQGAEQKLISEEDLGAHHHHHHGAS*

SEQ ID NO: 13 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQESGGGLVQPGGSLRLSCAASGSIFAINEINLMGWYRQAPGKQRELVAACASDG

NTYYADSVKGRFTISRDNAEKTVYLQMNNLKPDDTAVYYCDANSRGNYYSGQGTLVT

VSS*TSGPGGQGAEQKLISEEDLGAHHHHHHGAS*

SEQ ID NO: 14 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQESGGGLVQVGESLRLSCVVSGDTRSINLMGWYRQAPGKQRELVAACASDGNT

YYADSVKGRFTISRDNAEKTVYLQMNNLKPDDTAVYYCDANSRGNYYSGQGTLVTVS

S*TSGPGGQGAEQKLISEEDLGAHHHHHHGAS*

SEQ ID NO: 15 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*

-continued

*(iii) a linker of 2 amino acids (GA), (iv) a hexa-histidine tag (HHHHHH*
*(SEQ ID NO: 33)), and (v) an additional 3 amino acids (GAS)):*
QVQLQESGGGLVQAGGSLRLSCVASGSIRSINVMGWYRQAPGKQRELVAACASDGNTY

YADSVKGRFTISRDNAEKTVYLQMNNLKPDDTAVYYCDANSRGNYYSGQGTQVTVSS

*TSGPGGQGAEQKLISEEDLGAHHHHHHGAS*

SEQ ID NO: 16 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQESGGGLVQPGGSLRLSCAASGFTFNSYAMTWVRQAPGKGLEWVSDINSGGGST

NYADSVKGRFTISRDNAKNTLYLQMNSLKPEDTAVYYCATELRGSDYYRGPIREYAYW

GQGTLVTVSS*TSGPGGQGAEQKLISEEDLGAHHHHHHGAS*

SEQ ID NO: 17 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQESGGALVQAGGSLRLSCAASGLTFSNYAMGWFRQAPGKEREFVAAINWSGGT

TDYATSVKGRFTISRDNAKNTVYLQLNSLKPEDTAVYYCAASYRLRITVVVTPDEYHY

WGQGTLVTVSS*TSGPGGQGAEQKLISEEDLGAHHHHHHGAS*

SEQ ID NO: 18 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQQSGGGLVQPGGSLRLSCAASGFAFDDYAMIWVRQGPGKGLEWVSSISWNGGG

TYYAESIVGRFTVSRDNAKKMVYLQMNGLKSEDTAMYYCVKLVDSGWYSAYDYWGQ

GTQVTVSS*TSGPGGQGAEQKLISEEDLGAHHHHHHGAS*

SEQ ID NO: 19 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQESGGGLVQAGGSLRLSCVVSGATSNVNAMGWYRQAPGKERELVAAISSGGSTS

YRDSVKGRFTISRDNAKNTLYLQMNSLKPEDTAMYYCAAQDWATEGYEYDYWGQGT

LVTVSS

SEQ ID NO: 20 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQAFGGGLVQPGGSLRLSCVVSGTMFSGKDVNWLRQAPGKHVEVVATVSSDGGT

DYADFVKGRFTISRDDAKNTVNLQMNSLEPEDTANYMCHFLWGRHYWGQGTQVTVSS

*TSGPGGQGAEQKLISEEDLGAHHHHHHGAS*

SEQ ID NO: 21 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*
*(iii) a linker of 2 amino acids (GA), (iv) a hexa-histidine tag (HHHHHH*
*(SEQ ID NO: 33)), and (v) an additional 3 amino acids (GAS)):*
QVQLQAFGGGMVQAGESLRLSCVASGNDISGSAMAWYRAHLGAERELVAVDAPRERP

FYIDPVIGRFTISRDDRNKMLYLQMNDLRPDDTATYWCGPSLRTFHGREWYRPPWFTS

WGQGTQVTVSS*TSGPGGQGAEQKLISEEDLGAHHHHHHGAS*

SEQ ID NO: 22 (underlining denotes CDR1, CDR2, CDR3, sequentially;
*bolded italics at C-terminus denotes (i) a linker of 9 amino acids*
*(TSGPGGQGA SEQ ID NO: 31), (ii) a myc-tag (EQKLISEEDL SEQ ID NO: 32)),*

<div align="center">-continued</div>

*(iii) a linker of 2 amino acids (GA), (iv) a hexa-histidine tag (HHHHHH (SEQ ID NO: 33)), and (v) an additional 3 amino acids (GAS)):*
QVQLQQSGGGLVQAGGSLRLSCAASGSIFSINAMGWYRQAPGKRREMVAVVSRFGETT

YTGSVKGRFTISRINRNNTVFLQMNRLKPEDTAVYYCNARIRGNYGSRIDYWGQGTQV

TVSS*TSGPGGQGAEQKLISEEDLGAHHHHHHGAS*

SEQ ID NO: 23 (underlining denotes CDR1, CDR2, CDR3, sequentially;
***bolded italics at C-terminus denotes (i) a linker of 9 amino acids
(TSGPGGQGA SEQ ID NO: 31), (ii) a myc-tag (EQKLISEEDL SEQ ID NO: 32)),
(iii) a linker of 2 amino acids (GA), (iv) a hexa-histidine tag (HHHHHH
(SEQ ID NO: 33)), and (v) an additional 3 amino acids (GAS)):***
QVQLQEFGGGLVQLGGSARLSCVVSGNIVILDLNTMAWYRQGELVAALGISTYYAESVK

GRFTISRDNAKNTLYLQMNSLKSEDTAVYYCARDYNFESWGQGTLVTVSS*TSGPGGQGAEQKLI*

*SEEDLGAHHHHHHGAS*

SEQ ID NO: 24 (underlining denotes CDR1, CDR2, CDR3, sequentially;
***bolded italics at C-terminus denotes (i) a linker of 9 amino acids
(TSGPGGQGA SEQ ID NO: 31), (ii) a myc-tag (EQKLISEEDL SEQ ID NO: 32)),
(iii) a linker of 2 amino acids (GA), (iv) a hexa-histidine tag (HHHHHH
(SEQ ID NO: 33)), and (v) an additional 3 amino acids (GAS)):***
AVQLQESGGGLVQAGGSLRLSCAASGSDRSINVMNWYRQAPGKQRELVAAITSGGTTN

YAQSVKGRVTISRDSAKNTVYLQMNSLKPEDTAVYFCKADTRWGGMYWGPGTQVTV

SS*TSGPGGQGAEQKLISEEDLGAHHHHHHGAS*

SEQ ID NO: 25 (underlining denotes CDR1, CDR2, CDR3, sequentially;
***bolded italics at C-terminus denotes (i) a linker of 9 amino acids
(TSGPGGQGA SEQ ID NO: 31), (ii) a myc-tag (EQKLISEEDL SEQ ID NO: 32)),
(iii) a linker of 2 amino acids (GA), (iv) a hexa-histidine tag (HHHHHH
(SEQ ID NO: 33)), and (v) an additional 3 amino acids (GAS)):***
QVQLQQSGGGLVQAGGSLTLSCAATGRTIDNGAMAWFRQAPGKQRELVAAINWSGGA

TFYTDSVKYRFTISRDNVRHTLDLQMTSLKPEDTTIYFCASRRGVDLRRNSYEYDYWGR

GTLVTVSS*TSGPGGQGAEQKLISEEDLGAHHHHHHGAS*

SEQ ID NO: 26:
QVQLQESGPGLVKPSETLSLTCVVSGGSISSSNWWSWVRQPPGKGLEWIGEIYHSGSPD

YNPSLKSRVTISVDKSRNQFSLKLSSVTAADTAVYYCAKVSTGGFFDYWGQGTLVTVSS

GGGGSGGGGSGGGGSEIELTQSPSSLSASVGDRVTITCRASQSISSYLNWYQQKPGKAPK

LLIYAASSLQSGVPSRFSGSGSGTDFTLTISSLQPEDFATYYCQQSYSTPPTFGPGTKVEIK

SEQ ID NO: 27
MWIDFFTYSSMSEEVTYADLQFQNSSEMEKIPEIGKFGEKAPPAPSHVWRPAALFLTLLC

LLLLIGLGVLASMFHVTLKIEMKKMNKLQNISEELQRNISLQLMSNMNISNKIRNLSTTL

QTIATKLCRELYSKEQEHKCKPCPRRWIWHKDSCYFLSDDVQTWQESKMACAAQNASL

LKINNKNALEFIKSQSRSYDYWLGLSPEEDSTRGMRVDNIINSSAWVIRNAPDLNNMYC

GYINRLYVQYYHCTYKKRMICEKMANPVQLGSTYFREA

SEQ ID NO: 28.
MWIDFFTYSSMSEEVTYADLQFQNSSEMEKIPEIGKFGEKAPPAPSHVWRPAALFLTLLC

LLLLIGLGVLASMFHVTLKIEMKKMNKLQNISEELQRNISLQLMSNMNISNKIRNLSTTL

QTIATKLCRELYSKEQEHKCKPCPRRWIWHKDSCYFLSDDVQTWQESKMACAAQNASL

LKINNKNALEFIKSQSRSYDYWLGLSPEEDSTRGMRVDNIINSSAWVIRNAPDLNNMYC

GYINRLYVQYYHCTYKQRMICEKMANPVQLGSTYFREA

SEQ ID NO:29 (underlining denotes CDR1, CDR2, CDR3, sequentially;
***bolded italics at C-terminus denotes a linker of 9 amino acids
(TSGPGGQGA (SEQ ID NO: 31))***
QVQLQESGGGLVQAGGSLRLSCVASGSIRSINVMGWYRQAPGKQRELVAACASDGNTY

YADSVKGRFTISRDNAEKTVYLQMNNLKPDDTAVYYCDANSRGNYYSGQGTQVTVSS

*TSGPGGQGA*

The invention claimed is:

1. A single domain (VHH) antibody, or antigen-binding fragment thereof, comprising SEQ ID NO. 36 (CDR1), SEQ ID NO. 47 (CDR2), and SEQ ID NO. 58 (CDR3).

2. The VHH antibody, or antigen-binding fragment thereof, of claim 1 comprising the amino acid sequence of SEQ ID NO. 15 lacking the C-terminal amino acids TSGPGGQGAEQKLISEEDLGAHHHHHHGAS (SEQ ID NO: 30) depicted in SEQ ID NO. 15.

3. A single domain VHH antibody, or antigen-binding fragment thereof, comprising SEQ ID NO. 36 (CDR1), SEQ ID NO. 47 (CDR2), and SEQ ID NO. 58 (CDR3) and having an amino acid sequence having at least 85%, 90%, 91%, 92%, 93%, 94%, 95%, 96%, 97%, 98%, 99%, or 100% sequence identity to SEQ ID NO. 15 lacking the C-terminal amino acids TSGPGGQGAEQKLISEEDLGAHHHHHH-GAS (SEQ ID NO: 30) depicted in SEQ ID NO. 15.

4. A fusion protein comprising the VHH antibody or antigen-binding fragment thereof of claim 1, and a B cell antigen or a portion thereof.

5. A nucleic acid sequence encoding the VHH antibody or antigen-binding fragment thereof of claim 1.

6. A vector comprising the nucleic acid sequence of claim 5.

7. An isolated cell comprising the nucleic acid sequence of claim 5.

8. A method of producing an antibody, or antigen-binding fragment thereof comprising culturing the cell of claim 7 under conditions suitable for expression of the VHH antibody or antigen-binding fragment thereof.

9. A method of treating a CLL-1 associated disease or disorder correlated with elevated cell surface expression of CLL-1, the method comprising administering to a subject in need thereof an effective amount of the fusion protein of claim 4.

10. A nucleic acid sequence encoding the fusion protein of claim 4.

11. A vector comprising the nucleic acid sequence of claim 4.

12. An isolated cell comprising the nucleic acid sequence of claim 10.

13. A method of producing a fusion protein, comprising culturing the cell of claim 12 under conditions suitable for expression of the fusion protein.

* * * * *

SEQUENCE LISTING

<160> NUMBER OF SEQ ID NOS: 89

<210> SEQ ID NO 1
<211> LENGTH: 801
<212> TYPE: DNA
<213> ORGANISM: Homo sapiens

<400> SEQUENCE: 1

```
atgtctgaag aagttactta tgcagatctt caattccaga actccagtga gatggaaaaa        60
atcccagaaa ttggcaaatt tggggaaaaa gcacctccag ctccctctca tgtatggcgt       120
ccagcagcct tgtttctgac tcttctgtgc cttctgttgc tcattggatt gggagtcttg       180
gcaagcatgt ttcatgtaac tttgaagata gaaatgaaaa aaatgaacaa actacaaaac       240
atcagtgaag agctccagag aaatatttct ctacaactga tgagtaacat gaatatctcc       300
aacaagatca ggaacctctc caccacactg caaacaatag ccaccaaatt atgtcgtgag       360
ctatatagca agaacaaga gcacaaatgt aagccttgtc caaggagatg gatttggcat       420
aaggacagct gttatttcct aagtgatgat gtccaaacat ggcaggagag taaaatggcc       480
tgtgctgctc agaatgccag cctgttgaag ataaacaaca aaaatgcatt ggaatttata       540
aaatcccaga gtagatcata tgactattgg ctgggattat ctcctgaaga agattccact       600
cgtggtatga gagtggataa tataatcaac tcctctgcct gggttataag aaacgcacct       660
gacttaaata acatgtattg tggatatata aatagactat atgttcaata ttatcactgc       720
acttataaac aaagaatgat atgtgagaag atggccaatc cagtgcagct tggttctaca       780
tattttaggg aggcatgagg c                                                801
```

<210> SEQ ID NO 2
<211> LENGTH: 265
<212> TYPE: PRT
<213> ORGANISM: Homo sapiens

<400> SEQUENCE: 2

```
Met Ser Glu Glu Val Thr Tyr Ala Asp Leu Gln Phe Gln Asn Ser Ser
1               5                   10                  15

Glu Met Glu Lys Ile Pro Glu Ile Gly Lys Phe Gly Glu Lys Ala Pro
            20                  25                  30

Pro Ala Pro Ser His Val Trp Arg Pro Ala Ala Leu Phe Leu Thr Leu
        35                  40                  45

Leu Cys Leu Leu Leu Leu Ile Gly Leu Gly Val Leu Ala Ser Met Phe
    50                  55                  60

His Val Thr Leu Lys Ile Glu Met Lys Lys Met Asn Lys Leu Gln Asn
65                  70                  75                  80

Ile Ser Glu Glu Leu Gln Arg Asn Ile Ser Leu Gln Leu Met Ser Asn
                85                  90                  95

Met Asn Ile Ser Asn Lys Ile Arg Asn Leu Ser Thr Thr Leu Gln Thr
            100                 105                 110

Ile Ala Thr Lys Leu Cys Arg Glu Leu Tyr Ser Lys Glu Gln Glu His
        115                 120                 125

Lys Cys Lys Pro Cys Pro Arg Arg Trp Ile Trp His Lys Asp Ser Cys
        130                 135                 140

Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175
```

-continued

```
Leu Glu Phe Ile Lys Ser Gln Ser Arg Ser Tyr Asp Tyr Trp Leu Gly
            180                 185                 190

Leu Ser Pro Glu Glu Asp Ser Thr Arg Gly Met Arg Val Asp Asn Ile
        195                 200                 205

Ile Asn Ser Ser Ala Trp Val Ile Arg Asn Ala Pro Asp Leu Asn Asn
    210                 215                 220

Met Tyr Cys Gly Tyr Ile Asn Arg Leu Tyr Val Gln Tyr Tyr His Cys
225                 230                 235                 240

Thr Tyr Lys Lys Arg Met Ile Cys Glu Lys Met Ala Asn Pro Val Gln
            245                 250                 255

Leu Gly Ser Thr Tyr Phe Arg Glu Ala
            260                 265
```

```
<210> SEQ ID NO 3
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
            85                  90                  95

Tyr Cys Asp Ala Asn Ser Arg Gly Asn Tyr Tyr Ser Gly Gln Gly Thr
            100                 105                 110

Gln Val Thr Val Ser Ser Thr Ser Gly Pro Gly Gly Gln Gly Ala Glu
        115                 120                 125

Gln Lys Leu Ile Ser Glu Glu Asp Leu Gly Ala His His His His His
    130                 135                 140

His Gly Ala Ser
145
```

```
<210> SEQ ID NO 4
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45
```

-continued

```
Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Leu Val Thr Val Ser Ser Thr Ser Gly Pro Gly Gly Gln Gly Ala Glu
            115                 120                 125

Gln Lys Leu Ile Ser Glu Glu Asp Leu Gly Ala His His His His His
    130                 135                 140

His Gly Ala Ser
145

<210> SEQ ID NO 5
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Gln Ser Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
            35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Gln Val Thr Val Ser Ser Thr Ser Gly Pro Gly Gly Gln Gly Ala Glu
            115                 120                 125

Gln Lys Leu Ile Ser Glu Glu Asp Leu Gly Ala His His His His His
    130                 135                 140

His Gly Ala Ser
145

<210> SEQ ID NO 6
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Gln Ser Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30
```

-continued

```
Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
                100                 105                 110

Leu Val Thr Val Ser Ser Thr Ser Gly Pro Gly Gly Gln Gly Ala Glu
            115                 120                 125

Gln Lys Leu Ile Ser Glu Glu Asp Leu Gly Ala His His His His His
        130                 135                 140

His Gly Ala Ser
145

<210> SEQ ID NO 7
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Gln Phe Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
                100                 105                 110

Leu Val Thr Val Ser Ser Thr Ser Gly Pro Gly Gly Gln Gly Ala Glu
            115                 120                 125

Gln Lys Leu Ile Ser Glu Glu Asp Leu Gly Ala His His His His His
        130                 135                 140

His Gly Ala Ser
145

<210> SEQ ID NO 8
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Ala Ser Gly Gly Gly Leu Val Gln Ala Gly Gly
1               5                   10                  15
```

```
Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
            35                  40                  45

Glu Leu Val Ala Ala Cys Ala Ser Asp Gly Asn Thr Tyr Tyr Ala Asp
        50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                    85                  90                  95

Tyr Cys Asp Ala Asn Ser Arg Gly Asn Tyr Tyr Ser Gly Gln Gly Thr
                100                 105                 110

Gln Val Thr Val Ser Ser Thr Ser Gly Pro Gly Gly Gln Gly Ala Glu
            115                 120                 125

Gln Lys Leu Ile Ser Glu Glu Asp Leu Gly Ala His His His His His
        130                 135                 140

His Gly Ala Ser
145

<210> SEQ ID NO 9
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Phe Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
            35                  40                  45

Glu Leu Val Ala Ala Cys Ala Ser Asp Gly Asn Thr Tyr Tyr Ala Asp
        50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                    85                  90                  95

Tyr Cys Asp Ala Asn Ser Arg Gly Asn Tyr Tyr Ser Gly Gln Gly Thr
                100                 105                 110

Leu Val Thr Val Ser Ser Thr Ser Gly Pro Gly Gly Gln Gly Ala Glu
            115                 120                 125

Gln Lys Leu Ile Ser Glu Glu Asp Leu Gly Ala His His His His His
        130                 135                 140

His Gly Ala Ser
145

<210> SEQ ID NO 10
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

```
Gln Val Gln Leu Gln Glu Phe Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Gln Val Thr Val Ser Ser Thr Ser Gly Pro Gly Gly Gln Gly Ala Glu
            115                 120                 125

Gln Lys Leu Ile Ser Glu Glu Asp Leu Gly Ala His His His His His
    130                 135                 140

His Gly Ala Ser
145

<210> SEQ ID NO 11
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
        35                  40                  45

Glu Leu Val Ala Ala Cys Ala Ser Asp Gly Asn Thr Tyr Tyr Ala Asp
    50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Leu Val Thr Val Ser Ser Thr Ser Gly Pro Gly Gly Gln Gly Ala Glu
            115                 120                 125

Gln Lys Leu Ile Ser Glu Glu Asp Leu Gly Ala His His His His His
    130                 135                 140

His Gly Ala Ser
145

<210> SEQ ID NO 12
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 12

```
Gln Val Gln Leu Gln Gln Ser Gly Gly Gly Leu Ala Gln Thr Gly Gly
1               5                   10                  15

Ser Leu Ile Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
            35                  40                  45

Glu Leu Val Ala Ala Cys Ala Ser Asp Gly Asn Thr Tyr Tyr Ala Asp
        50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Gln Val Thr Val Ser Ser Thr Ser Gly Pro Gly Gly Gln Gly Ala Glu
        115                 120                 125

Gln Lys Leu Ile Ser Glu Glu Asp Leu Gly Ala His His His His His
    130                 135                 140

His Gly Ala Ser
145
```

<210> SEQ ID NO 13
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ala Ile Asn
            20                  25                  30

Glu Ile Asn Leu Met Gly Trp Tyr Arg Gln Ala Pro Gly Lys Gln Arg
            35                  40                  45

Glu Leu Val Ala Ala Cys Ala Ser Asp Gly Asn Thr Tyr Tyr Ala Asp
        50                  55                  60

Ser Val Lys Gly Arg Phe Thr Ile Ser Arg Asp Asn Ala Glu Lys Thr
65                  70                  75                  80

Val Tyr Leu Gln Met Asn Asn Leu Lys Pro Asp Asp Thr Ala Val Tyr
                85                  90                  95

Tyr Cys Asp Ala Asn Ser Arg Gly Asn Tyr Tyr Ser Gly Gln Gly Thr
            100                 105                 110

Leu Val Thr Val Ser Ser Thr Ser Gly Pro Gly Gly Gln Gly Ala Glu
        115                 120                 125

Gln Lys Leu Ile Ser Glu Glu Asp Leu Gly Ala His His His His His
    130                 135                 140

His Gly Ala Ser
145
```

<210> SEQ ID NO 14
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Glu Ser Gly Gly Gly Leu Val Gln Val Gly Glu
1               5                   10                  15

Ser Leu Arg Leu Ser Cys Val Val Ser Gly Asp Thr Arg Ser Ile Asn
            20                  25                  30

Leu Met Gly Trp Tyr Arg Gln Ala Pro Gly Lys Gln Arg Glu Leu Val
            35                  40                  45

Ala Ala Cys Ala Ser Asp Gly Asn Thr Tyr Tyr Ala Asp Ser Val Lys
        50                  55                  60

Gly Arg Phe Thr Ile Ser Arg Asp Asn Ala Glu Lys Thr Val Tyr Leu
65                  70                  75                  80

Gln Met Asn Asn Leu Lys Pro Asp Asp Thr Ala Val Tyr Tyr Cys Asp
                85                  90                  95

Ala Asn Ser Arg Gly Asn Tyr Tyr Ser Gly Gln Gly Thr Leu Val Thr
            100                 105                 110

Val Ser Ser Thr Ser Gly Pro Gly Gly Gln Gly Ala Glu Gln Lys Leu
            115                 120                 125

Ile Ser Glu Glu Asp Leu Gly Ala His His His His His His Gly Ala
        130                 135                 140

Ser
145

<210> SEQ ID NO 15
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Glu Ser Gly Gly Gly Leu Val Gln Ala Gly Gly
1               5                   10                  15

Ser Leu Arg Leu Ser Cys Val Ala Ser Gly Ser Ile Arg Ser Ile Asn
            20                  25                  30

Val Met Gly Trp Tyr Arg Gln Ala Pro Gly Lys Gln Arg Glu Leu Val
            35                  40                  45

Ala Ala Cys Ala Ser Asp Gly Asn Thr Tyr Tyr Ala Asp Ser Val Lys
        50                  55                  60

Gly Arg Phe Thr Ile Ser Arg Asp Asn Ala Glu Lys Thr Val Tyr Leu
65                  70                  75                  80

Gln Met Asn Asn Leu Lys Pro Asp Asp Thr Ala Val Tyr Tyr Cys Asp
                85                  90                  95

Ala Asn Ser Arg Gly Asn Tyr Tyr Ser Gly Gln Gly Thr Gln Val Thr
            100                 105                 110

Val Ser Ser Thr Ser Gly Pro Gly Gly Gln Gly Ala Glu Gln Lys Leu
            115                 120                 125

Ile Ser Glu Glu Asp Leu Gly Ala His His His His His His Gly Ala
        130                 135                 140

Ser
145

<210> SEQ ID NO 16

-continued

```
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Thr Trp Val Arg Gln Ala Pro Gly Lys Gly Leu Glu Trp Val
        35                  40                  45

Ser Asp Ile Asn Ser Gly Gly Gly Ser Thr Asn Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr Glu Leu Arg Gly Ser Asp Tyr Tyr Arg Gly Pro Ile Arg Glu
            100                 105                 110

Tyr Ala Tyr Trp Gly Gln Gly Thr Leu Val Thr Val Ser Ser Thr Ser
        115                 120                 125

Gly Pro Gly Gly Gln Gly Ala Glu Gln Lys Leu Ile Ser Glu Glu Asp
    130                 135                 140

Leu Gly Ala His His His His His His Gly Ala Ser
145                 150                 155

<210> SEQ ID NO 17
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Gly Ala Leu Val Gln Ala Gly Gly
1               5                   10                  15

Ser Leu Arg Leu Ser Cys Ala Ala Ser Gly Leu Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Trp Ser Gly Gly Thr Thr Asp Tyr Ala Thr Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Ser Tyr Arg Leu Arg Ile Thr Val Val Val Thr Pro Asp Glu
            100                 105                 110

Tyr His Tyr Trp Gly Gln Gly Thr Leu Val Thr Val Ser Ser Thr Ser
        115                 120                 125

Gly Pro Gly Gly Gln Gly Ala Glu Gln Lys Leu Ile Ser Glu Glu Asp
    130                 135                 140

Leu Gly Ala His His His His His His Gly Ala Ser
145                 150                 155
```

```
<210> SEQ ID NO 18
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
            20                  25                  30

Ala Met Ile Trp Val Arg Gln Gly Pro Gly Lys Gly Leu Glu Trp Val
        35                  40                  45

Ser Ser Ile Ser Trp Asn Gly Gly Thr Tyr Tyr Ala Glu Ser Ile
    50                  55                  60

Val Gly Arg Phe Thr Val Ser Arg Asp Asn Ala Lys Lys Met Val Tyr
65                  70                  75                  80

Leu Gln Met Asn Gly Leu Lys Ser Glu Asp Thr Ala Met Tyr Tyr Cys
                85                  90                  95

Val Lys Leu Val Asp Ser Gly Trp Tyr Ser Ala Tyr Asp Tyr Trp Gly
            100                 105                 110

Gln Gly Thr Gln Val Thr Val Ser Ser Thr Ser Gly Pro Gly Gly Gln
        115                 120                 125

Gly Ala Glu Gln Lys Leu Ile Ser Glu Glu Asp Leu Gly Ala His His
    130                 135                 140

His His His His Gly Ala Ser
145                 150

<210> SEQ ID NO 19
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Glu Ser Gly Gly Gly Leu Val Gln Ala Gly Gly
1               5                   10                  15

Ser Leu Arg Leu Ser Cys Val Val Ser Gly Ala Thr Ser Asn Val Asn
            20                  25                  30

Ala Met Gly Trp Tyr Arg Gln Ala Pro Gly Lys Glu Arg Glu Leu Val
        35                  40                  45

Ala Ala Ile Ser Ser Gly Gly Ser Thr Ser Tyr Arg Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Gln Asp Trp Ala Thr Glu Gly Tyr Glu Tyr Asp Tyr Trp Gly Gln
            100                 105                 110

Gly Thr Leu Val Thr Val Ser Ser Thr Ser Gly Pro Gly Gly Gln Gly
        115                 120                 125

Ala Glu Gln Lys Leu Ile Ser Glu Glu Asp Leu Gly Ala His His His
    130                 135                 140
```

His His His Gly Ala Ser
145                 150

<210> SEQ ID NO 20
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Ala Phe Gly Gly Gly Leu Val Gln Pro Gly Gly
1               5                   10                  15

Ser Leu Arg Leu Ser Cys Val Val Ser Gly Thr Met Phe Ser Gly Lys
            20                  25                  30

Asp Val Asn Trp Leu Arg Gln Ala Pro Gly Lys His Val Glu Val Val
            35                  40                  45

Ala Thr Val Ser Ser Asp Gly Gly Thr Asp Tyr Ala Asp Phe Val Lys
        50                  55                  60

Gly Arg Phe Thr Ile Ser Arg Asp Asp Ala Lys Asn Thr Val Asn Leu
65                  70                  75                  80

Gln Met Asn Ser Leu Glu Pro Glu Asp Thr Ala Asn Tyr Met Cys His
                85                  90                  95

Phe Leu Trp Gly Arg His Tyr Trp Gly Gln Gly Thr Gln Val Thr Val
                100                 105                 110

Ser Ser Thr Ser Gly Pro Gly Gly Gln Gly Ala Glu Gln Lys Leu Ile
            115                 120                 125

Ser Glu Glu Asp Leu Gly Ala His His His His His Gly Ala Ser
        130                 135                 140

<210> SEQ ID NO 21
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Ala Phe Gly Gly Gly Met Val Gln Ala Gly Glu
1               5                   10                  15

Ser Leu Arg Leu Ser Cys Val Ala Ser Gly Asn Asp Ile Ser Gly Ser
            20                  25                  30

Ala Met Ala Trp Tyr Arg Ala His Leu Gly Ala Glu Arg Glu Leu Val
        35                  40                  45

Ala Val Asp Ala Pro Arg Glu Arg Pro Phe Tyr Ile Asp Pro Val Ile
        50                  55                  60

Gly Arg Phe Thr Ile Ser Arg Asp Asp Arg Asn Lys Met Leu Tyr Leu
65                  70                  75                  80

Gln Met Asn Asp Leu Arg Pro Asp Asp Thr Ala Thr Tyr Trp Cys Gly
                85                  90                  95

Pro Ser Leu Arg Thr Phe His Gly Arg Glu Trp Tyr Arg Pro Pro Trp
            100                 105                 110

Phe Thr Ser Trp Gly Gln Gly Thr Gln Val Thr Val Ser Ser Thr Ser
            115                 120                 125

Gly Pro Gly Gly Gln Gly Ala Glu Gln Lys Leu Ile Ser Glu Glu Asp
        130                 135                 140

-continued

```
Leu Gly Ala His His His His His His Gly Ala Ser
145                 150                 155

<210> SEQ ID NO 22
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Gln Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Arg Arg Glu Met Val
        35                  40                  45

Ala Val Val Ser Arg Phe Gly Glu Thr Thr Tyr Thr Gly Ser Val Lys
    50                  55                  60

Gly Arg Phe Thr Ile Ser Arg Ile Asn Arg Asn Asn Thr Val Phe Leu
65                  70                  75                  80

Gln Met Asn Arg Leu Lys Pro Glu Asp Thr Ala Val Tyr Tyr Cys Asn
                85                  90                  95

Ala Arg Ile Arg Gly Asn Tyr Gly Ser Arg Ile Asp Tyr Trp Gly Gln
            100                 105                 110

Gly Thr Gln Val Thr Val Ser Ser Thr Ser Gly Pro Gly Gly Gln Gly
        115                 120                 125

Ala Glu Gln Lys Leu Ile Ser Glu Glu Asp Leu Gly Ala His His His
    130                 135                 140

His His His Gly Ala Ser
145                 150

<210> SEQ ID NO 23
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Glu Phe Gly Gly Gly Leu Val Gln Leu Gly Gly
1               5                   10                  15

Ser Ala Arg Leu Ser Cys Val Val Ser Gly Asn Met Leu Asp Leu Asn
            20                  25                  30

Thr Met Ala Trp Tyr Arg Gln Gly Glu Leu Val Ala Ala Leu Gly Ile
        35                  40                  45

Ser Thr Tyr Tyr Ala Glu Ser Val Lys Gly Arg Phe Thr Ile Ser Arg
    50                  55                  60

Asp Asn Ala Lys Asn Thr Leu Tyr Leu Gln Met Asn Ser Leu Lys Ser
65                  70                  75                  80

Glu Asp Thr Ala Val Tyr Tyr Cys Ala Arg Asp Tyr Asn Phe Glu Ser
                85                  90                  95

Trp Gly Gln Gly Thr Leu Val Thr Val Ser Ser Thr Ser Gly Pro Gly
            100                 105                 110

Gly Gln Gly Ala Glu Gln Lys Leu Ile Ser Glu Glu Asp Leu Gly Ala
        115                 120                 125
```

```
His His His His His His Gly Ala Ser
    130                 135

<210> SEQ ID NO 24
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Val Gln Leu Gln Glu Ser Gly Gly Gly Leu Val Gln Ala Gly Gly
1               5                   10                  15

Ser Leu Arg Leu Ser Cys Ala Ala Ser Gly Ser Asp Arg Ser Ile Asn
            20                  25                  30

Val Met Asn Trp Tyr Arg Gln Ala Pro Gly Lys Gln Arg Glu Leu Val
            35                  40                  45

Ala Ala Ile Thr Ser Gly Gly Thr Thr Asn Tyr Ala Gln Ser Val Lys
    50                  55                  60

Gly Arg Val Thr Ile Ser Arg Asp Ser Ala Lys Asn Thr Val Tyr Leu
65                  70                  75                  80

Gln Met Asn Ser Leu Lys Pro Glu Asp Thr Ala Val Tyr Phe Cys Lys
                85                  90                  95

Ala Asp Thr Arg Trp Gly Gly Met Tyr Trp Gly Pro Gly Thr Gln Val
            100                 105                 110

Thr Val Ser Ser Thr Ser Gly Pro Gly Gly Gln Gly Ala Glu Gln Lys
        115                 120                 125

Leu Ile Ser Glu Glu Asp Leu Gly Ala His His His His His Gly
    130                 135                 140

Ala Ser
145

<210> SEQ ID NO 25
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Gln Ser Gly Gly Gly Leu Val Gln Ala Gly Gly
1               5                   10                  15

Ser Leu Thr Leu Ser Cys Ala Ala Thr Gly Arg Thr Ile Asp Asn Gly
            20                  25                  30

Ala Met Ala Trp Phe Arg Gln Ala Pro Gly Lys Gln Arg Glu Leu Val
            35                  40                  45

Ala Ala Ile Asn Trp Ser Gly Gly Ala Thr Phe Tyr Thr Asp Ser Val
    50                  55                  60

Lys Tyr Arg Phe Thr Ile Ser Arg Asp Asn Val Arg His Thr Leu Asp
65                  70                  75                  80

Leu Gln Met Thr Ser Leu Lys Pro Glu Asp Thr Thr Ile Tyr Phe Cys
                85                  90                  95

Ala Ser Arg Arg Gly Val Asp Leu Arg Arg Asn Ser Tyr Glu Tyr Asp
            100                 105                 110

Tyr Trp Gly Arg Gly Thr Leu Val Thr Val Ser Ser Thr Ser Gly Pro
        115                 120                 125
```

```
Gly Gly Gln Gly Ala Glu Gln Lys Leu Ile Ser Glu Glu Asp Leu Gly
    130                 135                 140

Ala His His His His His His Gly Ala Ser
145                 150

<210> SEQ ID NO 26
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Gln Glu Ser Gly Pro Gly Leu Val Lys Pro Ser Glu
1                   5                   10                  15

Thr Leu Ser Leu Thr Cys Val Val Ser Gly Gly Ser Ile Ser Ser Ser
            20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Pro Asp Tyr Asn Pro Ser Leu
    50                  55                  60

Lys Ser Arg Val Thr Ile Ser Val Asp Lys Ser Arg Asn Gln Phe Ser
65                  70                  75                  80

Leu Lys Leu Ser Ser Val Thr Ala Ala Asp Thr Ala Val Tyr Tyr Cys
                85                  90                  95

Ala Lys Val Ser Thr Gly Gly Phe Phe Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Glu Ile Glu Leu Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
            195                 200                 205

Ser Ser Leu Gln Pro Glu Asp Phe Ala Thr Tyr Tyr Cys Gln Gln Ser
    210                 215                 220

Tyr Ser Thr Pro Pro Thr Phe Gly Pro Gly Thr Lys Val Glu Ile Lys
225                 230                 235                 240

<210> SEQ ID NO 27
<211> LENGTH: 275
<212> TYPE: PRT
<213> ORGANISM: Homo sapiens

<400> SEQUENCE: 27

Met Trp Ile Asp Phe Phe Thr Tyr Ser Ser Met Ser Glu Glu Val Thr
1                   5                   10                  15

Tyr Ala Asp Leu Gln Phe Gln Asn Ser Ser Glu Met Glu Lys Ile Pro
            20                  25                  30

Glu Ile Gly Lys Phe Gly Glu Lys Ala Pro Pro Ala Pro Ser His Val
            35                  40                  45
```

```
Trp Arg Pro Ala Ala Leu Phe Leu Thr Leu Leu Cys Leu Leu Leu Leu
    50              55              60
Ile Gly Leu Gly Val Leu Ala Ser Met Phe His Val Thr Leu Lys Ile
65              70              75              80
Glu Met Lys Lys Met Asn Lys Leu Gln Asn Ile Ser Glu Glu Leu Gln
                85              90              95
Arg Asn Ile Ser Leu Gln Leu Met Ser Asn Met Asn Ile Ser Asn Lys
            100             105             110
Ile Arg Asn Leu Ser Thr Thr Leu Gln Thr Ile Ala Thr Lys Leu Cys
            115             120             125
Arg Glu Leu Tyr Ser Lys Glu Gln Glu His Lys Cys Lys Pro Cys Pro
    130             135             140
Arg Arg Trp Ile Trp His Lys Asp Ser Cys Tyr Phe Leu Ser Asp Asp
145             150             155             160
Val Gln Thr Trp Gln Glu Ser Lys Met Ala Cys Ala Ala Gln Asn Ala
                165             170             175
Ser Leu Leu Lys Ile Asn Asn Lys Asn Ala Leu Glu Phe Ile Lys Ser
            180             185             190
Gln Ser Arg Ser Tyr Asp Tyr Trp Leu Gly Leu Ser Pro Glu Glu Asp
            195             200             205
Ser Thr Arg Gly Met Arg Val Asp Asn Ile Ile Asn Ser Ser Ala Trp
    210             215             220
Val Ile Arg Asn Ala Pro Asp Leu Asn Asn Met Tyr Cys Gly Tyr Ile
225             230             235             240
Asn Arg Leu Tyr Val Gln Tyr Tyr His Cys Thr Tyr Lys Lys Arg Met
                245             250             255
Ile Cys Glu Lys Met Ala Asn Pro Val Gln Leu Gly Ser Thr Tyr Phe
            260             265             270
Arg Glu Ala
        275

<210> SEQ ID NO 28
<211> LENGTH: 275
<212> TYPE: PRT
<213> ORGANISM: Homo sapiens

<400> SEQUENCE: 28

Met Trp Ile Asp Phe Phe Thr Tyr Ser Ser Met Ser Glu Glu Val Thr
1               5               10              15
Tyr Ala Asp Leu Gln Phe Gln Asn Ser Ser Glu Met Glu Lys Ile Pro
            20              25              30
Glu Ile Gly Lys Phe Gly Glu Lys Ala Pro Pro Ala Pro Ser His Val
            35              40              45
Trp Arg Pro Ala Ala Leu Phe Leu Thr Leu Leu Cys Leu Leu Leu Leu
    50              55              60
Ile Gly Leu Gly Val Leu Ala Ser Met Phe His Val Thr Leu Lys Ile
65              70              75              80
Glu Met Lys Lys Met Asn Lys Leu Gln Asn Ile Ser Glu Glu Leu Gln
                85              90              95
Arg Asn Ile Ser Leu Gln Leu Met Ser Asn Met Asn Ile Ser Asn Lys
            100             105             110
Ile Arg Asn Leu Ser Thr Thr Leu Gln Thr Ile Ala Thr Lys Leu Cys
            115             120             125
Arg Glu Leu Tyr Ser Lys Glu Gln Glu His Lys Cys Lys Pro Cys Pro
```

-continued

```
       130              135              140

Arg Arg Trp Ile Trp His Lys Asp Ser Cys Tyr Phe Leu Ser Asp Asp
145              150              155              160

Val Gln Thr Trp Gln Glu Ser Lys Met Ala Cys Ala Ala Gln Asn Ala
                165              170              175

Ser Leu Leu Lys Ile Asn Asn Lys Asn Ala Leu Glu Phe Ile Lys Ser
            180              185              190

Gln Ser Arg Ser Tyr Asp Tyr Trp Leu Gly Leu Ser Pro Glu Glu Asp
        195              200              205

Ser Thr Arg Gly Met Arg Val Asp Asn Ile Ile Asn Ser Ser Ala Trp
    210              215              220

Val Ile Arg Asn Ala Pro Asp Leu Asn Asn Met Tyr Cys Gly Tyr Ile
225              230              235              240

Asn Arg Leu Tyr Val Gln Tyr Tyr His Cys Thr Tyr Lys Gln Arg Met
                245              250              255

Ile Cys Glu Lys Met Ala Asn Pro Val Gln Leu Gly Ser Thr Tyr Phe
            260              265              270

Arg Glu Ala
        275
```

```
<210> SEQ ID NO 29
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Glu Ser Gly Gly Gly Leu Val Gln Ala Gly Gly
1               5               10              15

Ser Leu Arg Leu Ser Cys Val Ala Ser Gly Ser Ile Arg Ser Ile Asn
            20              25              30

Val Met Gly Trp Tyr Arg Gln Ala Pro Gly Lys Gln Arg Glu Leu Val
        35              40              45

Ala Ala Cys Ala Ser Asp Gly Asn Thr Tyr Tyr Ala Asp Ser Val Lys
    50              55              60

Gly Arg Phe Thr Ile Ser Arg Asp Asn Ala Glu Lys Thr Val Tyr Leu
65              70              75              80

Gln Met Asn Asn Leu Lys Pro Asp Asp Thr Ala Val Tyr Tyr Cys Asp
                85              90              95

Ala Asn Ser Arg Gly Asn Tyr Tyr Ser Gly Gln Gly Thr Gln Val Thr
            100             105             110

Val Ser Ser Thr Ser Gly Pro Gly Gly Gln Gly Ala
        115             120
```

```
<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Thr Ser Gly Pro Gly Gly Gln Gly Ala Glu Gln Lys Leu Ile Ser Glu
1               5               10              15

Glu Asp Leu Gly Ala His His His His His Gly Ala Ser
```

-continued

```
              20              25              30
```

```
<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Ser Gly Pro Gly Gly Gln Gly Ala
1               5

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Glu Gln Lys Leu Ile Ser Glu Glu Asp Leu
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
1               5

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Ala Ala Ser Gly Ser Ile Phe Ala Ile Asn Glu Ile
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Cys Val Val Ser Gly Asp Thr Arg Ser Ile
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
         peptide

<400> SEQUENCE: 36

Cys Val Ala Ser Gly Ser Ile Arg Ser Ile
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Ala Ala Ser Gly Phe Thr Phe Asn Ser Tyr Ala
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Ala Ala Ser Gly Leu Thr Phe Ser Asn Tyr Ala
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Ala Ala Ser Gly Phe Ala Phe Asp Asp Tyr Ala
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Val Val Ser Gly Ala Thr Ser Asn Val Asn Ala
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Val Val Ser Gly Thr Met Phe Ser Gly Lys Asp
1               5                   10

<210> SEQ ID NO 42
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Val Ala Ser Gly Asn Asp Ile Ser Gly Ser Ala
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Ala Ala Ser Gly Ser Ile Phe Ser Ile Asn Ala
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Val Val Ser Gly Asn Met Leu Asp Leu Asn Thr
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Ser Asp Arg Ser Ile Asn Val
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Arg Thr Ile Asp Asn Gly Ala
1               5

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

```
Val Ala Ala Cys Ala Ser Asp Gly Asn Thr Tyr
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Trp Val Ser Asp Ile Asn Ser Gly Gly Gly Ser Thr Asn
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Ile Asn Trp Ser Gly Gly Thr Thr Asp
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Val Ser Ser Ile Ser Trp Asn Gly Gly Gly Thr Tyr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Val Ala Ala Ile Ser Ser Gly Gly Ser Thr Ser
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Val Ala Thr Val Ser Ser Asp Gly Gly Thr Asp
1               5                   10

<210> SEQ ID NO 53
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 53

Val Ala Val Asp Ala Pro Arg Glu Arg Pro Phe
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Ala Val Val Ser Arg Phe Gly Glu Thr Thr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Val Ala Ala Leu Gly Ile Ser Thr Tyr
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Thr Ser Gly Gly Thr Thr
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ile Asn Trp Ser Gly Gly Ala Thr
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Ala Asn Ser Arg Gly Asn Tyr Tyr
1               5

```
<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Thr Glu Leu Arg Gly Ser Asp Tyr Tyr Arg Gly Pro Ile Arg Glu
1               5                   10                  15

Tyr Ala Tyr

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Ala Ser Tyr Arg Leu Arg Ile Thr Val Val Val Thr Pro Asp Glu
1               5                   10                  15

Tyr His Tyr

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Val Lys Leu Val Asp Ser Gly Trp Tyr Ser Ala Tyr Asp Tyr
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Ala Gln Asp Trp Ala Thr Glu Gly Tyr Glu Tyr Asp Tyr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

His Phe Leu Trp Gly Arg His Tyr
1               5

<210> SEQ ID NO 64
<211> LENGTH: 20
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 64

Gly Pro Ser Leu Arg Thr Phe His Gly Arg Glu Trp Tyr Arg Pro Pro
1               5                   10                  15

Trp Phe Thr Ser
            20

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asn Ala Arg Ile Arg Gly Asn Tyr Gly Ser Arg Ile Asp Tyr
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Arg Asp Tyr Asn Phe Glu Ser
1               5

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Ala Asp Thr Arg Trp Gly Gly Met Tyr
1               5                   10

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Ser Arg Arg Gly Val Asp Leu Arg Arg Asn Ser Tyr Glu Tyr Asp
1               5                   10                  15

Tyr

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Gly Ser Ile Phe Ala Ile Asn Glu Ile Asn Leu
1               5                   10

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Asp Thr Arg Ser Ile Asn Leu
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ser Ile Arg Ser Ile Asn Val
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Phe Thr Phe Asn Ser Tyr Ala
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Leu Thr Phe Ser Asn Tyr Ala
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Phe Ala Phe Asp Asp Tyr Ala
1               5

<210> SEQ ID NO 75
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 75

Gly Ala Thr Ser Asn Val Asn Ala
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Thr Met Phe Ser Gly Lys Asp
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Asn Asp Ile Ser Gly Ser Ala
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Ser Ile Phe Ser Ile Asn Ala
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Asn Met Leu Asp Leu Asn Thr
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Cys Ala Ser Asp Gly Asn Thr
1               5
```

```
<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ile Asn Ser Gly Gly Gly Ser Thr
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Asn Trp Ser Gly Gly Thr Thr
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ile Ser Trp Asn Gly Gly Gly Thr
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ile Ser Ser Gly Gly Ser Thr
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Val Ser Ser Asp Gly Gly Thr
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 86

Val Asp Ala Pro Arg Glu Arg Pro
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Ser Arg Phe Gly Glu Thr
1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Leu Gly Ile Ser Thr
1               5

<210> SEQ ID NO 89
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Tyr Val Gln Tyr Tyr His Cys Thr Tyr Lys Gln Arg Met Ile Cys Glu
1               5                   10                  15

Lys Met Ala Asn Pro Val Gln Leu Gly Ser Thr Tyr Phe Arg Glu
            20                  25                  30
```